US010968217B2

(12) United States Patent
Cheng et al.

(10) Patent No.: US 10,968,217 B2
(45) Date of Patent: Apr. 6, 2021

(54) TETRAHYDROPYRIDOPYRIMIDINES FOR THE TREATMENT AND PROPHYLAXIS OF HEPATITIS B VIRUS INFECTION

(71) Applicant: Hoffmann-La Roche Inc., Little Falls, NJ (US)

(72) Inventors: Zhanling Cheng, Shanghai (CN); Jianhua Wang, Shanghai (CN); Min Wang, Shanghai (CN); Song Yang, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/346,985

(22) PCT Filed: Nov. 1, 2017

(86) PCT No.: PCT/EP2017/077934
§ 371 (c)(1),
(2) Date: May 2, 2019

(87) PCT Pub. No.: WO2018/083106
PCT Pub. Date: May 11, 2018

(65) Prior Publication Data
US 2020/0062747 A1      Feb. 27, 2020

(30) Foreign Application Priority Data

Nov. 3, 2016 (WO) ............... PCT/CN2016/104436

(51) Int. Cl.
*C07D 471/04* (2006.01)
*A61K 31/519* (2006.01)
*A61P 31/20* (2006.01)

(52) U.S. Cl.
CPC .......... *C07D 471/04* (2013.01); *A61K 31/519* (2013.01); *A61P 31/20* (2018.01)

(58) Field of Classification Search
CPC ...... C07D 471/04; A61K 31/519; A61P 31/20
USPC ....................................... 544/279; 514/258.1
See application file for complete search history.

(56) References Cited

U.S. PATENT DOCUMENTS

2020/0062747 A1* 2/2020 Cheng ................. C07D 471/04

FOREIGN PATENT DOCUMENTS

| CN | 105669672 A    | 6/2016  |
|----|----------------|---------|
| CN | 106397433 A    | 2/2017  |
| WO | 2005/035526 A1 | 4/2005  |
| WO | 2010/138430 A1 | 12/2010 |
| WO | 2013/087815 A1 | 6/2013  |
| WO | 2016/107832 A1 | 7/2016  |
| WO | 2016/177655 A1 | 11/2016 |

OTHER PUBLICATIONS

International Preliminary Report on Patentability—PCT/EP2017/077934:pp. 1-8 (dated May 16, 2019).
"International Search Report—PCT/EP2017/077934":pp. 1-6 (dated Dec. 12, 2017).

* cited by examiner

*Primary Examiner* — Venkataraman Balasubramanian
(74) *Attorney, Agent, or Firm* — Genentech, Inc.; Richard G. A. Bone

(57) ABSTRACT

The present invention provides novel compounds having the general formula (I) wherein $R^1$, $R^2$ and Z are as described herein, compositions including the compounds and methods of using the compounds.

14 Claims, No Drawings

TETRAHYDROPYRIDOPYRIMIDINES FOR THE TREATMENT AND PROPHYLAXIS OF HEPATITIS B VIRUS INFECTION

The present invention relates to organic compounds useful for therapy and/or prophylaxis in a mammal, and in particular to HBsAg (HBV Surface antigen) inhibitors and HBV DNA production inhibitors useful for treating HBV infection.

FIELD OF THE INVENTION

The present invention relates to novel tetrahydropyridopyrimidines having pharmaceutical activity, their manufacture, pharmaceutical compositions containing them and their potential use as medicaments.

The present invention relates to compounds of formula I

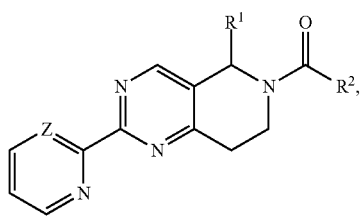

(I)

wherein $R^1$, $R^2$ and Z are as described below, or pharmaceutically acceptable salts, or enantiomers thereof.

The hepatitis B virus (HBV) is an enveloped, partially double-stranded DNA virus. The compact 3.2 kb HBV genome consists of four overlapping open reading frames (ORF), which encode for the core, polymerase (Pol), envelope and X-proteins. The Pol ORF is the longest and the envelope ORF is located within it, while the X and core ORFs overlap with the Pol ORF. The lifecycle of HBV has two main events: 1) generation of closed circular DNA (cccDNA) from relaxed circular (RC DNA), and 2) reverse transcription of pregenomic RNA (pgRNA) to produce RC DNA. Prior to the infection of host cells, the HBV genome exists within the virion as RC DNA. It has been determined that HBV virions are able to gain entry into host cells by non-specifically binding to the negatively charged proteoglycans present on the surface of human hepatocytes (Schulze, A., P. Gripon & S. Urban. *Hepatology*, 46, (2007), 1759-68) and via the specific binding of HBV surface antigens (HBsAg) to the hepatocyte sodium-taurocholate cotransporting polypeptide (NTCP) receptor (Yan, H. et al. *J Virol*, 87, (2013), 7977-91). Once the virion has entered the cell, the viral cores and the encapsidated RC DNA are transported by host factors, via a nuclear localization signal, into the nucleus through the Impβ/Impα nuclear transport receptors. Inside the nucleus, host DNA repair enzymes convert the RC DNA into cccDNA. cccDNA acts as the template for all viral mRNAs and as such, is responsible for HBV persistence in infected individuals. The transcripts produced from cccDNA are grouped into two categories; Pregenomic RNA (pgRNA) and subgenomic RNA. Subgenomic transcripts encode for the three envelopes (L, M and S) and X proteins, and pgRNA encodes for Pre-Core, Core, and Pol proteins (Quasdorff, M. & U. Protzer. *J Viral Hepat*, 17, (2010), 527-36). Inhibition of HBV gene expression or HBV RNA synthesis leads to the inhibition of HBV viral replication and antigens production (Mao, R. et al. *PLoS Pathog*, 9, (2013), e1003494; Mao, R. et al. *J Virol*, 85, (2011), 1048-57). For instance, IFN-α was shown to inhibit HBV replication and viral HBsAg production by decreasing the transcription of pgRNA and subgenomic RNA from the HBV covalently closed circular DNA (cccDNA) minichromosome. (Belloni, L. et al. *J Clin Invest*, 122, (2012), 529-37; Mao, R. et al. *J Virol*, 85, (2011), 1048-57). All HBV viral mRNAs are capped and polyadenylated, and then exported to the cytoplasm for translation. In the cytoplasm, the assembly of new virons is initiated and nascent pgRNA is packaged with viral Pol so that reverse transcription of pgRNA, via a single stranded DNA intermediate, into RC DNA can commence. The mature nucleocapsids containing RC DNA are enveloped with cellular lipids and viral L, M, and S proteins and then the infectious HBV particles are then released by budding at the intracellular membrane (Locarnini, S. *Semin Liver Dis*, (2005), 25 Suppl 1, 9-19). Interestingly, non-infectious particles are also produced that greatly outnumber the infectious virions. These empty, enveloped particles (L, M and S) are referred to as subviral particles. Importantly, since subviral particles share the same envelope proteins and as infectious particles, it has been surmised that they act as decoys to the host immune system and have been used for HBV vaccines. The S, M, and L envelope proteins are expressed from a single ORF that contains three different start codons. All three proteins share a 226aa sequence, the S-domain, at their C-termini. M and L have additional pre-S domains, Pre-S2 and Pre-S2 and Pre-S1, respectively. However, it is the S-domain that has the HBsAg epitope (Lambert, C. & R. Prange. *Virol J*, (2007), 4, 45).

The control of viral infection needs a tight surveillance of the host innate immune system which could respond within minutes to hours after infection to impact on the initial growth of the virus and limit the development of a chronic and persistent infection. Despite the available current treatments based on IFN and nucleos(t)ide analogues, the Hepatitis B virus (HBV) infection remains a major health problem worldwide which concerns an estimated 350 million chronic carriers who have a higher risk of liver cirrhosis and hepatocellular carcinoma.

The secretion of antiviral cytokines in response to HBV infection by the hepatocytes and/or the intra-hepatic immune cells plays a central role in the viral clearance of infected liver. However, chronically infected patients only display a weak immune response due to various escape strategies adopted by the virus to counteract the host cell recognition systems and the subsequent antiviral responses.

Many observations showed that several HBV viral proteins could counteract the initial host cellular response by interfering with the viral recognition signaling system and subsequently the interferon (IFN) antiviral activity. Among these, the excessive secretion of HBV empty subviral particles (SVPs, HBsAg) may participate to the maintenance of the immunological tolerant state observed in chronically infected patients (CHB). The persistent exposure to HBsAg and other viral antigens can lead to HBV-specific T-cell deletion or to progressive functional impairment (Kondo et al. *Journal of Immunology* (1993), 150, 4659-4671; Kondo et al. *Journal of Medical Virology* (2004), 74, 425-433; Fisicaro et al. *Gastroenterology*, (2010), 138, 682-93;). Moreover HBsAg has been reported to suppress the function of immune cells such as monocytes, dendritic cells (DCs) and natural killer (NK) cells by direct interaction (Op den Brouw et al. *Immunology*, (2009b), 126, 280-9; Woltman et al. *PLoS One*, (2011), 6, e15324; Shi et al. *J Viral Hepat.* (2012), 19, e26-33; Kondo et al. *ISRN Gasteroenterology*, (2013), Article ID 935295).

HBsAg quantification is a significant biomarker for prognosis and treatment response in chronic hepatitis B. However the achievement of HBsAg loss and seroconversion is rarely observed in chronically infected patients but remains the ultimate goal of therapy. Current therapy such as Nucleos(t)ide analogues are molecules that inhibit HBV DNA synthesis but are not directed at reducing HBsAg level. Nucleos(t)ide analogs, even with prolonged therapy, have demonstrated rates of HBsAg clearance comparable to those observed naturally (between –1%-2%) (Janssen et al. *Lancet*, (2005), 365, 123-9; Marcellin et al. *N. Engl. J. Med.*, (2004), 351, 1206-17; Buster et al. *Hepatology*, (2007), 46, 388-94).

A few patent applications for HBsAg inhibitors have been published, including novel dihydroquinolizinones (WO 2015/113990, WO 2015/173164), novel pyridazones and triazinones (WO2016/023877), novel 6,7-dihydrobenzo[a]quinolizin-2-one derivatives (WO/2016/071215), novel tetrahydropyridopyrimidines and tetrahydropyridopyridines (WO2016/107832) and novel 2-oxo-6,7-dihydrobenzo[a]quinolizine-3 carboxylic acid derivatives (WO 2016/128335), showing that there are some earlier exploratory efforts ongoing in this field. However, there is no commercial product approved. Therefore, there is an unmet medical need to target HBsAg for HBV treatment (Wieland, S. F. & F. V. Chisari. *J Virol*, (2005), 79, 9369-80; Kumar et al. *J Virol*, (2011), 85, 987-95; Woltman et al. *PLoS One*, (2011), 6, e15324; Op den Brouw et al. *Immunology*, (2009b), 126, 280-9).

SUMMARY OF THE INVENTION

Objects of the present invention are novel compounds of formula I, their manufacture, medicaments based on a compound in accordance with the invention and their production as well as the use of compounds of formula I as HBV inhibitors and for the treatment or prophylaxis of HBV infection. The compounds of formula I show superior anti-HBV activity.

The present invention relates to a compound of formula I

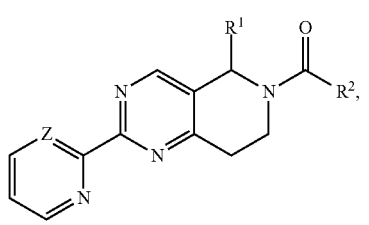

(I)

wherein
R$^1$ is C$_{1-6}$alkoxy, C$_{1-6}$alkyl, C$_{3-7}$cycloalkyl, haloC$_{1-6}$alkoxy, haloC$_{1-6}$alkyl or hydrogen;
R$^2$ is benzothiophenyl, imidazolyl, indazolyl, indolyl, isoxazolyl, oxazolyl, phenyl, pyridinyl, pyrimidinyl, thiazolyl or thiophenyl, wherein said benzothiophenyl, imidazolyl, indazolyl, indolyl, isoxazolyl, oxazolyl, phenyl, pyridinyl, thiazolyl or thiophenyl is unsubstituted or substituted by one, two or three substituents independently selected from C$_{1-6}$alkoxy, C$_{1-6}$alkoxyC$_{1-6}$alkoxy, C$_{1-6}$alkyl, C$_{3-7}$cycloalkyl, cyano, haloC$_{1-6}$alkoxy, haloC$_{1-6}$alkyl, halogen, hydroxy, hydroxyC$_{1-6}$alkoxy, hydroxyC$_{1-6}$alkyl, nitro and phenyC$_{1-6}$alkyl;
Z is CH or N;
or pharmaceutically acceptable salts, or enantiomers thereof.

DETAILED DESCRIPTION OF THE INVENTION

Definitions

As used herein, the term "C$_{1-6}$alkyl" alone or in combination signifies a saturated, linear- or branched chain alkyl group containing 1 to 6, particularly 1 to 4 carbon atoms, for example methyl, ethyl, propyl, isopropyl, 1-butyl, 2-butyl, tert-butyl and the like. Particular "C$_{1-6}$alkyl" groups are methyl, ethyl, isopropyl and tert-butyl.

The term "C$_{3-7}$cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "C$_{3-7}$cycloalkyl" groups are cyclopropyl, cyclobutyl, cyclopentyl and cyclohexyl.

The term "C$_{1-6}$alkoxy" alone or in combination signifies a group C$_{1-6}$alkyl-O—, wherein the "C$_{1-6}$alkyl" is as defined above; for example methoxy, ethoxy, propoxy, iso-propoxy, n-butoxy, iso-butoxy, 2-butoxy, tert-butoxy, pentoxy, hexyloxy and the like. Particular "C$_{1-6}$alkoxy" groups are methoxy, ethoxy and propoxy.

The term "halogen" means fluorine, chlorine, bromine or iodine.

The term "haloC$_{1-6}$alkyl" denotes a C$_{1-6}$alkyl group wherein at least one of the hydrogen atoms of the C$_{1-6}$alkyl group has been replaced by same or different halogen atoms, particularly fluoro atoms. Examples of haloC$_{1-6}$alkyl include monofluoro-, difluoro- or trifluoro-methyl, -ethyl or -propyl, for example 3,3,3-trifluoropropyl, 3,3-difluoropropyl, 2-fluoroethyl, 2,2-difluoroethyl, 2,2,2-trifluoroethyl, fluoromethyl, difluoromethyl or trifluoromethyl. Particular "haloC$_{1-6}$alkyl" group is difluoromethyl or trifluoromethyl.

The term "haloC$_{1-6}$alkoxy" denotes a C$_{1-6}$alkoxy group wherein at least one of the hydrogen atoms of the C$_{1-6}$alkoxy group has been replaced by same or different halogen atoms, particularly fluoro atoms. Examples of haloC$_{1-6}$alkoxyl include monofluoro-, difluoro- or trifluoro-methoxy, -ethoxy or -propoxy, for example fluoropropoxy, difluoropropoxy, trifluoropropoxy, fluoroethoxy, difluoroethoxy, trifluoroethoxy, fluoromethoxy, difluoromethoxy or trifluoromethoxy. Particular "haloC$_{1-6}$alkoxy" group is 3-fluoropropoxy, 3,3-difluoropropoxy, 3,3,3-trifluoropropoxy, 2-fluoroethoxy, 2,2-difluoroethoxy, 2,2,2-trifluoroethoxy, fluoromethoxy, difluoromethoxy or trifluoromethoxy.

The term "cyano" alone or in combination refers to the group —CN.

The term "haloindazolyl" refers to an indazolyl group substituted once, twice or three times by halogen. Examples of haloindazolyl include, but not limited to, fluoroindazolyl, chloroindazolyl, bromoindazolyl, difluoroindazolyl, dichloroindazolyl, dibromoindazolyl, fluorochloroindazolyl, fluorobromoindazolyl, chlorobromoindazolyl, trifluoroindazolyl and difluorochloroindazolyl. Particular "haloindazolyl" group is fluorohaloindazolyl.

The term "halophenyl" refers to a phenyl group substituted once, twice or three times by halogen. Examples of halophenyl include, but not limited to, fluorophenyl, chlorophenyl, bromophenyl, difluorophenyl, dichlorophenyl, dibromophenyl, fluorochlorophenyl, fluorobromophenyl, chlorobromophenyl, trifluorophenyl and difluorochlorophenyl. Particular "halophenyl" group is fluorophenyl or chlorophenyl.

The term "enantiomer" denotes two stereoisomers of a compound which are non-superimposable mirror images of one another.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435. Particular are the sodium salts of the compounds of formula I.

Compounds of the general formula I which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Inhibitor of HBsAg

The present invention provides (i) a compound having the general formula I:

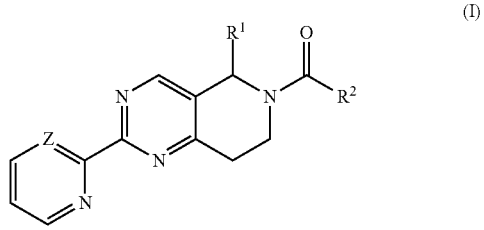

(I)

wherein
$R^1$ is $C_{1-6}$alkoxy, $C_{1-6}$alkyl, $C_{3-7}$cycloalkyl, halo$C_{1-6}$alkoxy, halo$C_{1-6}$alkyl or hydrogen;
$R^2$ is benzothiophenyl, imidazolyl, indazolyl, indolyl, isoxazolyl, oxazolyl, phenyl, pyridinyl, pyrimidinyl, thiazolyl or thiophenyl, wherein said benzothiophenyl, imidazolyl, indazolyl, indolyl, isoxazolyl, oxazolyl, phenyl, pyridinyl, thiazolyl or thiophenyl is unsubstituted or substituted by one, two or three substituents independently selected from $C_{1-6}$alkoxy, $C_{1-6}$alkoxy$C_{1-6}$alkoxy, $C_{1-6}$alkyl, $C_{3-7}$cycloalkyl, cyano, halo$C_{1-6}$alkoxy, halo$C_{1-6}$alkyl, halogen, hydroxy, hydroxy$C_{1-6}$alkoxy, hydroxy$C_{1-6}$alkyl, nitro and pheny$C_{1-6}$alkyl;
Z is CH or N;
or pharmaceutically acceptable salts, or enantiomers thereof.

A further embodiment of the present invention is (ii) a compound of formula I, wherein
$R^1$ is hydrogen or $C_{1-6}$alkyl;
$R^2$ is benzothiophenyl, imidazolyl, indazolyl, indolyl, isoxazolyl, oxazolyl, phenyl, pyridinyl, thiazolyl or thiophenyl, wherein said benzothiophenyl, imidazolyl, indazolyl, indolyl, isoxazolyl, oxazolyl, phenyl, pyridinyl, thiazolyl or thiophenyl is unsubstituted or substituted by one, two or three substituents independently selected from $C_{1-6}$alkoxy, $C_{1-6}$alkoxy$C_{1-6}$alkoxy, $C_{1-6}$alkyl, cyano, halo$C_{1-6}$alkyl, halogen, hydroxy, nitro and pheny$C_{1-6}$alkyl;
Z is CH or N
or pharmaceutically acceptable salts, or enantiomers thereof.

Another embodiment of the present invention is (iii) a compound of formula I, wherein,
$R^1$ is hydrogen, methyl or ethyl;
$R^2$ is benzothiophenyl, imidazolyl, indazolyl, indolyl, isoxazolyl, oxazolyl, phenyl, pyridinyl, thiazolyl or thiophenyl, wherein said benzothiophenyl, imidazolyl, indazolyl, indolyl, isoxazolyl, oxazolyl, phenyl, pyridinyl, thiazolyl or thiophenyl is unsubstituted or substituted by one, two or three substituents independently selected from ethoxy, methoxy, methoxyethoxy, methoxypropoxy, methyl, cyano, trifluoromethyl, bromo, chloro, fluoro, hydroxy, nitro and phenylmethyl;
Z is CH or N;
or pharmaceutically acceptable salts, or enantiomers thereof.

A further embodiment of the present invention is (iv) a compound of formula I, or pharmaceutically acceptable salts, or enantiomers thereof, wherein $R^1$ is $C_{1-6}$alkyl, and all remaining substituents have the significances given herein before.

A further embodiment of the present invention is (v) a compound of formula I, or pharmaceutically acceptable salts, or enantiomers thereof, wherein $R^1$ is methyl, and all remaining substituents have the significances given herein before.

Another further embodiment of the present invention is (vi) a compound of formula I, or pharmaceutically acceptable salts, or enantiomers thereof, wherein $R^2$ is indazolyl, phenyl, thiazolyl or thiophenyl, said indazolyl, phenyl, thiazolyl or thiophenyl is unsubstituted, or substituted by one or two substituents independently selected from $C_{1-6}$alkoxy, $C_{1-6}$alkoxy$C_{1-6}$alkoxy, $C_{1-6}$alkyl, halogen and phenyl$C_{1-6}$alkyl, and all remaining substituents have the significances given herein before.

Another further embodiment of the present invention is (vii) a compound of formula I, or pharmaceutically acceptable salts, or enantiomers thereof, wherein $R^2$ is indazolyl, phenyl, thiazolyl or thiophenyl, said indazolyl, phenyl, thiazolyl or thiophenyl is unsubstituted, or substituted by one or two substituents independently selected from methoxy, methoxypropoxy, methyl, chloro, fluoro and phenylmethyl; and all remaining substituents have the significances given herein before.

Another embodiment of the present invention is (viii) a compound of formula I, wherein
$R^1$ is $C_{1-6}$alkyl or hydrogen;
$R^2$ is indazolyl, $C_{1-6}$alkoxyindazolyl, haloindazolyl, (phenyl$C_{1-6}$alkyl)indazolyl, ($C_{1-6}$alkoxy$C_{1-6}$alkoxy)halophenyl, $C_{1-6}$alkoxy($C_{1-6}$alkoxy$C_{1-6}$alkoxy)phenyl, thiazolyl, C$_{1-6}$alkylthiazolyl, diC$_{1-6}$alkylthiazolyl, C$_{1-6}$alkoxythiophenyl or C$_{1-6}$alkylthiophenyl;

Z is CH or N;

or pharmaceutically acceptable salts, or enantiomers thereof.

A further embodiment of the present invention is (ix) a compound of formula I, wherein R$^1$ is methyl or hydrogen;

R$^2$ is indazolyl, methoxyindazolyl, fluoroindazolyl, (phenylmethyl)indazolyl, (methoxypropoxy)chlorophenyl, methoxy(methoxypropoxy)phenyl, thiazolyl, methylthiazolyl, dimethylthiazolyl, methoxythiophenyl or methylthiophenyl;

Z is CH or N;

or pharmaceutically acceptable salts, or enantiomers thereof.

Particular compounds of formula I according to the invention are the following:

[2-(2-pyridyl)-7,8-dihydro-5H-pyrido[4,3-d]pyrimidin-6-yl]-[4-(trifluoromethyl)phenyl]methanone;

4-[2-(2-pyridyl)-7,8-dihydro-5H-pyrido[4,3-d]pyrimidine-6-carbonyl]benzonitrile;

(4-nitrophenyl)-[2-(2-pyridyl)-7,8-dihydro-5H-pyrido[4,3-d]pyrimidin-6-yl]methanone;

phenyl-[2-(2-pyridyl)-7,8-dihydro-5H-pyrido[4,3-d]pyrimidin-6-yl]methanone;

(4-chlorophenyl)-[2-(2-pyridyl)-7,8-dihydro-5H-pyrido[4,3-d]pyrimidin-6-yl]methanone;

[2-(2-pyridyl)-7,8-dihydro-5H-pyrido[4,3-d]pyrimidin-6-yl]-[3-(trifluoromethyl)phenyl]methanone;

(3-fluoro-4-methoxy-phenyl)-[2-(2-pyridyl)-7,8-dihydro-5H-pyrido[4,3-d]pyrimidin-6-yl]methanone;

(4-fluorophenyl)-[2-(2-pyridyl)-7,8-dihydro-5H-pyrido[4,3-d]pyrimidin-6-yl]methanone;

(4-fluoro-3-methoxy-phenyl)-[2-(2-pyridyl)-7,8-dihydro-5H-pyrido[4,3-d]pyrimidin-6-yl]methanone;

(3,4-difluorophenyl)-[2-(2-pyridyl)-7,8-dihydro-5H-pyrido[4,3-d]pyrimidin-6-yl]methanone;

(4-fluoro-3-hydroxy-phenyl)-[2-(2-pyridyl)-7,8-dihydro-5H-pyrido[4,3-d]pyrimidin-6-yl]methanone;

(3-fluoro-4-hydroxy-phenyl)-[2-(2-pyridyl)-7,8-dihydro-5H-pyrido[4,3-d]pyrimidin-6-yl]methanone;

(4-ethoxy-3-fluoro-phenyl)-[2-(2-pyridyl)-7,8-dihydro-5H-pyrido[4,3-d]pyrimidin-6-yl]methanone;

[3-fluoro-4-(2-methoxyethoxy)phenyl]-[2-(2-pyridyl)-7,8-dihydro-5H-pyrido[4,3-d]pyrimidin-6-yl]methanone;

[3-fluoro-4-(3-methoxypropoxy)phenyl]-[2-(2-pyridyl)-7,8-dihydro-5H-pyrido[4,3-d]pyrimidin-6-yl]methanone;

[2-(2-pyridyl)-7,8-dihydro-5H-pyrido[4,3-d]pyrimidin-6-yl]-(3,4,5-trimethoxyphenyl)methanone;

(3,5-diethoxyphenyl)-[2-(2-pyridyl)-7,8-dihydro-5H-pyrido[4,3-d]pyrimidin-6-yl]methanone;

(3-chloro-5-methoxy-phenyl)-[2-(2-pyridyl)-7,8-dihydro-5H-pyrido[4,3-d]pyrimidin-6-yl]methanone;

(3,5-dimethoxyphenyl)-[2-(2-pyridyl)-7,8-dihydro-5H-pyrido[4,3-d]pyrimidin-6-yl]methanone;

(4-fluoro-3-methyl-phenyl)-[2-(2-pyridyl)-7,8-dihydro-5H-pyrido[4,3-d]pyrimidin-6-yl]methanone;

(3-chloro-4-methoxy-phenyl)-[2-(2-pyridyl)-7,8-dihydro-5H-pyrido[4,3-d]pyrimidin-6-yl]methanone;

(3,4-dimethoxyphenyl)-[2-(2-pyridyl)-7,8-dihydro-5H-pyrido[4,3-d]pyrimidin-6-yl]methanone;

(3-chloro-4-hydroxy-phenyl)-[2-(2-pyridyl)-7,8-dihydro-5H-pyrido[4,3-d]pyrimidin-6-yl]methanone;

[3-chloro-4-(3-methoxypropoxy)phenyl]-[2-(2-pyridyl)-7,8-dihydro-5H-pyrido[4,3-d]pyrimidin-6-yl]methanone;

(4-hydroxy-3-methoxy-phenyl)-[2-(2-pyridyl)-7,8-dihydro-5H-pyrido[4,3-d]pyrimidin-6-yl]methanone;

[3-methoxy-4-(3-methoxypropoxy)phenyl]-[2-(2-pyridyl)-7,8-dihydro-5H-pyrido[4,3-d]pyrimidin-6-yl]methanone;

(5-methyl-2-pyridyl)-[2-(2-pyridyl)-7,8-dihydro-5H-pyrido[4,3-d]pyrimidin-6-yl]methanone;

(3-fluoro-4-methyl-phenyl)-[2-(2-pyridyl)-7,8-dihydro-5H-pyrido[4,3-d]pyrimidin-6-yl]methanone;

(5-methoxy-2-pyridyl)-[2-(2-pyridyl)-7,8-dihydro-5H-pyrido[4,3-d]pyrimidin-6-yl]methanone;

(3,5-difluoro-4-methoxy-phenyl)-[2-(2-pyridyl)-7,8-dihydro-5H-pyrido[4,3-d]pyrimidin-6-yl]methanone;

(6-methyl-3-pyridyl)-[2-(2-pyridyl)-7,8-dihydro-5H-pyrido[4,3-d]pyrimidin-6-yl]methanone;

(4-methyl-2-thienyl)-[2-(2-pyridyl)-7,8-dihydro-5H-pyrido[4,3-d]pyrimidin-6-yl]methanone;

(5-methylisoxazol-3-yl)-[2-(2-pyridyl)-7,8-dihydro-5H-pyrido[4,3-d]pyrimidin-6-yl]methanone;

(3,4-dimethoxyphenyl)-[(5S)-5-methyl-2-(2-pyridyl)-7,8-dihydro-5H-pyrido[4,3-d]pyrimidin-6-yl]methanone;

(3,4-dimethoxyphenyl)-[(5S)-5-ethyl-2-(2-pyridyl)-7,8-dihydro-5H-pyrido[4,3-d]pyrimidin-6-yl]methanone;

(6-methoxy-3-pyridyl)-[2-(2-pyridyl)-7,8-dihydro-5H-pyrido[4,3-d]pyrimidin-6-yl]methanone;

(3,5-difluorophenyl)-[2-(2-pyridyl)-7,8-dihydro-5H-pyrido[4,3-d]pyrimidin-6-yl]methanone;

(3-fluoro-5-methoxy-phenyl)-[2-(2-pyridyl)-7,8-dihydro-5H-pyrido[4,3-d]pyrimidin-6-yl]methanone;

(4-methoxyphenyl)-[2-(2-pyridyl)-7,8-dihydro-5H-pyrido[4,3-d]pyrimidin-6-yl]methanone;

[3-chloro-4-(3-methoxypropoxy)phenyl]-(5-methyl-2-pyrimidin-2-yl-7,8-dihydro-5H-pyrido[4,3-d]pyrimidin-6-yl)methanone;

[5-methyl-2-(2-pyridyl)-7,8-dihydro-5H-pyrido[4,3-d]pyrimidin-6-yl]-(4-methyl-2-thienyl)methanone;

(5-chloro-2-thienyl)-[5-methyl-2-(2-pyridyl)-7,8-dihydro-5H-pyrido[4,3-d]pyrimidin-6-yl]methanone;

[5-methyl-2-(2-pyridyl)-7,8-dihydro-5H-pyrido[4,3-d]pyrimidin-6-yl]-(5-methyl-2-thienyl)methanone;

[5-methyl-2-(2-pyridyl)-7,8-dihydro-5H-pyrido[4,3-d]pyrimidin-6-yl]-(3-thienyl)methanone;

(4-methyloxazol-5-yl)-[5-methyl-2-(2-pyridyl)-7,8-dihydro-5H-pyrido[4,3-d]pyrimidin-6-yl]methanone;

1H-indol-6-yl-[5-methyl-2-(2-pyridyl)-7,8-dihydro-5H-pyrido[4,3-d]pyrimidin-6-yl]methanone;

1H-indazol-5-yl-[5-methyl-2-(2-pyridyl)-7,8-dihydro-5H-pyrido[4,3-d]pyrimidin-6-yl]methanone;

benzothiophen-2-yl-[5-methyl-2-(2-pyridyl)-7,8-dihydro-5H-pyrido[4,3-d]pyrimidin-6-yl]methanone;

[5-methyl-2-(2-pyridyl)-7,8-dihydro-5H-pyrido[4,3-d]pyrimidin-6-yl]-(2-thienyl)methanone;

[5-methyl-2-(2-pyridyl)-7,8-dihydro-5H-pyrido[4,3-d]pyrimidin-6-yl]-(3-methyl-2-thienyl)methanone;

[5-methyl-2-(2-pyridyl)-7,8-dihydro-5H-pyrido[4,3-d]pyrimidin-6-yl]-thiazol-2-yl-methanone;

[5-methyl-2-(2-pyridyl)-7,8-dihydro-5H-pyrido[4,3-d]pyrimidin-6-yl]-(2-methylthiazol-5-yl)methanone;

(5-bromo-2-thienyl)-[5-methyl-2-(2-pyridyl)-7,8-dihydro-5H-pyrido[4,3-d]pyrimidin-6-yl]methanone;

[5-methyl-2-(2-pyridyl)-7,8-dihydro-5H-pyrido[4,3-d]pyrimidin-6-yl]-thiazol-5-yl-methanone;

[5-methyl-2-(2-pyridyl)-7,8-dihydro-5H-pyrido[4,3-d]pyrimidin-6-yl]-(5-methylthiazol-2-yl)methanone;

1H-imidazol-2-yl-[5-methyl-2-(2-pyridyl)-7,8-dihydro-5H-pyrido[4,3-d]pyrimidin-6-yl]methanone;

(1-methylimidazol-2-yl)-[5-methyl-2-(2-pyridyl)-7,8-dihydro-5H-pyrido[4,3-d]pyrimidin-6-yl]methanone;

(5-methoxy-2-thienyl)-[5-methyl-2-(2-pyridyl)-7,8-dihydro-5H-pyrido[4,3-d]pyrimidin-6-yl]methanone;

[5-methyl-2-(2-pyridyl)-7,8-dihydro-5H-pyrido[4,3-d]pyrimidin-6-yl]-[4-(trifluoromethyl)thiazol-2-yl]methanone;

[5-methyl-2-(2-pyridyl)-7,8-dihydro-5H-pyrido[4,3-d]pyrimidin-6-yl]-oxazol-2-yl-methanone;

(4,5-dimethylthiazol-2-yl)-[5-methyl-2-(2-pyridyl)-7,8-dihydro-5H-pyrido[4,3-d]pyrimidin-6-yl]methanone;

(1-methylindazol-3-yl)-(5-methyl-2-pyrimidin-2-yl-7,8-dihydro-5H-pyrido[4,3-d]pyrimidin-6-yl)methanone;

1H-indazol-3-yl-(5-methyl-2-pyrimidin-2-yl-7,8-dihydro-5H-pyrido[4,3-d]pyrimidin-6-yl)methanone;

(5-fluoro-1H-indazol-3-yl)-(5-methyl-2-pyrimidin-2-yl-7,8-dihydro-5H-pyrido[4,3-d]pyrimidin-6-yl)methanone;

(1-benzylindazol-3-yl)-(5-methyl-2-pyrimidin-2-yl-7,8-dihydro-5H-pyrido[4,3-d]pyrimidin-6-yl)methanone; and (5-methoxy-1H-indazol-3-yl)-(5-methyl-2-pyrimidin-2-yl-7,8-dihydro-5H-pyrido[4,3-d]pyrimidin-6-yl)methanone;

or pharmaceutically acceptable salts, or enantiomers thereof.

More particularly, the invention relates to the following compounds of formula I:

[3-methoxy-4-(3-methoxypropoxy)phenyl]-[2-(2-pyridyl)-7,8-dihydro-5H-pyrido[4,3-d]pyrimidin-6-yl]methanone;

[3-chloro-4-(3-methoxypropoxy)phenyl]-(5-methyl-2-pyrimidin-2-yl-7,8-dihydro-5H-pyrido[4,3-d]pyrimidin-6-yl)methanone;

[5-methyl-2-(2-pyridyl)-7,8-dihydro-5H-pyrido[4,3-d]pyrimidin-6-yl]-(4-methyl-2-thienyl)methanone;

[5-methyl-2-(2-pyridyl)-7,8-dihydro-5H-pyrido[4,3-d]pyrimidin-6-yl]-(5-methyl-2-thienyl)methanone;

[5-methyl-2-(2-pyridyl)-7,8-dihydro-5H-pyrido[4,3-d]pyrimidin-6-yl]-thiazol-2-yl-methanone;

[5-methyl-2-(2-pyridyl)-7,8-dihydro-5H-pyrido[4,3-d]pyrimidin-6-yl]-(5-methylthiazol-2-yl)methanone;

(5-methoxy-2-thienyl)-[5-methyl-2-(2-pyridyl)-7,8-dihydro-5H-pyrido[4,3-d]pyrimidin-6-yl]methanone;

(4,5-dimethylthiazol-2-yl)-[5-methyl-2-(2-pyridyl)-7,8-dihydro-5H-pyrido[4,3-d]pyrimidin-6-yl]methanone;

1H-indazol-3-yl-(5-methyl-2-pyrimidin-2-yl-7,8-dihydro-5H-pyrido[4,3-d]pyrimidin-6-yl)methanone;

(5-fluoro-1H-indazol-3-yl)-(5-methyl-2-pyrimidin-2-yl-7,8-dihydro-5H-pyrido[4,3-d]pyrimidin-6-yl)methanone;

(1-benzylindazol-3-yl)-(5-methyl-2-pyrimidin-2-yl-7,8-dihydro-5H-pyrido[4,3-d]pyrimidin-6-yl)methanone; and (5-methoxy-1H-indazol-3-yl)-(5-methyl-2-pyrimidin-2-yl-7,8-dihydro-5H-pyrido[4,3-d]pyrimidin-6-yl)methanone;

or pharmaceutically acceptable salts, or enantiomers thereof.

Synthesis

The compounds of the present invention can be prepared by any conventional means. Suitable processes for synthesizing these compounds as well as their starting materials are provided in the schemes below and in the examples. All substituents, in particular, $R^1$, $R^2$ and Z are as defined above unless otherwise indicated. Furthermore, and unless explicitly otherwise stated, all reactions, reaction conditions, abbreviations and symbols have the meanings well known to a person of ordinary skill in organic chemistry.

General Synthetic Route for Compound I (Scheme 1)

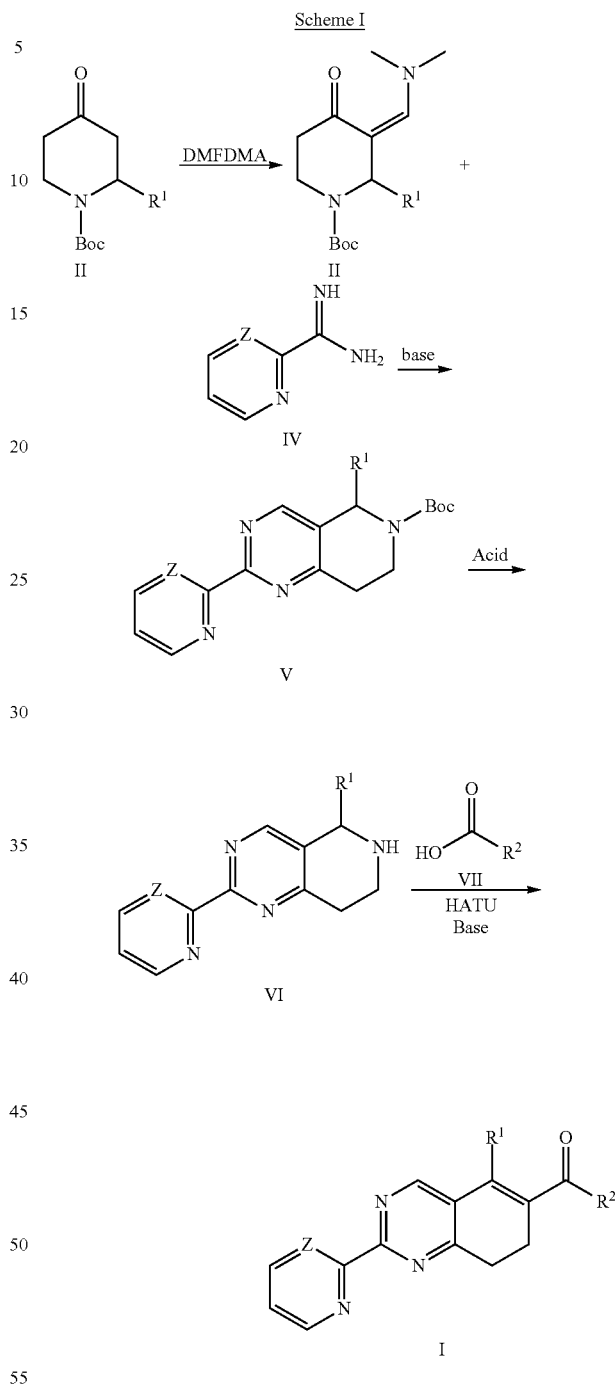

The compound of formula I can be prepared according to Scheme 1.

Compound II is heated with DMFDMA in a suitable solvent such as CAN, DMF to generate intermediate III. Coupling of Intermediate III with compound IV in the presence of a base such as sodium methoxide, potassium carbonate, or sodium bicarbonate produces compound V. Deprotection of Boc group under acidic condition produces compound VI. Coupling of compound VI with acid VII in the presence of HATU and a base such as DIPEA or TEA affords compound I.

This invention also relates to a process for the preparation of a compound of formula I comprising one of the following steps:
(a) coupling of a compound of formula (A)

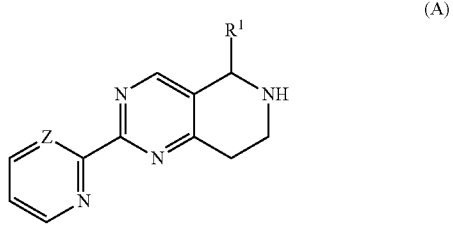

(A)

with a compound of formula (B)

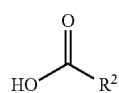

(B)

in the presence of a coupling reagent and a base;
wherein $R^1$, $R^2$ and Z are defined as above. In step (a), the coupling reagent can be for example HATU, the base can be for example DIPEA or TEA.

A compound of formula I when manufactured according to the above process is also an object of the invention.

Compounds of this invention also show good safety and PK profile.

Pharmaceutical Compositions and Administration

The invention also relates to a compound of formula I for use as therapeutically active substance.

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit HBsAg. For example, such amount may be below the amount that is toxic to normal cells, or the mammal as a whole.

In one example, the pharmaceutically effective amount of the compound of the invention administered parenterally per dose will be in the range of about 0.01 to 100 mg/kg, alternatively about 0.01 to 100 mg/kg of patient body weight per day, with the typical initial range of compound used being 0.3 to 15 mg/kg/day. In another embodiment, oral unit dosage forms, such as tablets and capsules, preferably contain from about 0.1 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 0.1 to 1000 mg of the compound of the invention compounded with about 0 to 2000 mg anhydrous lactose, about 0 to 2000 mg sodium croscarmellose, about 0 to 2000 mg polyvinylpyrrolidone (PVP) K30, and about 0 to 2000 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 0.1 to 1000 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula I, or a stereoisomer or pharmaceutically acceptable salt thereof. In a further embodiment includes a pharmaceutical composition comprising a compound of Formula I, or a stereoisomer or pharmaceutically acceptable salt thereof, together with a pharmaceutically acceptable carrier or excipient.

The following example A and B illustrate typical compositions of the present invention, but serve merely as representative thereof.

Example A

A compound of formula I can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula I can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

Indications and Methods of Treatment

The compounds of the invention can inhibit HBsAg production or secretion and inhibit HBV gene expression. Accordingly, the compounds of the invention are useful for the treatment or prophylaxis of HBV infection.

The invention relates to the use of a compound of formula I for the inhibition of HBsAg production or secretion.

The invention relates to the use of a compound of formula I for the inhibition of HBV DNA production.

The invention relates to the use of a compound of formula I for the inhibition of HBV gene expression.

The invention relates to the use of a compound of formula I for the treatment or prophylaxis of HBV infection.

The use of a compound of formula I for the preparation of medicaments useful in the treatment or prophylaxis diseases that are related to HBV infection is an object of the invention.

The invention relates in particular to the use of a compound of formula I for the preparation of a medicament for the treatment or prophylaxis of HBV infection.

Another embodiment includes a method for the treatment or prophylaxis of HBV infection, which method comprises administering an effective amount of a compound of Formula I, a stereoisomer, tautomer, prodrug, conjugates or pharmaceutically acceptable salt thereof.

EXAMPLES

The invention will be more fully understood by reference to the following examples. They should not, however, be construed as limiting the scope of the invention.
Abbreviations used herein are as follows:
μL: microliter
μm: micrometer
μM: micromoles per liter
$IC_{50}$: the half maximal inhibitory concentration
LC/MS: liquid chromatography/mass spectrometry
M: molarity
MHz: megahertz
min: minute
hr(s): hour(s)
mM: millimoles per liter
MS (ESI): mass spectroscopy (electron spray ionization)
NMR: nuclear magnetic resonance
obsd. observed
rt: room temperature
Pd/C: palladium on activated carbon
δ: chemical shift
HATH: 1-[Bis(dimethylamino)methylene]-1H-1,2,3-triazolo[4,5-b]pyridinium 3-oxid hexafluorophosphate
DIPEA: A, A-diisopropylamine
MTBE: methyl tert-butyl ether
DMFDMA N,N-Dimethylformamide dimethyl acetal
CAN Ceric ammonium nitrate
DMF N,N-Dimethylformamide
FA Ethyl acetate General Experimental Conditions Intermediates and final compounds were purified by flash chromatography using one of the following instruments: i) Biotage SP1 system and the Quad 12/25 Cartridge module, ii) ISCO combi-flash chromatography instrument. Silica gel Brand and pore size: i) KP-SIL 60 Å, particle size: 40-60 μm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp Cm (5 μm, OBD™ 30×100 mm) column or SunFire™ Perp $C_{18}$ (5 μm, OBD™ 30×100 mm) column.

Chiral Separation was conducted on Thar 350 preparative SFC using ChiralPak AD-10u (200×50 mm I.D.) with mobile phase A for $CO_2$ and B for ethanol.

LC/MS spectra were obtained using an Acquity Ultra Performance LC—3100 Mass Detector or Acquity Ultra Performance LC—SQ Detector. Standard LC/MS conditions were as follows (running time 3 minutes):

Acidic condition: A: 0.1% formic acid in $H_2O$; B: 0.1% formic acid in acetonitrile;

Basic condition: A: 0.05% $NH_3H_2O$ in $H_2O$; B: acetonitrile;

Neutral condition: A: $H_2O$; B: acetonitrile.

Mass spectra (MS): generally only ions which indicate the parent mass are reported, and unless otherwise stated the mass ion quoted is the positive mass ion $(M+H)^+$.

The microwave assisted reactions were carried out in a Biotage Initiator Sixty or CEM Discover.

NMR Spectra were obtained using Bruker A vance 400 MHz.

All reactions involving air-sensitive reagents were performed under an argon atmosphere. Reagents were used as received from commercial suppliers without further purification unless otherwise noted.

PREPARATIVE EXAMPLES

Example 1

[2-(2-Pyridyl)-7,8-dihydro-5H-pyrido[4,3-d]pyrimidin-6-yl]-[4-(trifluoromethyl)phenyl]methanone

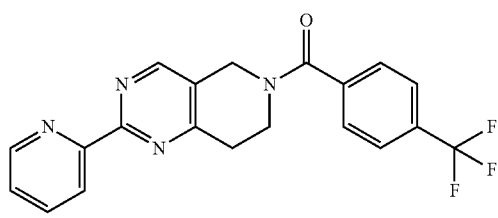 [SMILES: O=C(c1ccc(C(F)(F)F)cc1)N1CCc2nc(-c3ccccn3)ncc2C1]

Step 1: Preparation of Tert-Butyl 3-(dimethylaminomethylene)-4-oxo-piperidine-1-carboxylate

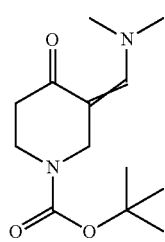 [SMILES: CN(C)C=C1CN(C(=O)OC(C)(C)C)CCC1=O]

A mixture of tert-butyl 4-oxopiperidine-1-carboxylate (15.0 g, 0.075 mol) and DMFDMA (9.87 g, 0.0829 mol) in DMF (100 mL) was heated at 90° C. with stirring overnight. The resulting mixture was then concentrated in vacuo and diluted with water (100 mL). The resulting mixture was extracted with EA (30 mL) for three times. The combined organic layer was washed with water, dried over anhydrous Na$_2$SO$_4$ and concentrated in vacuo to give the crude tert-butyl 3-(dimethylaminomethylene)-4-oxo-piperidine-1-carboxylate (13 g) as yellow oil, which was used in the next step directly.

Step 2: Preparation of Tert-Butyl 2-(2-pyridyl)-7,8-dihydro-5H-pyrido[4,3-d]pyrimidine-6-carboxylate

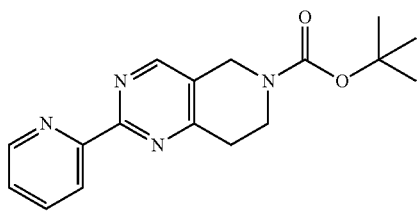 [SMILES: CC(C)(C)OC(=O)N1CCc2nc(-c3ccccn3)ncc2C1]

A mixture of tert-butyl 3-(dimethylaminomethylene)-4-oxo-piperidine-1-carboxylate (10 g, 39.37 mmol), pyridine-2-carboxamidine hydrochloride (6.2 g, 39.37 mmol) and CFLONa (4.25 g, 78.74 mmol) in ethanol (100 mL) was heated at 100° C. with stirring overnight. The resulting mixture was concentrated in vacuo and the residue was dissolved in EA. The resulting solution was washed with water, dried over anhydrous Na$_2$SO$_4$ and concentrated in vacuo to give the crude tert-butyl 2-(2-pyridyl)-7,8-dihydro-5H-pyrido[4,3-d]pyrimidine-6-carboxylate as an orange oil (12 g) as yellow solid, which was used in the next step directly without any further purification.

Step 3: Preparation of 2-(2-pyridyl)-5,6,7,8-tetrahydropyrido[4,3-d]pyrimidine

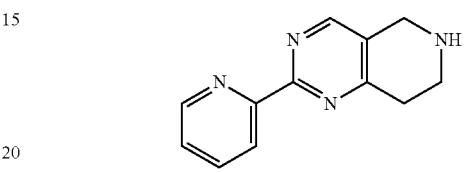

A mixture of tert-butyl 2-(2-pyridyl)-7,8-dihydro-5H-pyrido[4,3-d]pyrimidine-6-carboxylate (9 g, 28.85 mmol) and hydrogen chloride in 1,4-dioxane solution (4 M, 15 mL) was stirred for 3 h at rt. The resulting mixture was concentrated in vacuo to give crude 2-(2-pyridyl)-5,6,7,8-tetrahydropyrido[4,3-d]pyrimidine hydrochloride (9 g) as yellow solid, which was used in the next step directly without any further purification.

Step 4: Preparation of [2-(2-pyridyl)-7,8-dihydro-5H-pyrido[4,3-d]pyrimidin-6-yl]-[4-(trifluoromethyl)phenyl]methanone

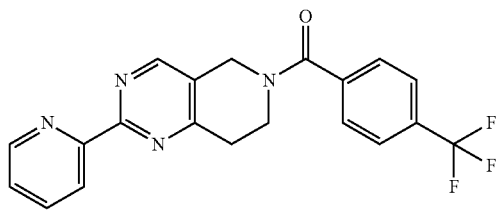 [SMILES: O=C(c1ccc(C(F)(F)F)cc1)N1CCc2nc(-c3ccccn3)ncc2C1]

A mixture of 2-(2-pyridyl)-5,6,7,8-tetrahydropyrido[4,3-d]pyrimidine hydrochloride (100 mg, 0.405 mmol), 4-(trifluoromethyl)benzoic acid (115 mg, 0.607 mmol), HATU (308 mg, 0.81 mmol) and DIPEA (262 mg, 2.02 mmol) in DMF (5 mL) was stirred at rt overnight. The resulting mixture was poured into water (5 mL) and extracted with EA (20 mL) for three times. The combined organic layer was concentrated in vacuo and the residue was purified by prep-HPLC to give [2-(2-pyridyl)-7,8-dihydro-577-pyrido[4,3-d]pyrimidin-6-yl]-[4-(trifluoromethyl)phenyl]methanone (15 mg) as light yellow solid. $^1$H NMR (400 MHz, CDCl$_3$) δ: 8.67-8.97 (m, 2H), 8.54 (d, 1H), 7.91 (td, 1H), 7.73-7.82 (m, 2H), 7.62 (d, 2H), 7.40-7.53 (m, 1H), 4.53-5.13 (m, 2H), 3.68-4.30 (m, 2H), 3.01-3.42 (m, 2H). MS obsd. (ESI$^+$) [(M+H)$^+$]: 385.

Example 2

4-[2-(2-Pyridyl)-7,8-dihydro-5H-pyrido[4,3-d]pyrimidine-6-carbonyl]benzonitrile

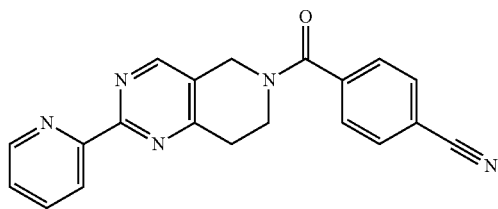 [SMILES: N#Cc1ccc(C(=O)N2CCc3nc(-c4ccccn4)ncc3C2)cc1]

A mixture of 2-(2-pyridyl)-5,6,7,8-tetrahydropyrido[4,3-d]pyrimidine hydrochoride (100 mg, 0.405 mmol, the product of step 3 in Example 1), 4-cyano-benzoic acid (89 mg, 0.607 mmol), HATU (308 mg, 0.81 mmol) and DIPEA (262 mg, 2.02 mmol) in DMF (5 mL) was stirred at rt overnight. The resulting mixture was poured into water (5 mL) and extracted with EA (10 mL) for three times. The combined organic layer was concentrated in vacuo and the residue was purified by prep-HPLC to give 4-(2-pyridin-2-yl-7,8-dihydro-5H-pyrido[4,3-d]pyrimidine-6-carbonyl)-benzonitrile (15 mg) as light yellow solid. $^1$H NMR (400 MHz, Methanol-d4) δ: 8.89 (br. s., 1H), 8.79 (d, 1H), 8.67 (d, 1H), 8.21 (t, 1H), 7.91 (d, 2H), 7.67-7.77 (m, 3H), 5.00-5.12 (m, 1H), 4.77 (br. s., 1H), 4.18 (br. s., 1H), 3.72-3.92 (m, 1H), 3.02-3.29 (m, 2H). MS obsd. (ESI$^+$) [(M+H)$^+$]: 342.

Example 3

(4-Nitrophenyl)-[2-(2-pyridyl)-7,8-dihydro-5H-pyrido[4,3-d]pyrimidin-6-yl]methanone

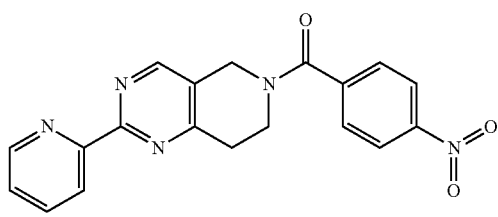 [SMILES: O=C(c1ccc([N+](=O)[O-])cc1)N1CCc2nc(-c3ccccn3)ncc2C1]

A mixture of 2-(2-pyridyl)-5,6,7,8-tetrahydropyrido[4,3-d]pyrimidine hydrochloride (150 mg, 0.607 mmol, the product of step 3 in Example 1), 4-nitrobenzoic acid (203 mg, 1.21 mmol), HATU (461 mg, 1.214 mmol) and DIPEA (392 mg, 3.036 mmol) in DMF (5 mL) was stirred at rt overnight. The resulting mixture was poured into water (5 mL) and extracted with EA (20 mL) for three times. The combined organic layer was concentrated in vacuo and the residue was purified by Prep-HPLC to give (4-nitrophenyl)-[2-(2-pyridyl)-7,8-dihydro-5H-pyrido[4,3-d]pyrimidin-6-yl]methanone (17 mg) as light yellow solid. $^1$H NMR (400 MHz, DMSO-d6) δ: 8.87-8.97 (m, 1H), 8.70-8.79 (m, 1H), 8.29-8.43 (m, 3H), 7.97 (t, 1H), 7.82 (d, 2H), 7.53 (dd, 1H), 4.95 (br. s., 1H), 4.67 (br. s., 1H), 4.06 (br. s., 1H), 3.67 (br. s., 1H), 3.07 (br. s., 2H). MS obsd. (ESI$^+$) [(M+H)$^+$]: 362.

Example 4

Phenyl-[2-(2-pyridyl)-7,8-dihydro-5H-pyrido[4,3-d]pyrimidin-6-yl]methanone

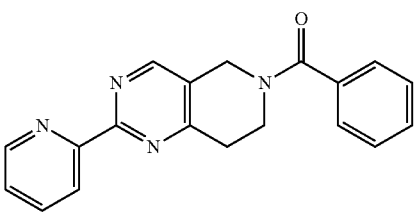 [SMILES: O=C(c1ccccc1)N1CCc2nc(-c3ccccn3)ncc2C1]

A mixture of 2-(2-pyridyl)-5,6,7,8-tetrahydropyrido[4,3-d]pyrimidine hydrochloride (200 mg, 0.943 mmol, the product of step 3 in Example 1), benzoic acid (230 mg, 1.887 mmol), HATU (717 mg, 1.887 mmol) and DIPEA (610 mg, 4.717 mmol) in DMF (5 mL) was stirred at rt overnight. The resulting mixture was poured into water (5 mL) and extracted with EA (20 mL) for three times. The combined organic layer was concentrated in vacuo and the residue was purified by prep-HPLC to give phenyl-[2-(2-pyridyl)-7,8-dihydro-5H-pyrido[4,3-d]pyrimidin-6-yl]methanone (190 mg). $^1$H NMR (400 MHz, CDCl$_3$) δ: 8.84 (d, 1H), 8.72 (br. s., 1H), 8.50 (d, 1H), 7.87 (td, 1H), 7.39-7.51 (m, 6H), 4.97 (br. s., 2H), 3.83 (br. s., 2H), 3.19 (br. s., 2H). MS obsd. (ESI$^+$) [(M+H)$^+$]: 317.

Example 5

(4-Chlorophenyl)-[2-(2-pyridyl)-7,8-dihydro-5H-pyrido[4,3-d]pyrimidin-6-yl]methanone

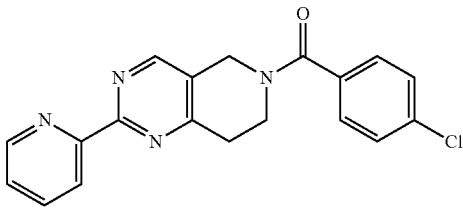 [SMILES: O=C(c1ccc(Cl)cc1)N1CCc2nc(-c3ccccn3)ncc2C1]

A mixture of 2-(2-pyridyl)-5,6,7,8-tetrahydropyrido[4,3-d]pyrimidine hydrochloride (200 mg, 0.943 mmol, the product of step 3 in Example 1), 4-chlorobenzoic acid (294 mg, 1.887 mmol), HATU (717 mg, 1.887 mmol) and DIPEA (610 mg, 4.717 mmol) in DMF (5 mL) was stirred at rt overnight. The resulting mixture was poured into water (5 mL) and extracted with EA (20 mL) for three times. The combined organic layer was concentrated in vacuo and the residue was purified by prep-HPLC to give (4-chlorophenyl)-[2-(2-pyridyl)-7,8-dihydro-5H-pyrido[4,3-d]pyrimidin-6-yl]methanone (63 mg) as light yellow solid. $^1$H NMR (400 MHz, CDCl$_3$) δ: 8.78-8.92 (m, 1H), 8.71 (br. s., 1H), 8.51 (d, 1H), 7.88 (td, 1.8 Hz, 1H), 7.40-7.48 (m, 5H), 4.61-5.08 (m, 2H), 3.86 (br. s., 2H), 3.20 (br. s., 2H). MS obsd. (ESI$^+$) [(M+H)$^+$]: 351.

Example 6

[2-(2-Pyridyl)-7,8-dihydro-5H-pyrido[4,3-d]pyrimidin-6-yl]-[3-(trifluoromethyl)phenyl]methanone

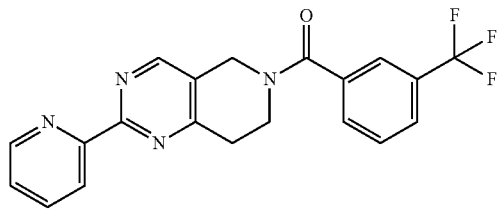 [SMILES: O=C(c1cccc(C(F)(F)F)c1)N1CCc2nc(-c3ccccn3)ncc2C1]

A mixture of 2-(2-pyridyl)-5,6,7,8-tetrahydropyrido[4,3-d]pyrimidine hydrochloride (200 mg, 0.943 mmol, the product of step 3 in Example 1), 3-(trifluoromethyl)benzoic acid (359 mg, 1.887 mmol), HATU (717 mg, 1.887 mmol) and DIPEA (610 mg, 4.717 mmol) in DMF (5 mL) was stirred at rt overnight. The resulting mixture was poured into water (5 mL) and extracted with EA (20 mL) for three times. The combined organic layer was concentrated in vacuo and the residue was purified by prep-HPLC to give [2-(2-pyridyl)-7,8-dihydro-5H-pyrido[4,3-d]pyrimidin-6-yl]-[3-(trifluoromethyl)phenyl]methanone (100 mg) as light yellow solid. $^1$H NMR (400 MHz, CDCl$_3$) δ: 8.86 (d, 1H), 8.64-8.80 (m, 1H), 8.58 (d, 1H), 7.91-8.04 (m, 1H), 7.73-7.80 (m, 2H), 7.59-7.71 (m, 2H), 7.52 (dd, 1H), 4.57-5.11 (m, 2H), 3.74-4.20 (m, 2H), 2.97-3.32 (m, 2H). MS obsd. (ESI$^+$) [(M+H)$^+$]: 385.

Example 7

(3-Fluoro-4-methoxy-phenyl)-[2-(2-pyridyl)-7,8-dihydro-5H-pyrido[4,3-d]pyrimidin-6-yl]methanone

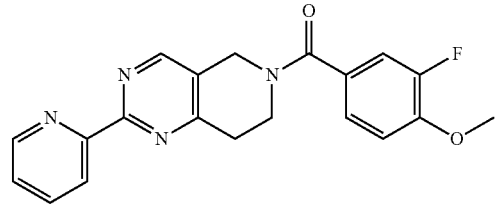

A mixture of 2-(2-pyridyl)-5,6,7,8-tetrahydropyrido[4,3-d]pyrimidine hydrochloride (150 mg, 0.46 mmol, the product of step 3 in Example 1), 3-fluoro-4-methoxy-benzoic acid (156 mg, 0.92 mmol), HATU (350 mg, 0.92 mmol) and DIPEA (297 mg, 2.3 mmol) in DMF (5 mL) was stirred at rt overnight. The resulting mixture was poured into water (5 mL) and extracted with EA (20 mL) for three times. The combined organic layer was concentrated in vacuo and the residue was purified by prep-HPLC to give (3-fluoro-4-methoxy-phenyl)-[2-(2-pyridyl)-7,8-dihydro-5H-pyrido[4,3-d]pyrimidin-6-yl]methanone (13 mg) as light yellow solid. $^1$H NMR (400 MHz, CDCl$_3$) δ: 8.88 (d, 1H), 8.68 (br. s., 1H), 8.53 (d, 1H), 7.91 (td, 1.8 Hz, 1H), 7.40-7.51 (m, 1H), 7.22-7.35 (m, 2H), 6.97-7.12 (m, 1H), 4.90 (br. s., 2H), 3.85-4.06 (m, 5H), 3.22 (t, 2H). MS obsd. (ESI$^+$) [(M+H)$^+$]: 365.

Example 8

(4-Fluorophenyl)-[2-(2-pyridyl)-7,8-dihydro-5H-pyrido[4,3-d]pyrimidin-6-yl]methanone

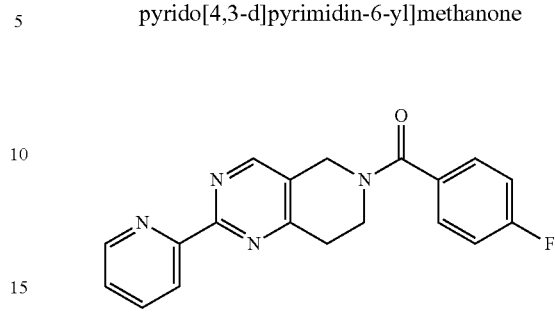

A mixture of 2-(2-pyridyl)-5,6,7,8-tetrahydropyrido[4,3-d]pyrimidine hydrochloride (150 mg, 0.46 mmol, the product of step 3 in Example 1), 4-fluorobenzoic acid (129 mg, 0.92 mmol), HATU (350 mg, 0.92 mmol) and DIPEA (297 mg, 2.3 mmol) in DMF (5 mL) was stirred overnight. The resulting mixture was poured into water (5 mL) and extracted with EA (20 mL) for three times. The combined organic layer was concentrated in vacuo and the residue was purified by prep-HPLC to give (4-fluorophenyl)-[2-(2-pyridyl)-7,8-dihydro-5H-pyrido[4,3-d]pyrimidin-6-yl]methanone (15 mg) as light yellow solid. $^1$H NMR (400 MHz, CDCl$_3$) δ: 8.81-8.91 (m, 1H), 8.58-8.78 (m, 1H), 8.52 (d, 1H), 7.89 (td, 1H), 7.47-7.55 (m, 2H), 7.40-7.46 (m, 1H), 7.17 (t, 2H), 4.90 (br. s., 2H), 3.90 (br. s., 2H), 3.20 (br. s., 2H). MS obsd. (ESI$^+$) [(M+H)$^+$]: 335.

Example 9

(4-Fluoro-3-methoxy-phenyl)-[2-(2-pyridyl)-7,8-dihydro-5H-pyrido[4,3-d]pyrimidin-6-yl]methanone

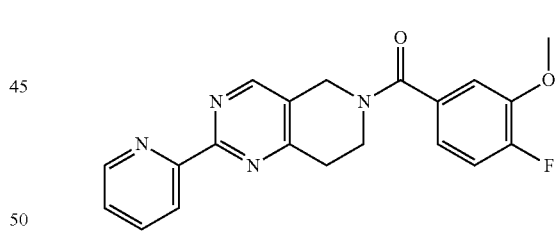

A mixture of 2-(2-pyridyl)-5,6,7,8-tetrahydropyrido[4,3-d]pyrimidine hydrochloride (150 mg, 0.46 mmol, the product of step 3 in Example 1), 4-fluoro-3-methoxy-benzoic acid (156 mg, 0.92 mmol), HATU (350 mg, 0.92 mmol) and DIPEA (297 mg, 2.3 mmol) in DMF (5 mL) was stirred at rt overnight. The resulting mixture was poured into water (5 mL) and extracted with EA (20 mL) for three times. The combined organic layer was concentrated in vacuo and the residue was purified by prep-HPLC to give (4-fluoro-3-methoxy-phenyl)-[2-(2-pyridyl)-7,8-dihydro-5H-pyrido[4,3-d]pyrimidin-6-yl]methanone (40 mg) as light yellow solid. $^1$H NMR (400 MHz, Methanol-d4) δ: 8.74 (d, 2H), 8.52 (d, 1H), 8.00 (td, 1H), 7.55 (ddd, 1H), 7.18-7.34 (m, 2H), 7.11 (ddd, 1H), 4.95 (br. s., 2H), 3.71-4.23 (m, 5H), 3.18 (br. s., 2H). MS obsd. (ESI$^+$) [(M+H)$^+$]: 365.

Example 10

(3,4-Difluorophenyl)-[2-(2-pyridyl)-7,8-dihydro-5H-pyrido[4,3-d]pyrimidin-6-yl]methanone

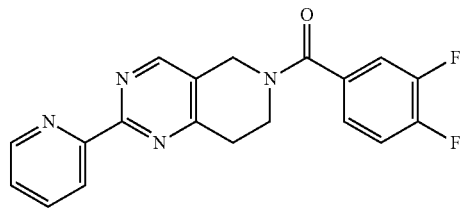 [SMILES: O=C(c1ccc(F)c(F)c1)N1CCc2nc(-c3ccccn3)ncc2C1]

A mixture of 2-(2-pyridyl)-5,6,7,8-tetrahydropyrido[4,3-d]pyrimidine hydrochloride (150 mg, 0.46 mmol, the product of step 3 in Example 1), 3,4-difluorobenzoic acid (145 mg, 0.92 mmol), HATU (350 mg, 0.92 mmol) and DIPEA (297 mg, 2.3 mmol) in DMF (5 mL) was stirred at rt overnight. The resulting mixture was poured into water (5 mL) and extracted with EA (20 mL) for three times. The combined organic layer was concentrated in vacuo and the residue was purified by prep-HPLC to give (3,4-difluorophenyl)-[2-(2-pyridyl)-7,8-dihydro-5H-pyrido[4,3-d]pyrimidin-6-yl]methanone (60 mg) as light yellow solid. $^1$H NMR (400 MHz, Methanol-d4) δ: 8.65-8.88 (m, 2H), 8.55 (d, 1H), 8.03 (td, 1H), 7.50-7.62 (m, 2H), 7.32-7.49 (m, 2H), 4.97 (br. s., 2H), 3.72-4.26 (m, 2H), 3.19 (t, 2H). MS obsd. (ESI$^+$) [(M+H)$^+$]: 353.

Example 11

(4-Fluoro-3-hydroxy-phenyl)-[2-(2-pyridyl)-7,8-dihydro-5H-pyrido[4,3-d]pyrimidin-6-yl]methanone

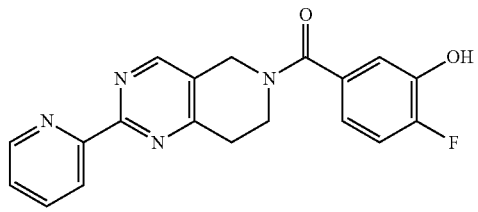 [SMILES: O=C(c1ccc(F)c(O)c1)N1CCc2nc(-c3ccccn3)ncc2C1]

A mixture of 2-(2-pyridyl)-5,6,7,8-tetrahydropyrido[4,3-d]pyrimidine hydrochloride (1 g, 3.067 mmol, the product of step 3 in Example 1), 4-fluoro-3-hydroxy-benzoic acid (0.718 g, 4.6 mmol), HATU (2.33 g, 6.13 mmol) and DIPEA (1.98 g, 15.34 mmol) in DMF (5 mL) was stirred at rt overnight. The resulting mixture was poured into water (5 mL) and extracted with EA (50 mL) for three times. The combined organic layer was concentrated in vacuo and the residue was purified by prep-HPLC to (4-fluoro-3-hydroxy-phenyl)-[2-(2-pyridyl)-7,8-dihydro-5H-pyrido[4,3-d]pyrimidin-6-yl]methanone (18 mg) as light yellow solid. $^1$H NMR (400 MHz, Methanol-d4) δ: 8.69-8.94 (m, 2H), 8.44-8.61 (m, 1H), 8.02 (td, 1H), 7.56 (dd, 1H), 7.19 (dd, 1H), 7.08 (d, 1H), 6.98 (d, 1H), 4.93-5.11 (m, 2H), 3.83-4.16 (m, 2H), 3.18 (br. s., 2H). MS obsd. (ESI$^+$) [(M+H)$^+$]: 351.

Example 12

(3-Fluoro-4-hydroxy-phenyl)-[2-(2-pyridyl)-7,8-dihydro-5H-pyrido[4,3-d]pyrimidin-6-yl]methanone

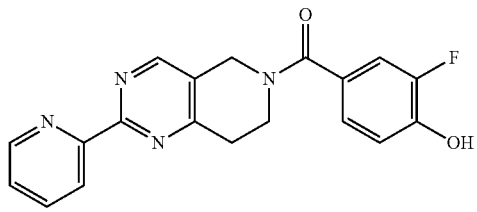 [SMILES: O=C(c1ccc(O)c(F)c1)N1CCc2nc(-c3ccccn3)ncc2C1]

A mixture of 2-(2-pyridyl)-5,6,7,8-tetrahydropyrido[4,3-d]pyrimidine hydrochloride (1 g, 3.067 mmol, the product of step 3 in Example 1), 3-fluoro-4-hydroxy-benzoic acid (0.718 g, 4.6 mmol), HATU (2.33 g, 6.13 mmol) and DIPEA (1.98 g, 15.34 mmol) in DMF (5 mL) was stirred at rt overnight. The resulting mixture was poured into water (5 mL) and extracted with EA (50 mL) for three times. The combined organic layer was concentrated in vacuo and the residue was purified by prep-HPLC to give (3-fluoro-4-hydroxy-phenyl)-[2-(2-pyridyl)-7,8-dihydro-5H-pyrido[4,3-d]pyrimidin-6-yl]methanone (20 mg) as light yellow solid. $^1$H NMR (400 MHz, CDCl$_3$) δ: 8.81-8.93 (m, 1H), 8.60-8.76 (m, 1H), 8.46-8.59 (m, 1H), 7.92 (td, 1H), 7.46 (ddd, 1H), 7.26-7.32 (m, 1H), 7.20 (dd, 1H), 7.08-7.15 (m, 1H), 4.90 (br. s., 2H), 3.95 (br. s., 2H), 3.15 (br. s., 2H). MS obsd. (ESI$^+$) [(M+H)$^+$]: 351.

Example 13

(4-Ethoxy-3-fluoro-phenyl)-[2-(2-pyridyl)-7,8-dihydro-5H-pyrido[4,3-d]pyrimidin-6-yl]methanone

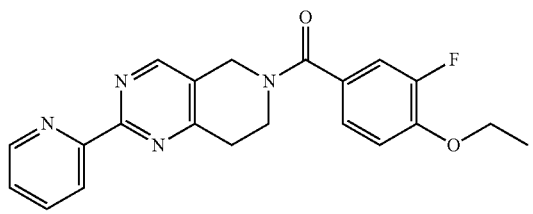 [SMILES: CCOc1ccc(C(=O)N2CCc3nc(-c4ccccn4)ncc3C2)cc1F]

A mixture of (3-fluoro-4-hydroxy-phenyl)-[2-(2-pyridyl)-7,8-dihydro-5H-pyrido[4,3-d]pyrimidin-6-yl]methanone (150 mg, 0.428 mmol, Example 12), bromoethane (47 mg, 0.428 mmol) and K$_2$CO$_3$ (118 mg, 0.857 mmol) in DMF (5 mL) was stirred at rt overnight. The resulting mixture was poured into water (5 mL) and extracted with EA (20 mL) for three times. The combined organic layer was concentrated in vacuo and the residue was purified by prep-HPLC to give (4-ethoxy-3-fluoro-phenyl)-[2-(2-pyridyl)-7,8-dihydro-5H-pyrido[4,3-d]pyrimidin-6-yl]methanone (12 mg) as light yellow solid. $^1$H NMR (400 MHz, CDCl$_3$) δ: 8.87 (d, 1H), 8.68 (br. s., 1H), 8.52 (d, 1H), 7.88 (td, 1H), 7.43 (td, 1H), 7.18-7.35 (m, 2H), 6.96-7.12 (m, 1H), 4.90 (br. s., 2H), 4.19 (q, 2H), 3.97 (br. s., 2H), 3.22 (t, 2H), 1.51 (t, 3H). MS obsd. (ESI$^+$) [(M+H)$^+$]: 379.

Example 14

[3-Fluoro-4-(2-methoxyethoxy)phenyl]-[2-(2-pyridyl)-7,8-dihydro-5H-pyrido[4,3-d]pyrimidin-6-yl]methanone

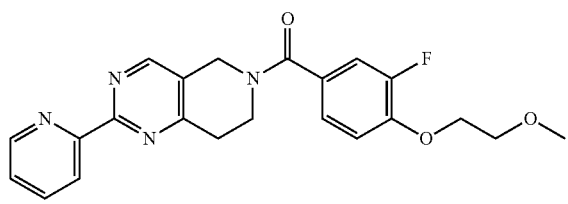 [SMILES: COCCOc1ccc(C(=O)N2CCc3nc(-c4ccccn4)ncc3C2)cc1F]

A mixture of (3-fluoro-4-hydroxy-phenyl)-[2-(2-pyridyl)-7,8-dihydro-5H-pyrido[4,3-d]pyrimidin-6-yl]methanone (150 mg, 0.428 mmol, Example 12), 1-bromo-2-methoxyethane (119 mg, 0.857 mmol) and $K_2CO_3$ (177 mg, 1.286 mmol) in DMF (5 mL) was stirred at rt overnight. The resulting mixture was poured into water (5 mL) and extracted with EA (20 mL) for three times. The combined organic layer was concentrated in vacuo and the residue was purified by prep-HPLC to give [3-fluoro-4-(2-methoxyethoxy)phenyl]-[2-(2-pyridyl)-7,8-dihydro-5H-pyrido[4,3-d]pyrimidin-6-yl]methanone (20 mg) as light yellow solid. $^1$H NMR (400 MHz, CDCl$_3$) δ: 8.81-8.90 (m, 1H), 8.68 (br. s., 1H), 8.52 (d, 1H), 7.88 (td, 1H), 7.43 (ddd, 1H), 7.18-7.35 (m, 2H), 7.02-7.16 (m, 1H), 4.89 (br. s., 2H), 4.22-4.35 (m, 2H), 3.96 (br. s., 2H), 3.82 (dd, 2H), 3.48 (s, 3H), 3.22 (t, 2H). MS obsd. (ESI$^+$) [(M+H)$^+$]: 409.

Example 15

[3-Fluoro-4-(3-methoxypropoxy)phenyl]-[2-(2-pyridyl)-7,8-dihydro-5H-pyrido[4,3-d]pyrimidin-6-yl]methanone

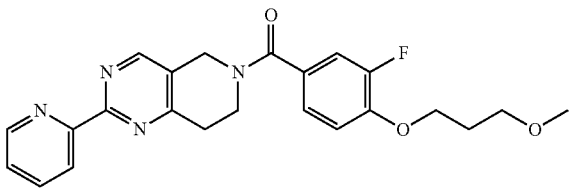

A mixture of (3-fluoro-4-hydroxy-phenyl)-[2-(2-pyridyl)-7,8-dihydro-5H-pyrido[4,3-d]pyrimidin-6-yl]methanone (150 mg, 0.428 mmol, Example 12), 1-bromo-3-methoxypropane (131 mg, 0.857 mmol) and $K_2CO_3$ (118 mg, 0.857 mmol) in DMF (5 mL) was stirred at rt overnight. The resulting mixture was poured into water (5 mL) and extracted with EA (20 mL) for three times. The combined organic layer was concentrated in vacuo and the residue was purified by prep-HPLC to give [3-fluoro-4-(3-methoxypropoxy)phenyl]-[2-(2-pyridyl)-7,8-dihydro-5H-pyrido[4,3-d]pyrimidin-6-yl]methanone (35 mg) as light yellow solid. $^1$H NMR (400 MHz, CDCl$_3$) δ: 8.86 (dt, 1H), 8.68 (br. s., 1H), 8.52 (d, 1H), 7.88 (td, 1H), 7.43 (ddd, 1H), 7.19-7.33 (m, 2H), 7.00-7.15 (m, 1H), 4.84-4.98 (m, 2H), 4.21 (t, 2H), 3.86-4.06 (m, 2H), 3.60 (t, 2H), 3.38 (s, 3H), 3.22 (s, 2H), 2.13 (t, 2H). MS obsd. (ESI$^+$) [(M+H)$^+$]: 423.

Example 16

[2-(2-Pyridyl)-7,8-dihydro-5H-pyrido[4,3-d]pyrimidin-6-yl]-(3,4,5-trimethoxyphenyl)methanone

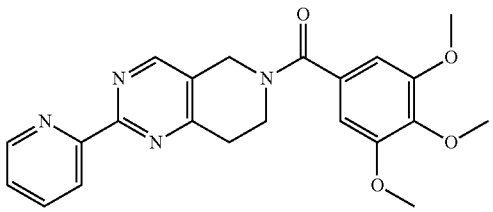 [SMILES: COc1cc(C(=O)N2CCc3nc(-c4ccccn4)ncc3C2)cc(OC)c1OC]

A mixture of 2-(2-pyridyl)-5,6,7,8-tetrahydropyrido[4,3-d]pyrimidine hydrochloride (300 mg, 0.92 mmol, the product of step 3 in Example 1), 3,4,5-trimethoxybenzoic acid (390 mg, 1.84 mmol), HATU (699 mg, 1.84 mmol) and DIPEA (595 mg, 4.6 mmol) in DMF (5 mL) was stirred at rt overnight. The resulting mixture was poured into water (5 mL) and extracted with EA (20 mL) for three times. The combined organic layer was concentrated in vacuo and the residue was purified by prep-HPLC to give [2-(2-pyridyl)-7,8-dihydro-5H-pyrido[4,3-d]pyrimidin-6-yl]-(3,4,5-trimethoxyphenyl)methanone (125 mg) as light yellow solid. $^1$H NMR (400 MHz, CDCl$_3$) δ: 8.84 (d, 1H), 8.68 (br. s., 1H), 8.50 (d, 1H), 7.87 (td, 1H), 7.41 (ddd, 1H), 6.64-6.76 (m, 2H), 4.89 (br. s., 2H), 3.69-4.14 (m, 11H), 3.22 (t, 2H). MS obsd. (ESI$^+$) [(M+H)$^+$]: 407.

Example 17

(3,5-Diethoxyphenyl)-[2-(2-pyridyl)-7,8-dihydro-5H-pyrido[4,3-d]pyrimidin-6-yl]methanone

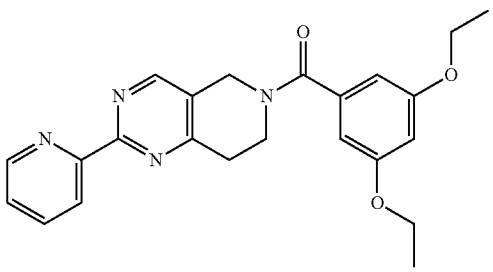 [SMILES: CCOc1cc(OCC)cc(C(=O)N2CCc3nc(-c4ccccn4)ncc3C2)c1]

A mixture of 2-(2-pyridyl)-5,6,7,8-tetrahydropyrido[4,3-d]pyrimidine hydrochloride (300 mg, 0.92 mmol, the product of step 3 in Example 1), 3,5-diethoxybenzoic acid (387 mg, 1.84 mmol), HATU (699 mg, 1.84 mmol) and DIPEA (595 mg, 4.6 mmol) in DMF (5 mL) was stirred at rt overnight. The resulting mixture was poured into water (5 mL) and extracted with EA (20 mL) for three times. The combined organic layer was concentrated in vacuo and the residue was purified by prep-HPLC to give (3,5-diethoxyphenyl)-[2-(2-pyridyl)-7,8-dihydro-5H-pyrido[4,3-d]pyrimidin-6-yl]methanone (175 mg) as light yellow solid. $^1$H NMR (400 MHz, CDCl$_3$) δ: 8.80-8.94 (m, 1H), 8.72 (d, 1H), 8.51 (d, 1H), 7.87 (td, 1H), 7.41 (ddd, 1H), 6.45-6.62 (m, 3H), 4.58-5.05 (m, 2H), 3.71-4.13 (m, 6H), 3.05-3.32 (m, 2H), 1.28-1.55 (m, 6H). MS obsd. (ESI$^+$) [(M+H)$^+$]: 405.

Example 18

(3-Chloro-5-methoxy-phenyl)-[2-(2-pyridyl)-7,8-dihydro-5H-pyrido[4,3-d]pyrimidin-6-yl]methanone

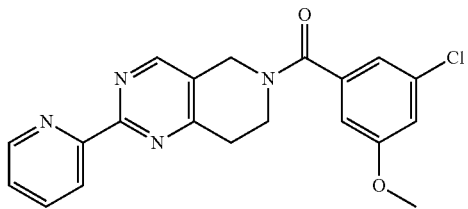 [SMILES: COc1cc(Cl)cc(C(=O)N2CCc3nc(-c4ccccn4)ncc3C2)c1]

A mixture of 2-(2-pyridyl)-5,6,7,8-tetrahydropyrido[4,3-d]pyrimidine hydrochloride (300 mg, 0.92 mmol, the product of step 3 in Example 1), 3-chloro-5-methoxy-benzoic acid (343 mg, 1.84 mmol), HATU (699 mg, 1.84 mmol) and DIPEA (595 mg, 4.6 mmol) in DMF (5 mL) was stirred at rt overnight. The resulting mixture was poured into water (5 mL) and extracted with EA (20 mL) for three times. The combined organic layer was concentrated in vacuo and the residue was purified by prep-HPLC to give (3-chloro-5-methoxy-phenyl)-[2-(2-pyridyl)-7,8-dihydro-5H-pyrido[4,3-d]pyrimidin-6-yl]methanone (98 mg) as light yellow solid. $^1$H NMR (400 MHz, CDCl$_3$) δ: 8.84 (d, 1H), 8.60-8.77 (m, 1H), 8.50 (d, 1H), 7.86 (td, 1H), 7.40 (ddd, 1H), 6.98-7.07 (m, 2H), 6.80-6.93 (m, 1H), 4.48-5.04 (m, 2H), 3.55-4.20 (m, 5H), 3.18 (br. s., 2H). MS obsd. (ESI$^+$) [(M+H)$^+$]: 381.

Example 19

(3,5-Dimethoxyphenyl)-[2-(2-pyridyl)-7,8-dihydro-5H-pyrido[4,3-d]pyrimidin-6-yl]methanone

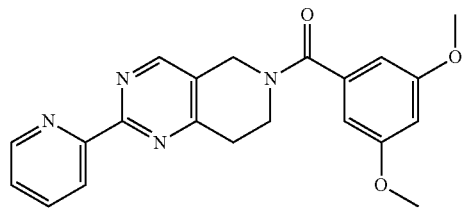 [SMILES: COc1cc(OC)cc(C(=O)N2CCc3nc(-c4ccccn4)ncc3C2)c1]

A mixture of 2-(2-pyridyl)-5,6,7,8-tetrahydropyrido[4,3-d]pyrimidine hydrochloride (300 mg, 0.92 mmol, the product of step 3 in Example 1), 3,5-dimethoxybenzoic acid (335 mg, 1.84 mmol), HATU (699 mg, 1.84 mmol) and DIPEA (595 mg, 4.6 mmol) in DMF (5 mL) was stirred at rt overnight. The resulting mixture was poured into water (5 mL) and extracted with EA (20 mL) for three times. The combined organic layer was concentrated in vacuo and the residue was purified by prep-HPLC to give (3,5-dimethoxyphenyl)-[2-(2-pyridyl)-7,8-dihydro-5H-pyrido[4,3-d]pyrimidin-6-yl]methanone (153 mg) as light yellow solid. $^1$H NMR (400 MHz, CDCl$_3$) δ: 8.83 (dd, 1H), 8.57-8.76 (m, 1H), 8.49 (d, 1H), 7.85 (td, 1H), 7.39 (ddd, 1H), 6.49-6.64 (m, 3H), 4.51-5.08 (m, 2H), 3.63-4.25 (m, 8H), 2.99-3.34 (m, 2H). MS obsd. (ESI$^+$) [(M+H)$^+$]: 377.

Example 20

(4-Fluoro-3-methyl-phenyl)-[2-(2-pyridyl)-7,8-dihydro-5H-pyrido[4,3-d]pyrimidin-6-yl]methanone

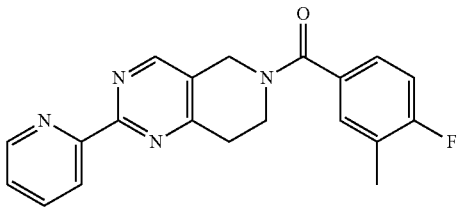 [SMILES: Cc1cc(C(=O)N2CCc3nc(-c4ccccn4)ncc3C2)ccc1F]

A mixture of 2-(2-pyridyl)-5,6,7,8-tetrahydropyrido[4,3-d]pyrimidine hydrochloride (300 mg, 0.92 mmol, the product of step 3 in Example 1), 4-fluoro-3-methyl-benzoic acid (283 mg, 1.84 mmol), HATU (699 mg, 1.84 mmol) and DIPEA (595 mg, 4.6 mmol) in DMF (5 mL) was stirred at room temperature overnight. The resulting mixture was poured into water (5 mL) and extracted with EA (20 mL) for three times. The combined organic layer was concentrated in vacuo and the residue was purified by prep-HPLC to give (4-fluoro-3-methyl-phenyl)-[2-(2-pyridyl)-7,8-dihydro-5H-pyrido[4,3-d]pyrimidin-6-yl]methanone (106 mg) as light yellow solid. $^1$H NMR (400 MHz, CDCl$_3$) δ: 8.83 (dd, 1H), 8.65 (br. s., 1H), 8.49 (d, 1H), 7.85 (td, 1H), 7.37-7.43 (m, 1H), 7.31-7.37 (m, 1H), 7.24-7.31 (m, 1H), 7.07 (t, 1H), 4.87 (br. s., 2H), 3.58-4.17 (m, 2H), 3.18 (br. s., 2H), 2.17-2.47 (m, 3H). MS obsd. (ESI$^+$) [(M+H)$^+$]: 349.

Example 21

(3-Chloro-4-methoxy-phenyl)-[2-(2-pyridyl)-7,8-dihydro-5H-pyrido[4,3-d]pyrimidin-6-yl]methanone

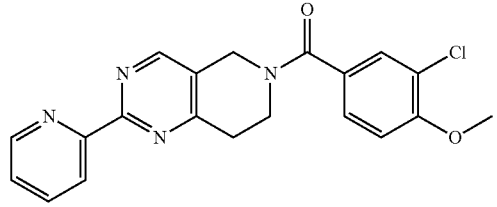 [SMILES: COc1ccc(C(=O)N2CCc3nc(-c4ccccn4)ncc3C2)cc1Cl]

A mixture of 2-(2-pyridyl)-5,6,7,8-tetrahydropyrido[4,3-d]pyrimidine hydrochloride (300 mg, 0.92 mmol, the product of step 3 in Example 1), 3-chloro-4-methoxy-benzoic acid (343 mg, 1.84 mmol), HATU (699 mg, 1.84 mmol) and DIPEA (595 mg, 4.6 mmol) in DMF (5 mL) was stirred at rt overnight. The resulting mixture was poured into water (5 mL) and extracted with EA (20 mL) for three times. The combined organic layer was concentrated in vacuo and the residue was purified by prep-HPLC to give (3-chloro-4-methoxy-phenyl)-[2-(2-pyridyl)-7,8-dihydro-5H-pyrido[4,3-d]pyrimidin-6-yl]methanone (113 mg) as light yellow solid. $^1$H NMR (400 MHz, CDCl$_3$) δ: 8.84 (dd, 1H), 8.65 (br. s., 1H), 8.50 (d, 1H), 7.87 (td, 1H), 7.50-7.63 (m, 1H), 7.36-7.46 (m, 2H), 6.91-7.07 (m, 1H), 4.87 (br. s., 2H), 3.80-4.04 (m, 5H), 3.11-3.29 (m, 2H). MS obsd. (ESI$^+$) [(M+H)$^+$]: 381.

Example 22

(3,4-Dimethoxyphenyl)-[2-(2-pyridyl)-7,8-dihydro-5H-pyrido[4,3-d]pyrimidin-6-yl]methanone

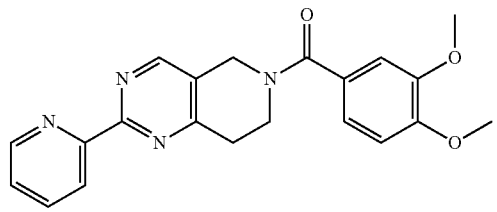 [SMILES: COc1ccc(C(=O)N2CCc3nc(-c4ccccn4)ncc3C2)cc1OC]

A mixture of 2-(2-pyridyl)-5,6,7,8-tetrahydropyrido[4,3-d]pyrimidine hydrochloride (300 mg, 0.92 mmol, the product of step 3 in Example 1), 3,4-dimethoxybenzoic acid (335 mg, 1.84 mmol), HATU (699 mg, 1.84 mmol) and DIPEA (595 mg, 4.6 mmol) in DMF (5 mL) was stirred at rt overnight. The resulting mixture was poured into water (5 mL) and extracted with EA (20 mL) for three times. The combined organic layer was concentrated in vacuo and the residue was purified by prep-HPLC to give (3,4-dimethoxyphenyl)-[2-(2-pyridyl)-7,8-dihydro-5H-pyrido[4,3-d]pyrimidin-6-yl]methanone (20 mg) as light yellow solid. $^1$H NMR (400 MHz, CDCl$_3$) δ: 8.86 (dd, 1H), 8.68 (br. s., 1H), 8.52 (d, 1H), 7.88 (td, 1H), 7.43 (ddd, 1H), 7.05-7.16 (m, 2H), 6.88-6.99 (m, 1H), 4.91 (br. s., 2H), 3.75-4.18 (m, 8H), 3.23 (t, 2H). MS obsd. (ESI$^+$) [(M+H)$^+$]: 377.

Example 23

(3-chloro-4-hydroxy-phenyl)-[2-(2-pyridyl)-7,8-dihydro-5H-pyrido[4,3-d]pyrimidin-6-yl]methanone

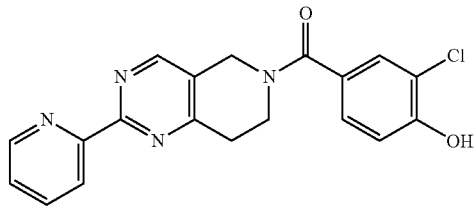 [SMILES: O=C(c1ccc(O)c(Cl)c1)N1CCc2nc(-c3ccccn3)ncc2C1]

A mixture of 2-(2-pyridyl)-5,6,7,8-tetrahydropyrido[4,3-d]pyrimidine hydrochloride (1 g, 3.07 mmol, the product of step 3 in Example 1), 3-chloro-4-hydroxy-benzoic acid (0.835 g, 4.6 mmol), HATU (2.33 g, 6.13 mmol) and DIPEA (1.98 g, 15.33 mmol) in DMF (10 mL) was stirred at rt overnight. The resulting mixture was poured into water (10 mL) and extracted with EA (20 mL) for three times. The combined organic layer was concentrated in vacuo. The residue was purified by prep-HPLC to give (3-chloro-4-hydroxy-phenyl)-[2-(2-pyridyl)-7,8-dihydro-5H-pyrido[4,3-d]pyrimidin-6-yl]methanone (20 mg) as light yellow solid. $^1$H NMR (400 MHz, Methanol-d4) δ: 8.69-8.96 (m, 3H), 8.44 (td, 1H), 7.91 (ddd, 1H), 7.56 (d, 1H), 7.37 (dd, 1H), 6.96-7.12 (m, 1H), 4.93-5.03 (m, 2H), 3.86-4.11 (m, 2H), 3.16-3.28 (m, 2H). MS obsd. (ESI$^+$) [(M+H)$^+$]: 367.

Example 24

[3-Chloro-4-(3-methoxypropoxy)phenyl]-[2-(2-pyridyl)-7,8-dihydro-5H-pyrido[4,3-d]pyrimidin-6-yl]methanone

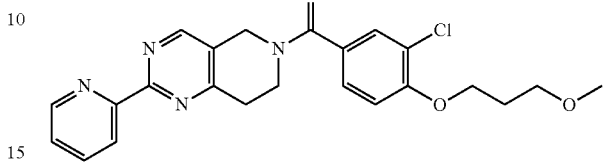

A mixture of (3-chloro-4-hydroxy-phenyl)-[2-(2-pyridyl)-7,8-dihydro-5H-pyrido[4,3-d]pyrimidin-6-yl]methanone (100 mg, 0.273 mmol, Example 23), 1-bromo-3-methoxy-propane (84 mg, 0.546 mmol) and Cs$_2$CO$_3$ (266 mg, 0.82 mmol) in DMF (5 mL) was heated at 100° C. overnight. The resulting mixture was poured into water (5 mL) and extracted with EA (20 mL) for three times. The combined organic layer was concentrated in vacuo and the residue was purified by prep-HPLC to give [3-chloro-4-(3-methoxypropoxy)phenyl]-[2-(2-pyridyl)-7,8-dihydro-5H-pyrido[4,3-d]pyrimidin-6-yl]methanone (110 mg) as light yellow solid. $^1$H NMR (400 MHz, CDCl$_3$) δ: 8.87 (d, 1H), 8.68 (br. s., 1H), 8.53 (d, 1H), 7.90 (td, 1H), 7.52-7.63 (m, 1H), 7.44 (dd, 1H), 7.34-7.41 (m, 1H), 6.95-7.06 (m, 1H), 4.85-4.98 (m, 2H), 4.16-4.25 (m, 2H), 3.88-4.03 (m, 2H), 3.59-3.68 (m, 2H), 3.38 (s, 3H), 3.15-3.27 (m, 2H), 2.14 (m, 2H). MS obsd. (ESI$^+$) [(M+H)$^+$]: 439.

Example 25

(4-Hydroxy-3-methoxy-phenyl)-[2-(2-pyridyl)-7,8-dihydro-5H-pyrido[4,3-d]pyrimidin-6-yl]methanone

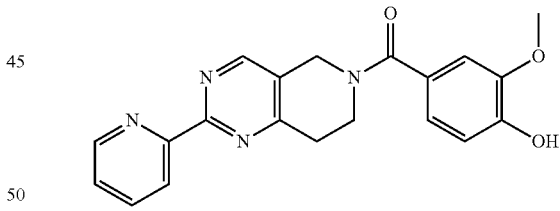

A mixture of 2-(2-pyridyl)-5,6,7,8-tetrahydropyrido[4,3-d]pyrimidine hydrochloride (1 g, 3.06 mmol, the product of step 3 in Example 1), 4-hydroxy-3-methoxy-benzoic acid (0.774 g, 4.6 mmol), HATU (2.33 g, 6.14 mmol) and DIPEA (1.982 g, 15.34 mmol) in DMF (10 mL) was stirred at rt overnight. The resulting mixture was poured into water (10 mL) and extracted with EA (20 mL) for three times. The combined organic layer was concentrated in vacuo and the residue was purified by prep-HPLC to give (4-hydroxy-3-methoxy-phenyl)-[2-(2-pyridyl)-7,8-dihydro-5H-pyrido[4,3-d]pyrimidin-6-yl]methanone (20 mg) as light yellow solid. $^1$H NMR (400 MHz, CDCl$_3$) δ: 8.86 (d, 1H), 8.68 (br. s., 1H), 8.52 (d, 1H), 7.89 (td, 1H), 7.37-7.50 (m, 1H), 6.85-7.16 (m, 3H), 5.88-6.11 (m, 1H), 4.91 (br. s., 2H), 3.94 (s, 5H), 3.11-3.37 (m, 2H). MS obsd. (ESI$^+$) [(M+H)$^+$]: 363.

Example 26

[3-Methoxy-4-(3-methoxypropoxy)phenyl]-[2-(2-pyridyl)-7,8-dihydro-5H-pyrido[4,3-d]pyrimidin-6-yl]methanone

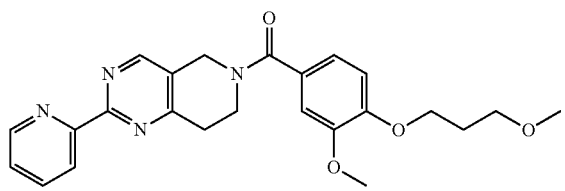 [SMILES: COCCCOc1ccc(C(=O)N2CCc3nc(-c4ccccn4)ncc3C2)cc1OC]

A mixture of (4-hydroxy-3-methoxy-phenyl)-[2-(2-pyridyl)-7,8-dihydro-5H-pyrido[4,3-d]pyrimidin-6-yl]methanone (100 mg, 0.276 mmol, Example 25), 1-bromo-3-methoxy-propane (84.5 mg, 0.552 mmol) and $Cs_2CO_3$ (269 mg, 0.829 mmol) in DMF (5 mL) was heated at 100° C. overnight. The resulting mixture was poured into water (5 mL) and extracted with EA (20 mL) for three times. The combined organic layer was concentrated in vacuo and the residue was purified by prep-HPLC to give [3-methoxy-4-(3-methoxypropoxy)phenyl]-[2-(2-pyridyl)-7,8-dihydro-5H-pyrido[4,3-d]pyrimidin-6-yl]methanone (65 mg) as light yellow solid.
$^1$H NMR (400 MHz, $CDCl_3$) δ: 8.86 (dd, 1H), 8.67 (br. s., 1H), 8.52 (d, 1H), 7.88 (td, 1H), 7.42 (ddd, 1H), 7.02-7.13 (m, 2H), 6.96 (d, 1H), 4.82-5.01 (m, 2H), 4.13-4.27 (m, 2H), 3.90 (s, 5H), 3.60 (s, 2H), 3.38 (s, 3H), 3.13-3.30 (m, 2H), 2.07-2.23 (m, 2H). MS obsd. ($ESI^+$) [(M+H)$^+$]: 435.

Example 27

(5-Methyl-2-pyridyl)-[2-(2-pyridyl)-7,8-dihydro-5H-pyrido[4,3-d]pyrimidin-6-yl]methanone

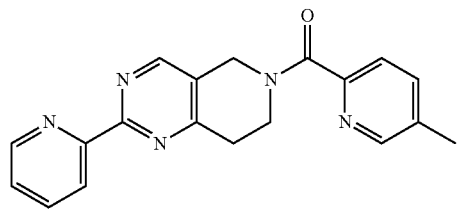 [SMILES: Cc1ccc(C(=O)N2CCc3nc(-c4ccccn4)ncc3C2)nc1]

A mixture of 2-(2-pyridyl)-5,6,7,8-tetrahydropyrido[4,3-d]pyrimidine hydrochloride (300 mg, 0.92 mmol, the product of step 3 in Example 1), 5-methylpyridine-2-carboxylic acid (252 mg, 1.84 mmol), HATU (699 mg, 1.84 mmol) and DIPEA (595 mg, 4.6 mmol) in DMF (5 mL) was stirred at rt overnight. Then the mixture was poured into water (5 mL) and the resulting mixture was extracted with EA (20 mL) for three times. The combined organic layer was concentrated in vacuo and the residue was purified by prep-HPLC to give (5-methyl-2-pyridyl)-[2-(2-pyridyl)-7,8-dihydro-5H-pyrido[4,3-d]pyrimidin-6-yl]methanone (44 mg) as light yellow solid. $^1$H NMR (400 MHz, Methanol-d4) δ: 8.80-8.87 (m, 1H), 8.71-8.78 (m, 1H), 8.47-8.63 (m, 2H), 8.01 (t, 1H), 7.83 (d, 1H), 7.64 (d, 1H), 7.51-7.59 (m, 1H), 5.03 (s, 2H), 4.18 (br. s., 1H), 3.93 (t, 1H), 3.22 (t, 2H), 2.46 (s, 3H). MS obsd. ($ESI^+$) [(M+H)$^+$]: 332.

Example 28

(3-Fluoro-4-methyl-phenyl)-[2-(2-pyridyl)-7,8-dihydro-5H-pyrido[4,3-d]pyrimidin-6-yl]methanone

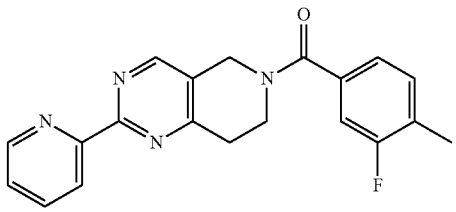 [SMILES: Cc1ccc(C(=O)N2CCc3nc(-c4ccccn4)ncc3C2)cc1F]

A mixture of 2-(2-pyridyl)-5,6,7,8-tetrahydropyrido[4,3-d]pyrimidine hydrochloride (300 mg, 0.92 mmol, the product of step 3 in Example 1), 3-fluoro-4-methyl-benzoic acid (283 mg, 1.84 mmol), HATU (699 mg, 1.84 mmol) and DIPEA (595 mg, 4.6 mmol) in DMF (5 mL) was stirred at rt overnight. Then the resulting mixture was poured into water (5 mL) and extracted with EA (20 mL) for three times. The combined organic layer was concentrated in vacuo and the residue was purified by prep-HPLC to give (3-fluoro-4-methyl-phenyl)-[2-(2-pyridyl)-7,8-dihydro-5H-pyrido[4,3-d]pyrimidin-6-yl]methanone (43 mg) as light yellow solid.
$^1$H NMR (400 MHz, $CDCl_3$) δ: 8.85 (dd, 1H), 8.58-8.78 (m, 1H), 8.50 (d, 1H), 7.87 (td, 1H), 7.41 (ddd, 1H), 7.25-7.34 (m, 1H), 7.10-7.23 (m, 2H), 4.90 (br. s., 2H), 3.89 (br. s., 2H), 3.01-3.36 (m, 2H), 2.14-2.52 (m, 3H). MS obsd. ($ESI^+$) [(M+H)$^+$]: 349.

Example 29

(5-Methoxy-2-pyridyl)-[2-(2-pyridyl)-7,8-dihydro-5H-pyrido[4,3-d]pyrimidin-6-yl]methanone

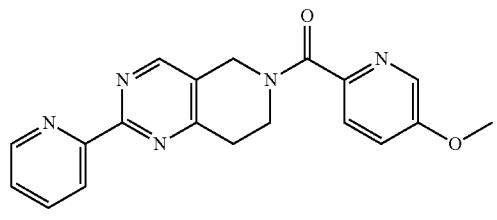

A mixture of 2-(2-pyridyl)-5,6,7,8-tetrahydropyrido[4,3-d]pyrimidine hydrochloride (300 mg, 0.92 mmol, the product of step 3 in Example 1), 5-methoxypyridine-2-carboxylic acid (282 mg, 1.84 mmol), HATU (699 mg, 1.84 mmol) and DIPEA (595 mg, 4.6 mmol) in DMF (5 mL) was stirred at rt overnight. Then the resulting mixture was poured into water (5 mL) and extracted with EA (20 mL) for three times. The combined organic layer was concentrated in vacuo and the residue was purified by prep-HPLC to give (5-methoxy-2-pyridyl)-[2-(2-pyridyl)-7,8-dihydro-5H-pyrido[4,3-d]pyrimidin-6-yl]methanone (16 mg) as light yellow solid. $^1$H NMR (400 MHz, Methanol-d4) δ: 8.84 (br. s., 1H), 8.76 (d, 1H), 8.49-8.68 (m, 1H), 8.28-8.41 (m, 1H), 8.02-8.18 (m, 1H), 7.76 (d, 1H), 7.60-7.69 (m, 1H), 7.54 (dd, 1H), 5.02 (s, 2H), 4.00-4.25 (m, 2H), 3.97 (s, 3H), 3.25 (br. s., 2H). MS obsd. ($ESI^+$) [(M+H)$^+$]: 348.

Example 30

(3,5-Difluoro-4-methoxy-phenyl)-[2-(2-pyridyl)-7,8-dihydro-5H-pyrido[4,3-d]pyrimidin-6-yl]methanone

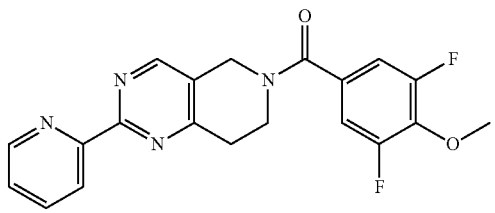 [SMILES: COc1c(F)cc(C(=O)N2CCc3nc(-c4ccccn4)ncc3C2)cc1F]

A mixture of 2-(2-pyridyl)-5,6,7,8-tetrahydropyrido[4,3-d]pyrimidine hydrochloride (300 mg, 0.92 mmol, the product of step 3 in Example 1), 3,5-difluoro-4-methoxy-benzoic acid (346 mg, 1.84 mmol), HATU (699 mg, 1.84 mmol) and DIPEA (595 mg, 4.6 mmol) in DMF (5 mL) was stirred at rt overnight. Then the resulting mixture was poured into water (5 mL) and extracted with EA (20 mL) for three times. The combined organic layer was concentrated in vacuo and the residue was purified by prep-HPLC to give (3,5-difluoro-4-methoxy-phenyl)-[2-(2-pyridyl)-7,8-dihydro-5H-pyrido[4,3-d]pyrimidin-6-yl]methanone (62 mg) as light yellow solid. $^1$H NMR (400 MHz, Methanol-d4) δ: 9.01 (d, 1H), 8.89 (dd, 2H), 8.73 (td, 1H), 8.15 (ddd, 1H), 7.24 (d, 2H), 4.93-5.08 (m, 2H), 3.79-4.15 (m, 5H), 3.19-3.28 (m, 2H). MS obsd. (ESI$^+$) [(M+H)$^+$]: 383.

Example 31

(6-Methyl-3-pyridyl)-[2-(2-pyridyl)-7,8-dihydro-5H-pyrido[4,3-d]pyrimidin-6-yl]methanone

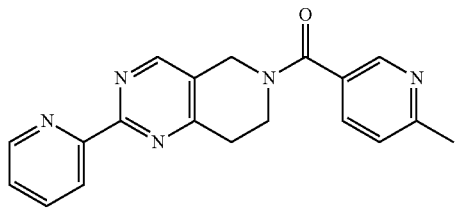 [SMILES: Cc1ccc(C(=O)N2CCc3nc(-c4ccccn4)ncc3C2)cn1]

A mixture of 2-(2-pyridyl)-5,6,7,8-tetrahydropyrido[4,3-d]pyrimidine hydrochloride (300 mg, 0.92 mmol, the product of step 3 in Example 1), 6-methylpyridine-3-carboxylic acid (252 mg, 1.84 mmol), HATU (699 mg, 1.84 mmol) and DIPEA (595 mg, 4.6 mmol) in DMF (5 mL) was stirred at rt overnight. Then the resulting mixture was poured into water (5 mL) and extracted with EA (20 mL) for three times. The combined organic layer was concentrated in vacuo and the residue was purified by prep-HPLC to (6-methyl-3-pyridyl)-[2-(2-pyridyl)-7,8-dihydro-5H-pyrido[4,3-d]pyrimidin-6-yl]methanone (19 mg) as light yellow solid. $^1$H NMR (400 MHz, CDCl$_3$) δ: 8.81-8.91 (m, 1H), 8.59-8.78 (m, 2H), 8.41-8.56 (m, 1H), 7.81-7.94 (m, 1H), 7.74 (dd, 1H), 7.36-7.50 (m, 1H), 7.17-7.35 (m, 1H), 4.95 (br. s., 2H), 3.67-4.10 (m, 2H), 3.21 (br. s., 2H), 2.51-2.77 (m, 3H). MS obsd. (ESI$^+$) [(M+H)$^+$]: 332.

Example 32

(4-Methyl-2-thienyl)-[2-(2-pyridyl)-7,8-dihydro-5H-pyrido[4,3-d]pyrimidin-6-yl]methanone

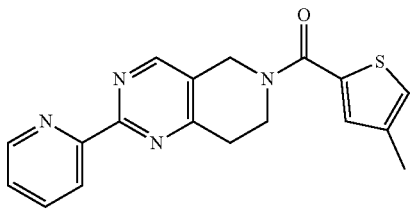 [SMILES: Cc1csc(C(=O)N2CCc3nc(-c4ccccn4)ncc3C2)c1]

A mixture of 2-(2-pyridyl)-5,6,7,8-tetrahydropyrido[4,3-d]pyrimidine hydrochloride (300 mg, 0.92 mmol, the product of step 3 in Example 1), 4-methylthiophene-2-carboxylic acid (262 mg, 1.84 mmol), HATU (699 mg, 1.84 mmol) and DIPEA (595 mg, 4.6 mmol) in DMF (5 mL) was stirred at rt overnight. Then the resulting mixture was poured into water (5 mL) and extracted with EA (20 mL) for three times. The combined organic layer was concentrated in vacuo and the residue was purified by prep-HPLC to give (4-methyl-2-thienyl)-[2-(2-pyridyl)-7,8-dihydro-5H-pyrido[4,3-d]pyrimidin-6-yl]methanone (25 mg) as light yellow solid. $^1$H NMR (400 MHz, Methanol-d4) δ: 8.71-8.82 (m, 2H), 8.52-8.65 (m, 1H), 8.09 (td, 1H), 7.58-7.69 (m, 1H), 7.35-7.48 (m, 1H), 7.25-7.33 (m, 1H), 4.96-5.13 (m, 2H), 4.04-4.24 (m, 2H), 3.20 (s, 2H), 2.33 (s, 3H). MS obsd. (ESI$^+$) [(M+H)$^+$]: 337.

Example 33

(5-Methylisoxazol-3-yl)-[2-(2-pyridyl)-7,8-dihydro-5H-pyrido[4,3-d]pyrimidin-6-yl]methanone

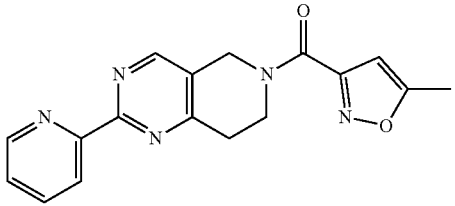 [SMILES: Cc1cc(C(=O)N2CCc3nc(-c4ccccn4)ncc3C2)no1]

A mixture of 2-(2-pyridyl)-5,6,7,8-tetrahydropyrido[4,3-d]pyrimidine hydrochloride (300 mg, 0.92 mmol, the product of step 3 in Example 1), 5-methylisoxazole-3-carboxylic acid (234 mg, 1.84 mmol), HATU (699 mg, 1.84 mmol) and DIPEA (595 mg, 4.6 mmol) in DMF (5 mL) was stirred at rt overnight. Then the resulting mixture was poured into water (5 mL) and extracted with EA (20 mL) for three times. The combined organic layer was concentrated in vacuo and the residue was purified by prep-HPLC to give (5-methylisoxazol-3-yl)-[2-(2-pyridyl)-7,8-dihydro-5H-pyrido[4,3-d]pyrimidin-6-yl]methanone (39 mg) as light yellow solid. $^1$H NMR (400 MHz, CDCl$_3$) δ: 8.83-8.94 (m, 2H), 8.45-8.78 (m, 2H), 8.23 (s, 1H), 7.88-8.08 (m, 1H), 7.43-7.60 (m, 1H), 6.34-6.47 (m, 1H), 5.22 (s, 1H), 5.01 (s, 1H), 4.26 (t, 1H), 4.09-4.22 (m, 1H), 3.12-3.36 (m, 2H), 2.39-2.64 (m, 3H). MS obsd. (ESI$^+$) [(M+H)$^+$]: 322.

Example 34

(−)-(3,4-Dimethoxyphenyl)-[5-methyl-2-(2-pyridyl)-7,8-dihydro-5H-pyrido[4,3-d]pyrimidin-6-yl]methanone

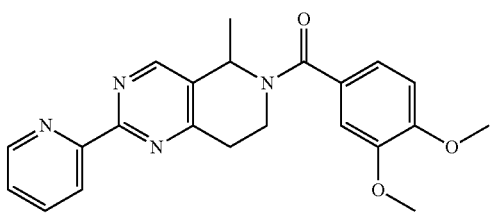 [SMILES: COc1ccc(C(=O)N2CCc3nc(-c4ccccn4)ncc3C2C)cc1OC]

Step 1: Preparation of Tert-Butyl 5-methyl-2-(2-pyridyl)-7,8-dihydro-5H-pyrido[4,3-d]pyrimidine-6-carboxylate

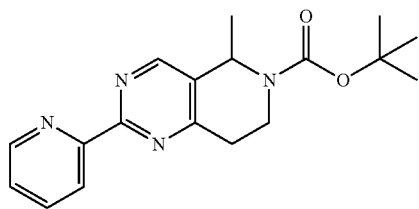 [SMILES: CC1c2cnc(-c3ccccn3)nc2CCN1C(=O)OC(C)(C)C]

To a solution of tert-butyl 2-methyl-4-oxo-piperidine-1-carboxylate (3.00 g, 14.1 mmol) in DMF (20 mL) was added DMFDMA (1.84 g, 15.47 mmol). The resulting mixture was heated at 90° C. with stirring overnight. After being cooled to rt, the resulting reaction mixture was concentrated in vacuo and the residue was dissolved in EtOH (50 mL). To the solution was added pyridine-2-carboxamidine hydrochloride (2.2 g, 14.1 mmol) and sodium methoxide (1.05 g, 19.4 mmol). After being heated at 100° C. with stirring overnight, the resulting mixture was cooled down to rt and concentrated in vacuo. The residue was diluted with water (15 mL) and then extracted with EA (30 mL) for three times. The combined organic layer was dried over anhydrous Na$_2$SO$_4$ and concentrated in vacuo to give crude tert-butyl 5-methyl-2-(2-pyridyl)-7,8-dihydro-5H-pyrido[4,3-d]pyrimidine-6-carboxylate (2.5 g) which was used in the next step directly without further purification.

Step 2: Preparation of 5-methyl-2-(2-pyridyl)-5,6,7,8-tetrahydropyrido[4,3 d]pyrimidine

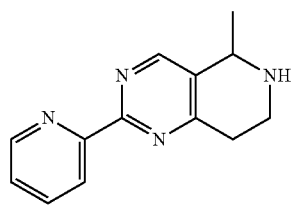 [SMILES: CC1NCCc2nc(-c3ccccn3)ncc21]

A mixture of crude tert-butyl 5-methyl-2-(2-pyridyl)-7,8-dihydro-5H-pyrido[4,3-d]pyrimidine-6-carboxylate and 2,2,2-trifluoroacetic acid (15 mL) in DCM (30 mL) was stirred at rt for 3 hrs. The resulting mixture was concentrated in vacuo to give crude 5-methyl-2-(2-pyridyl)-5,6,7,8-tetrahydropyrido[4,3 d]pyrimidine as trifluoroacetic acid salt (2.6 g).

Step 3: Preparation of (−)-(3,4-dimethoxyphenyl)-[5-methyl-2-(2-pyridyl)-7,8-dihydro-5H-pyrido[4,3-d]pyrimidin-6-yl]methanone

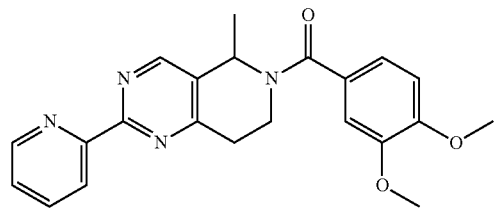 [SMILES: COc1ccc(C(=O)N2CCc3nc(-c4ccccn4)ncc3C2C)cc1OC]

A mixture of 5-methyl-2-(2-pyridyl)-5,6,7,8-tetrahydropyrido[4,3 d]pyrimidine hydrochloride (300 mg, 0.882 mmol), 3,4-dimethoxybenzoic acid (321 mg, 1.76 mmol), HATU (670 mg, 1.76 mmol) and DIPEA (570 mg, 4.41 mmol) in DMF (5 mL) was stirred at rt overnight. The resulting mixture was poured into water (5 mL) and extracted with EA (20 mL) for three times. The combined organic layer was concentrated in vacuo and the residue was purified by prep-HPLC and then SFC to give (−)-(3,4-dimethoxyphenyl)-[5-methyl-2-(2-pyridyl)-7,8-dihydro-5H-pyrido[4,3-d]pyrimidin-6-yl]methanone (35 mg) as light yellow solid. $^1$H NMR (400 MHz, CDCl$_3$) δ: 8.89 (br. s., 1H), 8.71 (br. s., 1H), 8.54 (d, 1H), 7.92 (t, 1H), 7.39-7.52 (m, 1H), 7.00-7.14 (m, 2H), 6.94 (d, 1H), 5.62-6.01 (m, 1H), 3.94 (d, 6H), 2.87-3.70 (m, 4H), 1.67 (d, 3H). MS obsd. (ESI$^+$) [(M+H)$^+$]: 391. [a]$_D^{20}$=−0.286° (14 mg/mL, methanol).

Example 35

(−)-(3,4-Dimethoxyphenyl)-[5-ethyl-2-(2-pyridyl)-7,8-dihydro-5H-pyrido[4,3-d]pyrimidin-6-yl]methanone

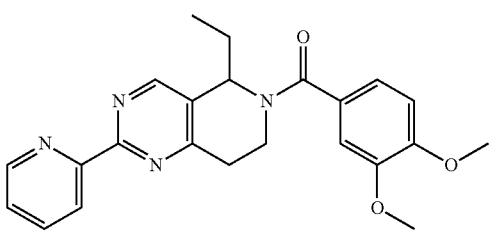 [SMILES: CCC1c2cnc(-c3ccccn3)nc2CCN1C(=O)c1ccc(OC)c(OC)c1]

Step 1: Preparation of Benzyl 2-ethyl-4-oxo-2,3-dihydropyridine-1-carboxylate

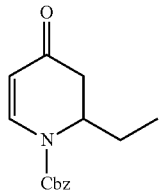

A mixture of 4-methoxypyridine (10 g, 91.7 mmol) and CbzCl (15.6 g, 91.7 mmol) in THF (100 mL) was cooled to −23° C. Then to the cooled mixture was added EtMgBr (30.6 mL, 91.7 mmol) dropwise. The resulting mixture was stirred at −23° C. for 30 min, then poured into 10% HCl and stirred further at 15° C. for 20 min. The resulting mixture was extracted with MTBE (100 mL) for 3 times. The combined organic layer was washed with brine and concentrated in vacuo. The residue was further purified by flash column (eluting with PE/EA=1:1, v:v) to give benzyl 2-ethyl-4-oxo-2,3-dihydropyridine-1-carboxylate (24.8 g) as a green oil.

Step 2: Preparation of Benzyl 2-ethyl-4-oxo-piperidine-1-carboxylate

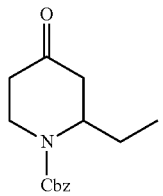 [SMILES: CCC1CC(=O)CCN1C(=O)OCc1ccccc1]

A mixture of benzyl 2-ethyl-4-oxo-2,3-dihydropyridine-1-carboxylate (24.7 g, 95.34 mmol) and Zn (30.4 g, 0.477 mol) in AcOH (250 mL) was heated at 80° C. with stirring for 12 hrs. The resulting mixture was concentrated in vacuo. The residue was dissolved in EA (500 mL) and filtered. The filtrate was washed with brine, dried over $Na_2SO_4$ and concentrated in vacuo to give crude benzyl 2-ethyl-4-oxo-piperidine-1-carboxylate (28.5 g) as yellow oil which was used directly in the next step without any further purification.

Step 3: Preparation of Benzyl 3-(dimethylaminomethylene)-2-ethyl-4-oxo-piperidine-1-carboxylate

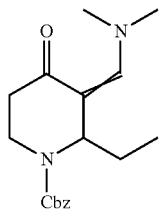 [SMILES: CCC1C(=CN(C)C)C(=O)CCN1C(=O)OCc1ccccc1]

A mixture of benzyl 2-ethyl-4-oxo-piperidine-1-carboxylate (28.5 g, crude) and DMFDMA (300 mL) was heated at 100° C. with stirring for 12 hrs. The resulting mixture was concentrated in vacuo to give crude benzyl 3-(dimethylaminomethylene)-2-ethyl-4-oxo-piperidine-1-carboxylate (30 g, crude) as yellow oil, which was directly used in the next step without any further purification.

Step 4: Preparation of Benzyl 5-ethyl-2-(2-pyridyl)-7,8-dihydro-5H-pyrido[4,3-d]pyrimidine-6-carboxylate

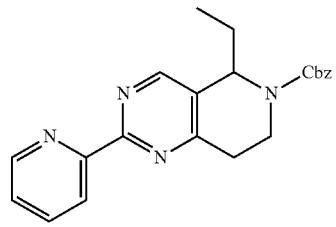 [SMILES: CCC1c2cnc(-c3ccccn3)nc2CCN1C(=O)OCc1ccccc1]

To a solution of crude benzyl 3-(dimethylaminomethylene)-2-ethyl-4-oxo-piperidine-1-carboxylate (30 g, crude) in MeOH (300 mL) was added pyridine-2-carboxamidine hydrochloride (15 g, 95 mmol) and $K_2CO_3$ (29 g, 163 mmol). The resulting mixture was stirred at 50° C. for 12 hrs and concentrated in vacuo. The residue was dissolved in DCM (500 mL) and the solution was washed with brine, dried over with $Na_2SO_4$ and concentrated in vacuo. The residue was purified by column (eluting with DCM/MeOH=40/1, v:v) to give benzyl 5-ethyl-2-(2-pyridyl)-7,8-dihydro-5H-pyrido[4,3-d]pyrimidine-6-carboxylate (15 g) as a green oil.

Step 5: Preparation of 5-ethyl-2-(2-pyridyl)-5,6,7,8-tetrahydropyrido[4,3 d]pyrimidine

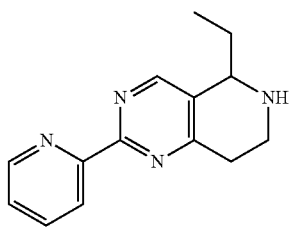 [SMILES: CCC1NCCc2nc(-c3ccccn3)ncc21]

To a solution of benzyl 5-ethyl-2-(2-pyridyl)-7,8-dihydro-5H-pyrido[4,3-d]pyrimidine-6-carboxylate (5 g, 13.4 mmol) in MeOH (50 mL) was added Pd/C (10%, 0.5 g) and the resulting mixture was stirred at rt under hydrogen for 12 hrs and then filtered. The filtrate was concentrated in vacuo to give 5-ethyl-2-(2-pyridyl)-5,6,7,8-tetrahydropyrido[4,3 d]pyrimidine (3.2 g) as a black oil, which was directly used in the next step without any further purification.

Step 6: Preparation of (−)-(3,4-dimethoxyphenyl)-[5-ethyl-2-(2-pyridyl)-7,8-dihydro-5H-pyrido[4,3-d]pyrimidin-6-yl]methanone

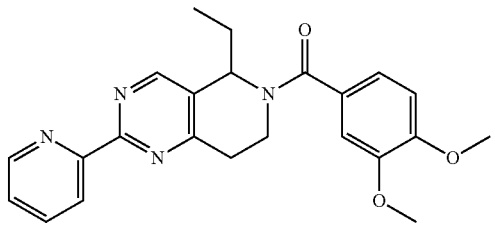 [SMILES: CCC1c2cnc(-c3ccccn3)nc2CCN1C(=O)c1ccc(OC)c(OC)c1]

A mixture of 5-ethyl-2-(2-pyridyl)-5,6,7,8-tetrahydro-pyrido[4,3 d]pyrimidine (400 mg, 1.67 mmol), 3,4-dimethoxybenzoic acid (455 mg, 2.5 mmol), HATU (1267 mg, 3.33 mmol) and DIPEA (1078 mg, 8.33 mmol) in DMF (5 mL) was stirred at rt overnight. The resulting mixture was poured into water (5 mL) and extracted with EA (30 mL) for three times. The combined organic layer was concentrated in vacuo and the residue was purified by prep-HPLC and then SFC to give (−)-(3,4-dimethoxyphenyl)-[5-ethyl-2-(2-pyridyl)-7,8-dihydro-5H-pyrido[4,3-d]pyrimidin-6-yl] methanone (16 mg) as light yellow solid. $^1$H NMR (400 MHz, CDCl$_3$) δ: 8.62 (br. s., 2H), 8.00 (br. s., 1H), 7.54 (br. s., 1H), 6.75-7.14 (m, 3H), 5.91 (br. s., 1H), 4.99 (br. s., 1H), 4.15 (d, 1H), 3.77-4.04 (m, 6H), 2.49-3.72 (m, 5H), 1.17 (br. s., 3H). MS obsd. (ESI$^+$) [(M+H)$^+$]: 405. [a]$_D^{20}$=−10.000° (2 mg/mL, methanol).

Example 36

(6-Methoxy-3-pyridyl)-[2-(2-pyridyl)-7,8-dihydro-5H-pyrido[4,3-d]pyrimidin-6-yl]methanone

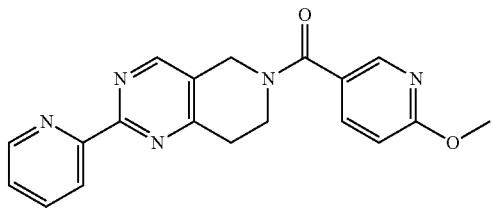 [SMILES: COc1ccc(C(=O)N2CCc3nc(-c4ccccn4)ncc3C2)cn1]

A mixture of 2-(2-pyridyl)-5,6,7,8-tetrahydropyrido[4,3-d]pyrimidine hydrochloride (300 mg, 0.92 mmol, the product of step 3 in Example 1), 6-methoxypyridine-3-carboxylic acid (282 mg, 1.84 mmol), HATU (699 mg, 1.84 mmol) and DIPEA (595 mg, 4.6 mmol) in DMF (5 mL) was stirred at rt overnight. The resulting mixture was poured into water (5 mL) and extracted with EA three times. The combined organic layer was concentrated in vacuo and the residue was purified by prep-HPLC to give (6-methoxy-3-pyridyl)-[2-(2-pyridyl)-7,8-dihydro-5H-pyrido[4,3-d]pyrimidin-6-yl] methanone (90 mg) as light yellow solid. $^1$H NMR (400 MHz, CDCl$_3$) δ: 8.89 (d, 1H), 8.70 (br. s., 1H), 8.54 (d, 1H), 8.38 (d, 1H), 7.86-8.03 (m, 1H), 7.77 (dd, 1H), 7.39-7.53 (m, 1H), 6.85 (d, 1H), 4.93 (br. s., 2H), 3.83-4.21 (m, 5H), 3.25 (s, 2H). MS obsd. (ESI$^+$) [(M+H)$^+$]: 348.

Example 37

(3,5-Difluorophenyl)-[2-(2-pyridyl)-7,8-dihydro-5H-pyrido[4,3-d]pyrimidin-6-yl]methanone

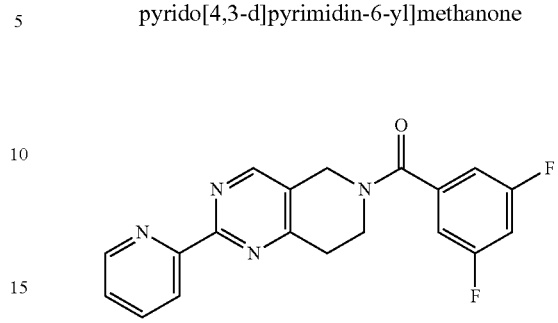

A mixture of 2-(2-pyridyl)-5,6,7,8-tetrahydropyrido[4,3-d]pyrimidine hydrochloride (300 mg, 0.92 mmol, the product of step 3 in Example 1), 3,5-difluorobenzoic acid (291 mg, 1.84 mmol), HATU (699 mg, 1.84 mmol) and DIPEA (595 mg, 4.6 mmol) in DMF (5 mL) was stirred at rt overnight. The resulting mixture was poured into water (5 mL) and extracted with EA three times. The combined organic layer was concentrated in vacuo and the residue was purified by prep-HPLC to give (3,5-difluorophenyl)-[2-(2-pyridyl)-7,8-dihydro-5H-pyrido[4,3-d]pyrimidin-6-yl] methanone (50 mg) as light yellow solid. $^1$H NMR (400 MHz, CDCl$_3$) δ: 8.37-8.96 (m, 3H), 7.90 (td, 1H), 7.45 (ddd, 1H), 6.79-7.14 (m, 3H), 4.97 (br. s., 2H), 3.82 (br. s., 2H), 3.20 (br. s., 2H). MS obsd. (ESI$^+$) [(M+H)$^+$]: 353.

Example 38

(3-Fluoro-5-methoxy-phenyl)-[2-(2-pyridyl)-7,8-dihydro-5H-pyrido[4,3-d]pyrimidin-6-yl]methanone

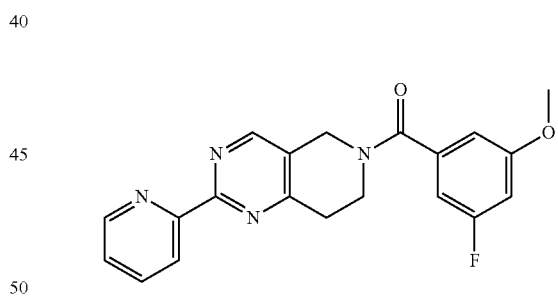

A mixture of 2-(2-pyridyl)-5,6,7,8-tetrahydropyrido[4,3-d]pyrimidine hydrochloride (300 mg, 0.92 mmol, the product of step 3 in Example 1), 3-fluoro-5-methoxy-benzoic acid (313 mg, 1.84 mmol), HATU (699 mg, 1.84 mmol) and DIPEA (595 mg, 4.6 mmol) in DMF (5 mL) was stirred at rt overnight. Then the resulting mixture was poured into water (5 mL) and extracted with EA (20 mL) three times. The combined organic layer was concentrated in vacuo and the residue was purified by prep-HPLC to give (3-fluoro-5-methoxy-phenyl)-[2-(2-pyridyl)-7,8-dihydro-5H-pyrido[4,3-d]pyrimidin-6-yl]methanone (90 mg) as light yellow solid. $^1$H NMR (400 MHz, CDCl$_3$) δ: 8.85 (d, 1H), 8.60-8.79 (m, 1H), 8.51 (d, 1H), 7.88 (td, 1H), 7.42 (dd, 1H), 6.56-6.89 (m, 3H), 4.52-5.10 (m, 2H), 3.84 (s, 5H), 3.19 (br. s., 2H). MS obsd. (ESI$^+$) [(M+H)$^+$]: 365.

Example 39

(4-Methoxyphenyl)-[2-(2-pyridyl)-7,8-dihydro-5H-pyrido[4,3-d]pyrimidin-6-yl]methanone

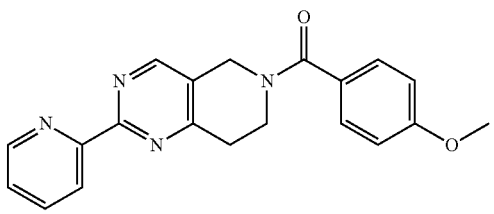 [SMILES: COc1ccc(C(=O)N2CCc3nc(-c4ccccn4)ncc3C2)cc1]

A mixture of 2-(2-pyridyl)-5,6,7,8-tetrahydropyrido[4,3-d]pyrimidine hydrochloride (300 mg, 0.92 mmol, the product of step 3 in Example 1), 4-methoxybenzoic acid (280 mg, 1.84 mmol), HATU (699 mg, 1.84 mmol) and DIPEA (595 mg, 4.6 mmol) in DMF (5 mL) was stirred at rt overnight. Then the resulting mixture was poured into water (5 mL) and extracted with EA three times. The combined organic layer was concentrated in vacuo and the residue was purified by prep-HPLC to give (4-methoxyphenyl)-[2-(2-pyridyl)-7,8-dihydro-5H-pyrido[4,3-d]pyrimidin-6-yl]methanone (55 mg) as light yellow solid. $^1$H NMR (400 MHz, CDCl$_3$) δ: 8.86 (dd, 1H), 8.58-8.73 (m, 1H), 8.52 (d, 1H), 7.89 (td, 1H), 7.38-7.54 (m, 3H), 6.92-7.04 (m, 2H), 4.90 (br. s., 2H), 3.77-4.07 (m, 5H), 3.21 (t, 2H). MS obsd. (ESI$^+$) [(M+H)$^+$]: 347.

Example 40

[3-Chloro-4-(3-methoxypropoxy)phenyl]-(5-methyl-2-pyrimidin-2-yl-7,8-dihydro-5H-pyrido[4,3-d]pyrimidin-6-yl)methanone

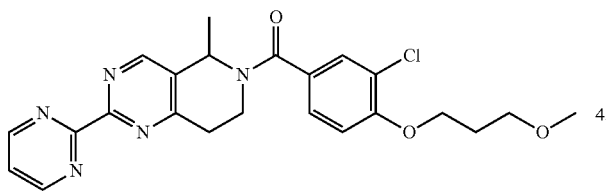

Step 1: Preparation of Tert-Butyl 5-methyl-2-pyrimidin-2-yl-7,8-dihydro-5H-pyrido[4,3-d]pyrimidine-6-carboxylate

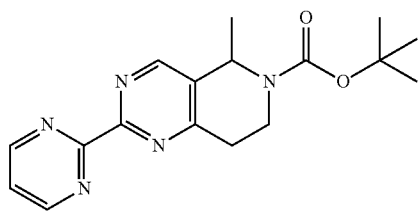 [SMILES: CC1c2cnc(-c3ncccn3)nc2CCN1C(=O)OC(C)(C)C]

A mixture of tert-butyl 2-methyl-4-oxo-piperidine-1-carboxylate (2.3 g, 10.8 mmol) and DMFDMA (5 mL) was heated to 100° C. for 2 hrs. The mixture was concentrated in vacuo. The residue was dissolved in in EtOH (50 mL) and pyrimidine-2-carboximidamide hydrochloride (3.55 g, 22.4 mmol) and K$_2$CO$_3$ (3.86 g, 27.9 mmol) were added and the mixture was heated at 90° C. overnight. After being cooled to rt, the resulting mixture was concentrated in vacuo and the residue was purified by flash chromatography (eluting with DCM/MeOH=20:1, v:v) to give tert-butyl 5-methyl-2-pyrimidin-2-yl-7,8-dihydro-5H-pyrido[4,3-d]pyrimidine-6-carboxylate (2.5 g) as yellow solid.

Step 2: Preparation of 5-methyl-2-pyrimidin-2-yl-5,6,7,8-tetrahydropyrido[4,3-d]pyrimidine

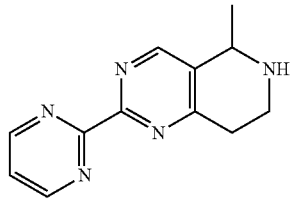

To a solution of tert-butyl 5-methyl-2-pyrimidin-2-yl-7,8-dihydro-5H-pyrido[4,3-d]pyrimidine-6-carboxylate (2.5 g, 7.64 mmol) in DCM (30 mL) was added CF$_3$COOH (10 ml). The resulting mixture was stirred for 2 hrs at rt and then concentrated in vacuo. The residue was diluted with saturated NaHCO$_3$ aqueous solution and extracted with a mixture of CHCl$_3$ and $^i$PrOH (50 mL, v/v=3/1) for three times. The combined organic layer was dried over anhydrous Na$_2$SO$_4$ and concentrated in vacuo. The residue was purified by prep-HPLC to give 5-methyl-2-pyrimidin-2-yl-5,6,7,8-tetrahydropyrido[4,3-d]pyrimidine (400 mg) as a yellow oil.

Step 3: Preparation of 3-chloro-4-(3-methoxypropoxy)benzoic Acid

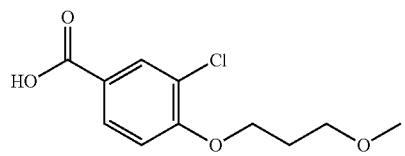 [SMILES: COCCCOc1ccc(C(=O)O)cc1Cl]

To a solution of methyl 3-chloro-4-(3-methoxypropoxy)benzoate (2.44 g, 9.43 mmol) in THF (10 mL), MeOH (30 mL) and water (5 mL) was added NaOH (1.13 g, 28.3 mmol). The resulting mixture was stirred overnight at rt, then acidified with 1N HCl to pH=2 and extracted with DCM (50 mL) for three times. The combined organic layer was dried over anhydrous Na$_2$SO$_4$ and concentrated in vacuo to give 3-chloro-4-(3-methoxypropoxy)benzoic acid (1.8 g) as yellow solid.

Step 4: Preparation of [3-chloro-4-(3-methoxy-propoxy)phenyl]-(5-methyl-2-pyrimidin-2-yl-7,8-dihydro-5H-pyrido[4,3-d]pyrimidin-6-yl)methanone

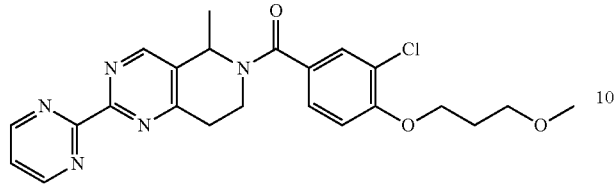

A mixture of 5-methyl-2-pyrimidin-2-yl-5,6,7,8-tetrahydropyrido[4,3-d]pyrimidine (279 mg, 1.23 mmol), 3-chloro-4-(3-methoxypropoxy)benzoic acid (250 mg, 1.02 mmol), HATU (583 mg, 1.53 mmol) and DIPEA (396 mg, 3.07 mmol) in DMF (10 ml) was stirred for 10 hrs at rt. The reaction mixture was poured into H$_2$O (50 mL) and extracted with a mixture of DCM and methanol (v/v=4/1) (50 mL) for three times. The combined organic layer was dried over anhydrous Na$_2$SO$_4$ and concentrated in vacuo. The residue was purified by prep-HPLC to give [3-chloro-4-(3-methoxypropoxy)phenyl]-(5-methyl-2-pyrimidin-2-yl-7,8-dihydro-5H-pyrido[4,3-d]pyrimidin-6-yl)methanone (114 mg) as light yellow solid. $^1$H NMR (400 MHz, CDCl$_3$) δ: 9.04 (d, 2H), 8.70-8.92 (m, 1H), 7.49-7.53 (m, 1H), 7.46 (s, 1H), 7.32 (s, 1H), 7.01 (d, 1H), 5.68-6.25 (m, 1H), 4.19 (s, 2H), 3.62 (s, 2H), 3.37 (s, 3H), 3.05-3.32 (m, 2H), 1.83-2.21 (m, 4H), 1.66 (d, 3H). MS obsd. (ESI$^+$) [(M+H)$^+$]: 454.

Example 41

[5-Methyl-2-(2-pyridyl)-7,8-dihydro-5H-pyrido[4,3-d]pyrimidin-6-yl]-(4-methyl-2-thienyl)methanone

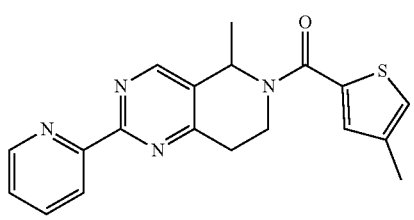 [SMILES: Cc1csc(C(=O)N2CCc3nc(-c4ccccn4)ncc3C2C)c1]

To a solution of 4-methylthiophene-2-carboxylic acid (214 mg, 1.5 mmol), 5-methyl-2-(2-pyridyl)-5,6,7,8-tetrahydropyrido[4,3 d]pyrimidine trifluoroacetic acid salt (227 mg, 1.0 mmol, the product of step 2 in Example 34) in anhydrous DMF (10 mL) was added DIPEA (258 mg, 2.0 mmol) HATU (762 mg, 2.0 mmol). The resulting mixture was stirred for 8 hrs at rt, then poured into water (50 mL), and extracted with EA (100 mL) twice. The combined organic layer was washed with water and brine, dried over anhydrous Na$_2$SO$_4$ and concentrated in vacuo. The residue was purified by prep-HPLC to provide [5-methyl-2-(2-pyridyl)-7,8-dihydro-5H-pyrido[4,3-d]pyrimidin-6-yl]-(4-methyl-2-thienyl)methanone (45 mg) as a light yellow solid. $^1$H NMR (400 MHz, CDCl$_3$) δ: 8.76 (m, 1H), 8.60 (s, 1H), 8.42 (m, 1H), 7.79 (m, 1H), 7.33 (m, 1H), 7.13 (s, 1H), 7.00 (s, 1H), 5.65 (br s, 1H), 4.56 (br s, 1H), 3.45 (br s, 1H), 3.05-3.25 (m, 2H), 2.20-2.24 (m, 3H), 1.38-1.44 (d, 3H). MS obsd. (ESI$^+$) [(M+H)$^+$]: 351.

Example 42

(5-Chloro-2-thienyl)-[5-methyl-2-(2-pyridyl)-7,8-dihydro-5H-pyrido[4,3-d]pyrimidin-6-yl]methanone

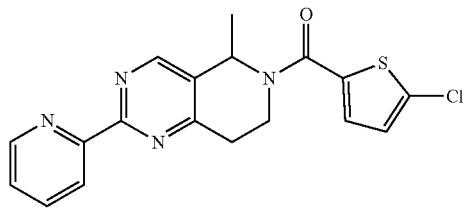 [SMILES: CC1c2cnc(-c3ccccn3)nc2CCN1C(=O)c1ccc(Cl)s1]

To a solution of 5-chlorothiophene-2-carboxylic acid (245 mg, 1.5 mmol), 5-methyl-2-(2-pyridyl)-5,6,7,8-tetrahydropyrido[4,3 d]pyrimidine trifluoroacetic acid salt (227 mg, 1.0 mmol, the product of step 2 in Example 34) in anhydrous DMF (10 mL) was added DIPEA (258 mg, 2.0 mmol) and HATU (762 mg, 2.0 mmol). The resulting mixture was stirred for 8 hrs at rt, then poured into water (50 mL), and extracted with EA (100 mL) twice. The combined organic layer was washed with water and brine, dried over anhydrous Na$_2$SO$_4$ and concentrated in vacuo. The residue was purified by prep-HPLC to provide (5-chloro-2-thienyl)-[5-methyl-2-(2-pyridyl)-7,8-dihydro-5H-pyrido[4,3-d]pyrimidin-6-yl]methanone (16 mg) as a light yellow solid. $^1$H NMR (400 MHz, CDCl$_3$) δ: 8.73-8.81 (m, 1H), 8.60 (s, 1H), 8.36-8.47 (m, 1H), 7.74-7.84 (m, 1H), 7.29-7.37 (m, 1H), 7.12 (d, 1H), 6.85 (d, 1H), 5.62 (br s, 1H), 4.53 (br d, 1H), 3.47 (br s, 1H), 3.05-3.24 (m, 2H), 1.60 (d, 3H). MS obsd. (ESI$^+$) [(M+H)$^+$]: 371.

Example 43

[5-Methyl-2-(2-pyridyl)-7,8-dihydro-5H-pyrido[4,3-d]pyrimidin-6-yl]-(5-methyl-2-thienyl)methanone

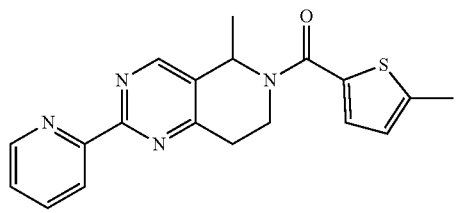 [SMILES: Cc1ccc(C(=O)N2CCc3nc(-c4ccccn4)ncc3C2C)s1]

To a solution of 5-methylthiophene-2-carboxylic acid (214 mg, 1.5 mmol), 5-methyl-2-(2-pyridyl)-5,6,7,8-tetrahydropyrido[4,3 d]pyrimidine trifluoroacetic acid salt (227 mg, 1.0 mmol, the product of step 2 in Example 34) in anhydrous DMF (10 mL) was added DIPEA (258 mg, 2.0 mmol) and HATU (762 mg, 2.0 mmol). The resulting mixture was stirred at rt for 8 hrs, then poured into water (50 mL) and extracted with EA (100 mL) twice. The organic layer was combined and washed with water and brine, dried over anhydrous Na$_2$SO$_4$ and concentrated in vacuo. The residue was purified by prep-HPLC to provide [5-methyl-2-(2-pyridyl)-7,8-dihydro-5H-pyrido[4,3-d]pyrimidin-6-yl]-(5-methyl-2-thienyl)methanone (60 mg) as an off-white solid. $^1$H NMR (400 MHz, CDCl$_3$) δ: 8.86 (m, 1H), 8.69 (s, 1H), 8.51 (d, 1H), 7.88 (m, 1H), 7.42 (m, 1H), 7.25 (s, 1H), 6.78 (dd, 1H), 5.75 (br s, 1H), 4.68 (br s, 1H), 3.54 (br s, 1H), 3.14-3.35 (m, 2H), 2.54-2.57 (m, 3H), 1.69 (d, 3H). MS obsd. (ESI⁺) [(M+H)⁺]: 351.

Example 44

[5-Methyl-2-(2-pyridyl)-7,8-dihydro-5H-pyrido[4,3-d]pyrimidin-6-yl]-(3-thienyl)methanone

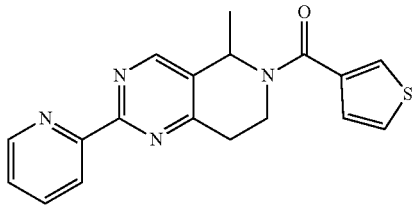 [SMILES: CC1c2cnc(-c3ccccn3)nc2CCN1C(=O)c1ccsc1]

To a solution of thiophene-3-carboxylic acid (193 mg, 1.5 mmol), 5-methyl-2-(pyridin-2-yl)-5,6,7,8-tetrahydropyrido[4,3-d]pyrimidine trifluoroacetic acid salt (227 mg, 1.0 mmol, the product of step 2 in Example 34) in anhydrous DMF (10 mL) was added DIPEA (258 mg, 2.0 mmol) and HATU (762 mg, 2.0 mmol). The resulting mixture was stirred for 8 hrs at rt, then poured into water (50 mL) and extracted with EA (100 mL) twice. The combined organic layer was washed with water and brine, dried over anhydrous Na₂SO₄ and concentrated in vacuo. The residue was purified by prep-HPLC to provide [5-methyl-2-(2-pyridyl)-7,8-dihydro-5H-pyrido[4,3-d]pyrimidin-6-yl]-(3-thienyl)methanone (55 mg) as an off-white solid. ¹H NMR (400 MHz, CDCl₃) δ: 8.76 (d, 1H), 8.60 (br s, 1H), 8.41 (d, 1H), 7.79 (m, 1H), 7.52 (dd, 1H), 7.30-7.36 (m, 2H), 7.15-7.20 (m, 1H), 5.80 (br s, 1H), 4.20 (br s, 1H), 3.26-3.53 (m, 1H), 3.02-3.19 (m, 2H), 1.51-1.61 (d, 3H). MS obsd. (ESI⁺) [(M+H)⁺]: 337.

Example 45

(4-Methyloxazol-5-yl)-[5-methyl-2-(2-pyridyl)-7,8-dihydro-5H-pyrido[4,3-d]pyrimidin-6-yl]methanone

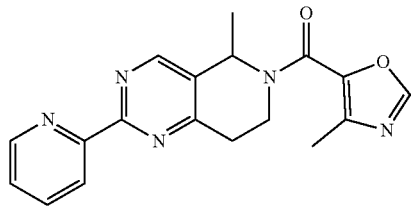 [SMILES: Cc1ncoc1C(=O)N1CCc2nc(-c3ccccn3)ncc2C1C]

To a solution of 4-methyloxazole-5-carboxylic acid (191 mg, 1.5 mmol), 5-methyl-2-(2-pyridyl)-5,6,7,8-tetrahydropyrido[4,3 d]pyrimidine trifluoroacetic acid salt (227 mg, 1.0 mmol, the product of step 2 in Example 34) in anhydrous DMF (10 mL) was added DIPEA (258 mg, 2.0 mmol) and HATU (762 mg, 2.0 mmol). The resulting mixture was stirred at rt for 8 hrs, then poured into water (50 mL) and extracted with EA (100 mL) twice. The combined organic layer was washed with water and brine, dried over anhydrous Na₂SO₄ and concentrated in vacuo and the residue was purified by flash chromatography (eluting with DCM/MeOH=20/1, v:v) to provide (4-methyloxazol-5-yl)-[5-methyl-2-(2-pyridyl)-7,8-dihydro-5H-pyrido[4,3-d]pyrimidin-6-yl]methanone (40 mg) as a light red solid. ¹H NMR (400 MHz, CDCl₃) δ: 8.86 (d, 1H), 8.71 (br s, 1H), 8.51 (d, 1H), 7.85-7.93 (m, 2H), 7.43 (m, 1H), 5.80 (br s, 1H), 4.31-4.63 (m, 1H), 3.44-3.78 (m, 1H), 3.13-3.34 (m, 2H), 2.49 (s, 3H), 1.70 (br s, 3H). MS obsd. (ESI⁺) [(M+H)⁺]: 336

Example 46

1H-ndol-6-yl-[5-methyl-2-(2-pyridyl)-7,8-dihydro-5H-pyrido[4,3-d]pyrimidin-6-yl]methanone

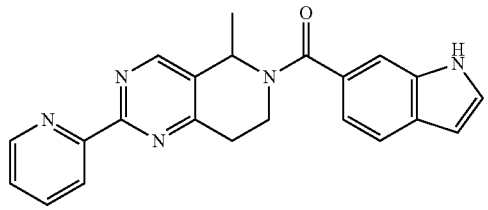 [SMILES: CC1c2cnc(-c3ccccn3)nc2CCN1C(=O)c1ccc2cc[nH]c2c1]

To a solution of 1H-indole-6-carboxylic acid (243 mg, 1.5 mmol), 5-methyl-2-(2-pyridyl)-5,6,7,8-tetrahydropyrido[4,3 d]pyrimidine trifluoroacetic acid salt (227 mg, 1.0 mmol, the product of step 2 in Example 34) in anhydrous DMF (10 mL) was added DIPEA (258 mg, 2.0 mmol) and HATU (762 mg, 2.0 mmol). The resulting mixture was stirred for 8 hrs, then poured into water (50 mL) and extracted with EA (100 mL) twice. The combined organic layer was washed with water and brine, dried over anhydrous Na₂SO₄ and concentrated in vacuo. The residue was purified by flash chromatography (eluting with DCM/MeOH=20/1, v:v) to provide 1H-indol-6-yl-[5-methyl-2-(2-pyridyl)-7,8-dihydro-5H-pyrido[4,3-d]pyrimidin-6-yl]methanone (40 mg) as a white solid. ¹H NMR (400 MHz, CDCl₃) δ: 9.06 (br s, 1H), 8.85 (d, 1H), 8.48-8.69 (m, 1H), 7.89 (t, 1H), 7.70 (d, 1H), 7.55 (s, 1H), 7.39-7.46 (m, 1H), 7.33-7.35 (m, 1H), 7.19 (dd, 1H), 6.60 (br s, 1H), 5.94 (br s, 1H), 4.02-4.47 (br s, 1H), 3.38-3.55 (m, 1H), 3.15-3.27 (m, 1H), 3.02-3.15 (m, 1H), 1.65 (d, 3H). MS obsd. (ESI⁺) [(M+H)⁺]: 370.

Example 47

1H-indazol-5-yl-[5-methyl-2-(2-pyridyl)-7,8-dihydro-5H-pyrido[4,3-d]pyrimidin-6-yl]methanone

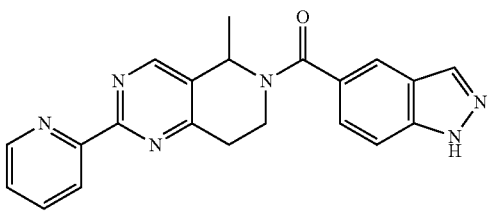 [SMILES: CC1c2cnc(-c3ccccn3)nc2CCN1C(=O)c1ccc2[nH]ncc2c1]

To a solution of 1H-indazole-5-carboxylic acid (244 mg, 1.5 mmol), 5-methyl-2-(2-pyridyl)-5,6,7,8-tetrahydropyrido[4,3 d]pyrimidine trifluoroacetic acid salt (227 mg, 1.0 mmol, the product of step 2 in Example 34) in anhydrous DMF (10 mL) was added DIPEA (258 mg, 2.0 mmol) HATU (762 mg, 2.0 mmol). The resulting mixture was stirred for 8 hrs, then poured into water (50 mL) and extracted with EA (100 mL) twice. The combined organic layer was washed with water and brine, dried over anhydrous Na₂SO₄ and concentrated in vacuo. The residue was purified by flash chromatography (eluting with DCM/MeOH=20/1, v:v) to provide 1H-indazol-5-yl-[5-methyl-2-(2-pyridyl)-7,8-dihydro-5H-pyrido[4,3-d]pyrimidin-6-yl]methanone (30 mg) as a white solid. $^1$H NMR (400 MHz, Methanol-d4) δ: 8.96 (br d, 1H), 8.82-8.92 (m, 1H), 8.61-8.82 (m, 1H), 8.16 (s, 1H), 8.11 (t, 1H), 7.92-8.08 (m, 1H), 7.67 (d, 1H), 7.51 (m, 1H), 5.95 (br s, 1H), 3.96-4.23 (m, 1H), 3.57-3.75 (m, 1H), 3.27-3.38 (m, 2H), 3.03-3.19 (m, 1H), 1.72 (d, 3H). MS obsd. (ESI⁺) [(M+H)⁺]: 371.

Example 48

Benzothiophen-2-yl-[5-methyl-2-(2-pyridyl)-7,8-dihydro-5H-pyrido[4,3-d]pyrimidin-6-yl]methanone

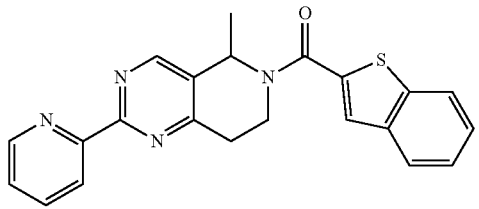 [SMILES: CC1c2cnc(-c3ccccn3)nc2CCN1C(=O)c1cc2ccccc2s1]

To a solution of benzothiophene-2-carboxylic acid (267 mg, 1.5 mmol), 5-methyl-2-(2-pyridyl)-5,6,7,8-tetrahydropyrido[4,3 d]pyrimidine trifluoroacetic acid salt (227 mg, 1.0 mmol, the product of step 2 in Example 34) in anhydrous DMF (10 mL) was added DIPEA (258 mg, 2.0 mmol) and HATU (762 mg, 2.0 mmol). The mixture was stirred at rt for 8 hrs. The mixture was poured into water (50 mL) and extracted with EA (100 mL) twice. The combined organic layer was washed with water and brine, dried over anhydrous Na₂SO₄ and concentrated in vacuo and the residue was purified by flash chromatography to provide benzothiophen-2-yl-[5-methyl-2-(2-pyridyl)-7,8-dihydro-5H-pyrido[4,3-d]pyrimidin-6-yl]methanone (30 mg) as a light red powder. $^1$H NMR (400 MHz, Methanol-d4) δ: 8.72 (br s, 1H), 8.63 (d, 1H), 8.43 (d, 1H), 7.87-7.93 (m, 1H), 7.82-7.87 (m, 2H), 7.67 (s, 1H), 7.42-7.48 (m, 1H), 7.33-7.39 (m, 2H), 5.68 (br s, 1H), 4.50 (br s, 1H), 3.61 (br s, 1H), 3.01-3.18 (m, 2H), 1.64 (br d, 3H). MS obsd. (ESI⁺) [(M+H)⁺]: 387.

Example 49

[5-Methyl-2-(2-pyridyl)-7,8-dihydro-5H-pyrido[4,3-d]pyrimidin-6-yl]-(2-thienyl)methanone

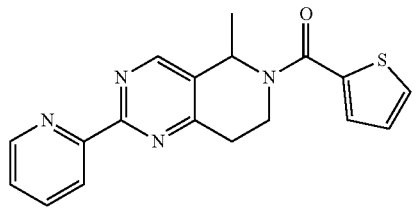 [SMILES: CC1c2cnc(-c3ccccn3)nc2CCN1C(=O)c1cccs1]

To a solution of thiophene-2-carboxylic acid (193 mg, 1.5 mmol), 5-methyl-2-(2-pyridyl)-5,6,7,8-tetrahydropyrido[4,3 d]pyrimidine trifluoroacetic acid salt (227 mg, 1.0 mmol, the product of step 2 in Example 34) in anhydrous DMF (10 mL) was added DIPEA (258 mg, 2.0 mmol) and HATU (762 mg, 2.0 mmol). The resulting mixture was stirred at rt for 8 hrs, then poured into water (50 mL) and extracted with EA (100 mL) twice. The combined organic layer was washed with water and brine, dried over anhydrous Na₂SO₄ and concentrated in vacuo. The residue was purified by prep-HPLC to provide [5-methyl-2-(2-pyridyl)-7,8-dihydro-5H-pyrido[4,3-d]pyrimidin-6-yl]-(2-thienyl)methanone (120 mg) as a yellow solid. $^1$H NMR (400 MHz, CDCl₃) δ: 8.76 (dd, 1H), 8.60 (s, 1H), 8.44 (d, 1H), 7.81 (m, 1H), 7.43 (dd, 1H), 7.30-7.38 (m, 2H), 7.03 (dd, 1H), 5.66 (br s, 1H), 4.53 (br s, 1H), 3.46 (br s, 1H), 3.04-3.25 (m, 2H), 1.60 (d, 3H). MS obsd. (ESI⁺) [(M+H)⁺]: 337.

Example 50

[5-Methyl-2-(2-pyridyl)-7,8-dihydro-5H-pyrido[4,3-d]pyrimidin-6-yl]-(3-methyl-2-thienyl)methanone

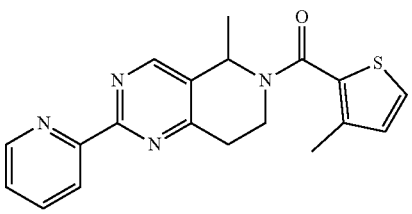 [SMILES: Cc1ccsc1C(=O)N1CCc2nc(-c3ccccn3)ncc2C1C]

To a solution of 3-methylthiophene-2-carboxylic acid (214 mg, 1.5 mmol), 5-methyl-2-(2-pyridyl)-5,6,7,8-tetrahydropyrido[4,3 d]pyrimidine trifluoroacetic acid salt (227 mg, 1.0 mmol, the product of step 2 in Example 34) in anhydrous DMF (10 mL) was added DIPEA (258 mg, 2.0 mmol) and HATU (762 mg, 2.0 mmol). The resulting mixture was stirred at rt for 8 hrs, then poured into water (50 mL) and extracted with EA (100 mL) twice. The combined organic layer was washed with water and brine, dried over anhydrous Na₂SO₄ and concentrated in vacuo. The residue was purified by prep-HPLC to provide [5-methyl-2-(2-pyridyl)-7,8-dihydro-5H-pyrido[4,3-d]pyrimidin-6-yl]-(3-methyl-2-thienyl)methanone (120 mg) as a yellow solid. $^1$H NMR (400 MHz, CDCl₃) δ: 8.72-8.80 (m, 1H), 8.60 (s, 1H), 8.44 (d, 1H), 7.82 (m, 1H), 7.36 (m, 1H), 7.20-7.27 (m, 1H), 6.82 (d, 1H), 5.65 (br s, 1H), 4.28 (br s, 1H), 3.42 (br t, 1H), 2.98-3.18 (m, 2H), 2.19 (s, 3H), 1.56 (d, 3H). MS obsd. (ESI⁺) [(M+H)⁺]: 351

Example 51

[5-Methyl-2-(2-pyridyl)-7,8-dihydro-5H-pyrido[4,3-d]pyrimidin-6-yl]-thiazol-2-yl-methanone

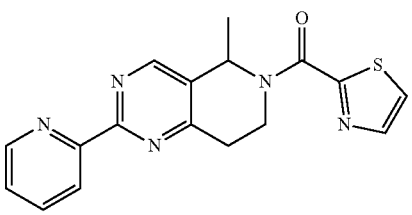 [SMILES: CC1c2cnc(-c3ccccn3)nc2CCN1C(=O)c1nccs1]

To a solution of thiazole-2-carboxylic acid (194 mg, 1.5 mmol), 5-methyl-2-(2-pyridyl)-5,6,7,8-tetrahydropyrido[4,3 d]pyrimidine trifluoroacetic acid salt (227 mg, 1.0 mmol, the product of step 2 in Example 34) in anhydrous DMF (10 mL) was added DIPEA (258 mg, 2.0 mmol) and HATU (762 mg, 2.0 mmol). The resulting mixture was stirred at rt for 8 hrs, then poured into water (50 mL) and extracted with EA (100 mL) twice. The combined organic layer was washed with water and brine, dried over anhydrous $Na_2SO_4$ and concentrated in vacuo. The residue was purified by flash chromatography (eluting with DCM/MeOH=20/1, v:v) to provide [5-methyl-2-(2-pyridyl)-7,8-dihydro-5H-pyrido[4,3-d]pyrimidin-6-yl]-thiazol-2-yl-methanone (102 mg) as a yellow solid. $^1$H NMR (400 MHz, $CDCl_3$) δ: 8.78 (br d, 1H), 8.65 (d, 1H), 8.44 (br d, 1H), 7.85-7.93 (m, 1H), 7.80 (m, 1H), 7.52 (d, 1H), 7.34 (dd, 1H), 6.77-6.87 (m, 0.5H), 5.77-5.88 (m, 1H), 4.88-4.99 (m, 0.5H), 3.49-3.61 (m, 0.5H), 3.10-3.35 (m, 2.5H), 1.70 (d, 1H), 1.55-1.66 (d, 2H). MS obsd. ($ESI^+$) [$(M+H)^+$]: 338.

Example 52

[5-Methyl-2-(2-pyridyl)-7,8-dihydro-5H-pyrido[4,3-d]pyrimidin-6-yl]-(2-methylthiazol-5-yl)methanone

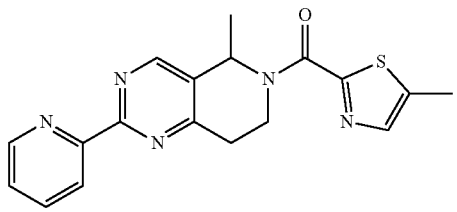 [SMILES: Cc1cnc(C(=O)N2CCc3nc(-c4ccccn4)ncc3C2C)s1]

To a solution of 2-methylthiazole-5-carboxylic acid (215 mg, 1.5 mmol), 5-methyl-2-(2-pyridyl)-5,6,7,8-tetrahydropyrido[4,3 d]pyrimidine trifluoroacetic acid salt (227 mg, 1.0 mmol, the product of step 2 in Example 34) in anhydrous DMF (10 mL) was added DIPEA (258 mg, 2.0 mmol) and HATU (762 mg, 2.0 mmol). The mixture was stirred at rt for 8 hrs. The mixture was poured into water (50 mL) and the aqueous solution was extracted with EA (100 mL) twice. The organic layer was combined and washed with water and brine, dried over anhydrous $Na_2SO_4$ and concentrated in vacuo. The residue was purified by flash chromatography (eluting with DCM/MeOH=20/1, v:v) to provide [5-methyl-2-(2-pyridyl)-7,8-dihydro-5H-pyrido[4,3-d]pyrimidin-6-yl]-(2-methylthiazol-5-yl)methanone (40 mg) as a yellow solid. $^1$H NMR (400 MHz, $CDCl_3$) δ: 8.76 (d, 1H), 8.61 (br s, 1H), 8.43 (d, 1H), 7.78-7.84 (m, 2H), 7.34 (m, 1H), 5.64 (br s, 1H), 4.47 (br s, 1H), 3.50 (br s, 1H), 3.05-3.23 (m, 2H), 2.69 (s, 3H), 1.60 (d, 3H). MS obsd. ($ESI^+$) [$(M+H)^+$]: 352.

Example 53

(5-Bromo-2-thienyl)-[5-methyl-2-(2-pyridyl)-7,8-dihydro-5H-pyrido[4,3-d]pyrimidin-6-yl]methanone

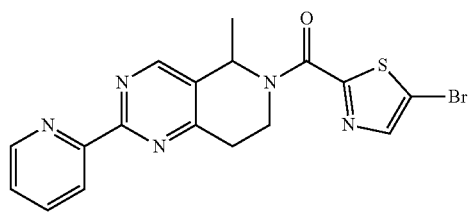 [SMILES: CC1c2cnc(-c3ccccn3)nc2CCN1C(=O)c1ncc(Br)s1]

To a solution of 5-bromothiophene-2-carboxylic acid (312 mg, 1.5 mmol), 5-methyl-2-(2-pyridyl)-5,6,7,8-tetrahydropyrido[4,3 d]pyrimidine trifluoroacetic acid salt (227 mg, 1.0 mmol, the product of step 2 in Example 34) in anhydrous DMF (10 mL) was added DIPEA (258 mg, 2.0 mmol) and HATU (762 mg, 2.0 mmol). The resulting mixture was stirred at rt for 8 hrs, then poured into water (50 mL) and extracted with EA (100 mL) twice. The combined organic layer was washed with water and brine, dried over anhydrous $Na_2SO_4$ and concentrated in vacuo. The residue was purified by prep-HPLC to provide (5-bromo-2-thienyl)-[5-methyl-2-(2-pyridyl)-7,8-dihydro-5H-pyrido[4,3-d]pyrimidin-6-yl]methanone (160 mg) as a yellow solid. $^1$H NMR (400 MHz, DMSO-d6) δ: 9.03 (s, 1H), 8.86 (d, 1H), 8.66 (d, 1H), 8.41 (m, 1H), 7.90 (m, 1H), 7.44 (d, 1H), 7.33 (d, 1H), 5.68 (br s, 1H), 4.45 (br s, 1H), 3.64 (br s, 1H), 3.27 (br s, 1H), 3.05 (br dd, 1H), 1.64 (d, 3H). MS obsd. ($ESI^+$) [$(M+H)^+$]: 415.

Example 54

[5-Methyl-2-(2-pyridyl)-7,8-dihydro-5H-pyrido[4,3-d]pyrimidin-6-yl]-thiazol-5-yl-methanone

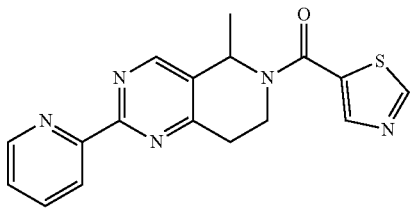 [SMILES: CC1c2cnc(-c3ccccn3)nc2CCN1C(=O)c1cncs1]

To a solution of thiazole-5-carboxylic acid (194 mg, 1.5 mmol), 5-methyl-2-(2-pyridyl)-5,6,7,8-tetrahydropyrido[4,3 d]pyrimidine trifluoroacetic acid salt (227 mg, 1.0 mmol, the product of step 2 in Example 34) in anhydrous DMF (10 mL) was added DIPEA (258 mg, 2.0 mmol) and HATU (762 mg, 2.0 mmol). The resulting mixture was stirred at rt for 8 hrs, then poured into water (50 mL) and extracted with EA (100 mL) twice. The combined organic layer was washed with water and brine, dried over anhydrous $Na_2SO_4$ and concentrated in vacuo. The residue was purified by flash chromatography (eluting with DCM/MeOH=20/1, v:v) to provide [5-methyl-2-(2-pyridyl)-7,8-dihydro-5H-pyrido[4,3-d]pyrimidin-6-yl]-thiazol-5-yl-methanone (28 mg) as a yellow solid. $^1$H NMR (400 MHz, DMSO-d6) δ: 9.30 (s, 1H), 9.02 (br s, 1H), 8.77-8.94 (m, 1H), 8.62 (m, 1H), 8.32-8.40 (m, 2H), 7.85 (m, 1H), 5.74 (br s, 1H), 4.17-4.39 (br s, 1H), 3.54-3.84 (br s, 1H), 3.15-3.44 (br s, 1H), 2.98-3.13 (m, 1H), 1.64 (d, 3H). MS obsd. ($ESI^+$) [$(M+H)^+$]: 338.

Example 55

[5-Methyl-2-(2-pyridyl)-7,8-dihydro-5H-pyrido[4,3-d]pyrimidin-6-yl]-(5-methylthiazol-2-yl)methanone

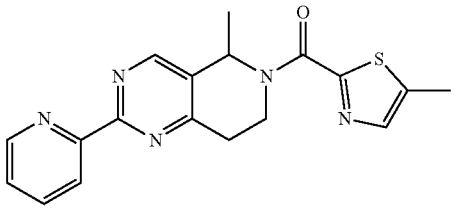 [SMILES: Cc1cnc(C(=O)N2CCc3nc(-c4ccccn4)ncc3C2C)s1]

To a solution of 5-methylthiazole-2-carboxylic acid (215 mg, 1.5 mmol), 5-methyl-2-(2-pyridyl)-5,6,7,8-tetrahydropyrido[4,3 d]pyrimidine trifluoroacetic acid salt (227 mg, 1.0 mmol, the product of step 2 in Example 34) in anhydrous DMF (10 mL) was added DIPEA (258 mg, 2.0 mmol) and HATU (762 mg, 2.0 mmol). The resulting mixture was stirred at rt for 8 hrs, then poured into water (50 mL) extracted with EA (100 mL) twice. The combined organic layer was washed with water and brine, dried over anhydrous Na$_2$SO$_4$ and concentrated in vacuo. The residue was purified by flash chromatography (eluting with DCM/MeOH=20/1, v:v) to provide [5-methyl-2-(2-pyridyl)-7,8-dihydro-5H-pyrido[4,3-d]pyrimidin-6-yl]-(5-methylthiazol-2-yl)methanone (35 mg) as a white solid. $^1$H NMR (400 MHz, CDCl$_3$) δ: 8.90 (br d, 1H), 8.73 (br s, 1H), 8.54 (br d, 1H), 7.93 (m, 1H), 7.60 (br d, 1H), 7.43-7.50 (m, 1H), 6.83-6.95 (m, 0.5H), 5.82-5.97 (m, 1H), 4.94-5.06 (m, 0.5H), 3.48-3.71 (m, 0.5H), 3.16-3.46 (m, 2.5H), 2.52-2.57 (m, 3H), 1.74 (d, 1H), 1.62-1.70 (m, 2H). MS obsd. (ESI$^+$) [(M+H)$^+$]: 352.

Example: 56

1H-Imidazol-2-yl-[5-methyl-2-(2-pyridyl)-7,8-dihydro-5H-pyrido[4,3-d]pyrimidin-6-yl]methanone

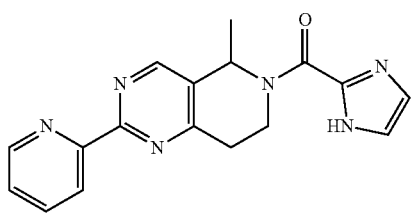 [SMILES: CC1c2cnc(-c3ccccn3)nc2CCN1C(=O)c1ncc[nH]1]

A mixture of 5-methyl-2-(2-pyridyl)-5,6,7,8-tetrahydropyrido[4,3 d]pyrimidine trifluoroacetic acid salt (100 mg, 442 μmol, the product of step 2 in Example 34), 1H-imidazole-2-carboxylic acid (74.3 mg, 663 μmol), HATU (336 mg, 884 μmol) and DIPEA (171 mg, 1.33 mmol) in DMF (5 mL) was stirred at rt overnight. The resulting mixture was poured into water and extracted with DCM (30 ml) twice. The combined organic layer was dried over anhydrous Na$_2$SO$_4$ and concentrated in vacuo and the residue was purified by prep-HPLC to give 1H-imidazol-2-yl-[5-methyl-2-(2-pyridyl)-7,8-dihydro-5H-pyrido[4,3-d]pyrimidin-6-yl]methanone (76 mg) as off-white solid. $^1$H NMR (400 MHz, Methanol-d4) δ: 8.59-8.81 (m, 2H), 8.36-8.48 (m, 1H), 7.84-7.97 (m, 1H), 7.36-7.49 (m, 1H), 6.99-7.28 (m, 2H), 6.78-6.94 (m, 0.3H), 5.50-5.88 (m, 1.2H), 4.80-5.01 (m, 0.5H), 3.23-3.69 (m, 1.5H), 3.03 (br d, 1.5H), 1.45-1.77 (m, 3H). MS obsd. (ESI$^+$) [(M+H)$^+$]: 321.

Example 57

(1-Methylimidazol-2-yl)-[5-methyl-2-(2-pyridyl)-7,8-dihydro-5H-pyrido[4,3-d]pyrimidin-6-yl]methanone

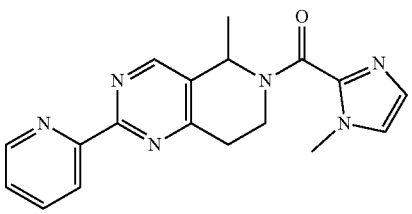 [SMILES: CC1c2cnc(-c3ccccn3)nc2CCN1C(=O)c1nccn1C]

A mixture of 5-methyl-2-(2-pyridyl)-5,6,7,8-tetrahydropyrido[4,3 d]pyrimidine trifluoroacetic acid salt (100 mg, 442 μmol, the product of step 2 in Example 34), 1-methylimidazole-2-carboxylic acid (83.6 mg, 663 μmol), HATU (336 mg, 884 μmol) and DIPEA (171 mg, 1.33 mmol) in DMF (5 mL) was stirred overnight at rt. The resulting mixture was poured into water and extracted with DCM (30 mL) twice. The combined organic layer was concentrated in vacuo and the residue was purified by prep-HPLC to give (1-methylimidazol-2-yl)-[5-methyl-2-(2-pyridyl)-7,8-dihydro-5H-pyrido[4,3-d]pyrimidin-6-yl]methanone (69 mg) as a light yellow solid. $^1$H NMR (400 MHz, Methanol-d4) δ: 8.51-8.80 (m, 2H), 8.33-8.43 (m, 1H), 7.80-7.92 (m, 1H), 7.34-7.47 (m, 1H), 7.07-7.18 (m, 1H), 6.97 (d, 1H), 5.66-5.86 (m, 1H), 4.66-4.75 (m, 0.4H), 4.49-4.60 (m, 0.6H), 3.74 (s, 3H), 3.48-3.63 (m, 0.7H), 3.23-3.41 (m, 1H), 2.88-3.15 (m, 1.3H), 1.56 (br d, 3H). MS obsd. (ESI$^+$) [(M+H)$^+$]: 335.

Example 58

(5-Methoxy-2-thienyl)-[5-methyl-2-(2-pyridyl)-7,8-dihydro-5H-pyrido[4,3-d]pyrimidin-6-yl]methanone

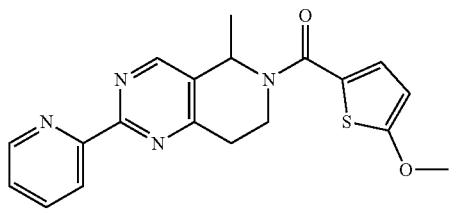 [SMILES: COc1ccc(C(=O)N2CCc3nc(-c4ccccn4)ncc3C2C)s1]

A mixture of 5-methyl-2-(2-pyridyl)-5,6,7,8-tetrahydropyrido[4,3 d]pyrimidine trifluoroacetic acid salt (100 mg, 442 μmol, the product of step 2 in Example 34), 5-methoxythiophene-2-carboxylic acid (105 mg, 663 μmol), HATU (336 mg, 884 μmol) and DIPEA (171 mg, 1.33 mmol) in DMF (5 mL) was stirred overnight at rt. Then the resulting mixture was poured into water and extracted with DCM (30 mL) twice. The combined organic layer was dried over anhydrous Na$_2$SO$_4$ and concentrated in vacuo. The residue was purified by prep-HPLC to give (5-methoxy-2-thienyl)-

[5-methyl-2-(2-pyridyl)-7,8-dihydro-5H-pyrido[4,3-d]pyrimidin-6-yl]methanone (102 mg) as a light yellow solid. ¹H NMR (400 MHz, DMSO-d6) δ: 8.78-8.89 (m, 1H), 8.61-8.73 (m, 1H), 8.22-8.35 (m, 1H), 7.83-7.96 (m, 1H), 7.41-7.54 (m, 1H), 7.23-7.32 (m, 1H), 6.28-6.38 (m, 1H), 5.49-5.62 (m, 1H), 4.33-4.49 (m, 1H), 3.86 (s, 3H), 3.43-3.63 (m, 1H), 3.06-3.21 (m, 1H), 2.84-2.99 (m, 1H), 1.54 (br d, 3H). MS obsd. (ESI⁺) [(M+H)⁺]: 367.

Example 59

[5-Methyl-2-(2-pyridyl)-7,8-dihydro-5H-pyrido[4,3-d]pyrimidin-6-yl]-[4-(trifluoromethyl)thiazol-2-yl]methanone

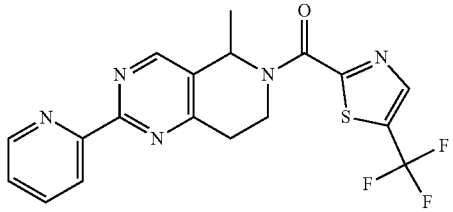 [SMILES: CC1c2cnc(-c3ccccn3)nc2CCN1C(=O)c1ncc(C(F)(F)F)s1]

A mixture of 5-methyl-2-(2-pyridyl)-5,6,7,8-tetrahydropyrido[4,3 d]pyrimidine trifluoroacetic acid salt (130 mg, 575 µmol, the product of step 2 in Example 34), 4-(trifluoromethyl)thiazole-2-carboxylic acid (170 mg, 862 µmol), HATU (437 mg, 1.15 mmol) and DIPEA (223 mg, 1.72 mmol) was stirred overnight at rt. Then the resulting mixture was poured into water and extracted with DCM (30 mL) twice. The combined organic layer was dried over anhydrous Na₂SO₄ and concentrated in vacuo. The residue was purified by prep-HPLC to give [5-methyl-2-(2-pyridyl)-7,8-dihydro-5H-pyrido[4,3-d]pyrimidin-6-yl]-[4-(trifluoromethyl)thiazol-2-yl]methanone (130 mg) as a solid. ¹H NMR (400 MHz, METHANOL-d4) δ: 8.92 (s, 2H), 8.81 (br d, 1H), 8.60-8.69 (m, 1H), 8.40 (s, 1H), 8.02-8.10 (m, 1H), 6.43-6.61 (m, 0.4H), 5.76-5.93 (m, 0.6H), 5.42-5.59 (m, 0.6H), 4.73-4.79 (m, 0.4H), 3.62-3.77 (m, 0.6H), 3.27-3.51 (m, 1H), 3.08-3.20 (m, 1.4H), 1.52-1.82 (m, 3H). MS obsd. (ESI⁺) [(M+H)⁺]: 406.

Example 60

[5-Methyl-2-(2-pyridyl)-7,8-dihydro-5H-pyrido[4,3-d]pyrimidin-6-yl]-oxazol-2-yl-methanone

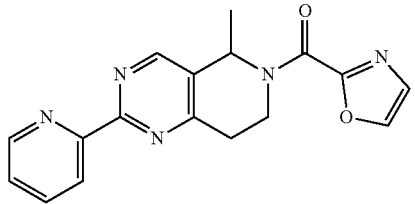 [SMILES: CC1c2cnc(-c3ccccn3)nc2CCN1C(=O)c1ncco1]

A mixture of 5-methyl-2-(2-pyridyl)-5,6,7,8-tetrahydropyrido[4,3 d]pyrimidine trifluoroacetic acid salt (100 mg, 442 µmol, the product of step 2 in Example 34), oxazole-2-carboxylic acid (75 mg, 663 µmol), HATU (336 mg, 884 µmol) and DIPEA (171 mg, 1.33 mmol) was stirred overnight at rt. Then the resulting mixture was poured into water and extracted with DCM (30 mL) twice. The organic layer was dried over anhydrous Na₂SO₄ and concentrated in vacuo. The residue was purified by prep-HPLC to give [5-methyl-2-(2-pyridyl)-7,8-dihydro-5H-pyrido[4,3-d]pyrimidin-6-yl]-oxazol-2-yl-methanone (88 mg) as a light yellow solid. 1H NMR (400 MHz, Methanol-d4) δ: 8.58-8.80 (m, 2H), 8.36-8.48 (m, 1H), 7.98-8.06 (m, 1H), 7.82-7.95 (m, 1H), 7.39-7.50 (m, 1H), 7.28-7.37 (m, 1H), 6.16-6.28 (m, 0.4H), 5.70-5.82 (m, 0.6H), 5.03-5.15 (m, 0.5H), 4.78-4.88 (m, 1H), 3.55-3.70 (m, 0.5H), 3.33-3.47 (m, 0.4H), 3.23-3.32 (m, 0.6H), 2.97-3.12 (m, 1H), 1.51-1.76 (m, 3H). MS obsd. (ESI⁺) [(M+H)⁺]: 322.

Example 61

(4,5-Dimethylthiazol-2-yl)-[5-methyl-2-(2-pyridyl)-7,8-dihydro-5H-pyrido[4,3-d]pyrimidin-6-yl]methanone

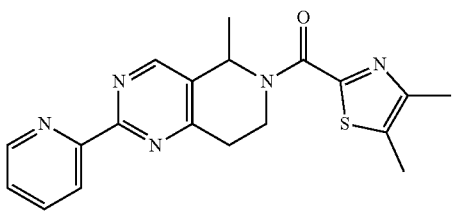 [SMILES: Cc1nc(C(=O)N2CCc3nc(-c4ccccn4)ncc3C2C)sc1C]

A mixture of 5-methyl-2-(2-pyridyl)-5,6,7,8-tetrahydropyrido[4,3 d]pyrimidine trifluoroacetic acid salt (100 mg, 442 µmol, the product of step 2 in Example 34), 4,5-dimethylthiazole-2-carboxylic acid (69.5 mg, 442 µmol), HATU (336 mg, 884 µmol) and DIPEA (171 mg, 1.33 mmol) was stirred overnight at rt. Then the resulting mixture then was poured into water and extracted with DCM (30 mL) twice. The combined organic layer was dried over anhydrous Na₂SO₄ and concentrated in vacuo. The residue was purified by prep-HPLC to give (4,5-dimethylthiazol-2-yl)-[5-methyl-2-(2-pyridyl)-7,8-dihydro-5H-pyrido[4,3-d]pyrimidin-6-yl]methanone (28 mg) as a light yellow solid. ¹H NMR (400 MHz, Methanol-d4) δ: 8.54-8.79 (m, 2H), 8.33-8.47 (m, 1H), 7.88 (br d, 1H), 7.36-7.49 (m, 1H), 6.56-6.74 (m, 0.3H), 5.49-5.81 (m, 1.2H), 4.62-4.77 (m, 0.5H), 3.45-3.69 (m, 0.6H), 3.27-3.44 (m, 0.4H), 2.91-3.20 (m, 2H), 2.32 (d, 6H), 1.48-1.77 (m, 3H). MS obsd. (ESI⁺) [(M+H)⁺]: 366.

Example 62

(1-Methylindazol-3-yl)-(5-methyl-2-pyrimidin-2-yl-7,8-dihydro-5H-pyrido[4,3-d]pyrimidin-6-yl)methanone

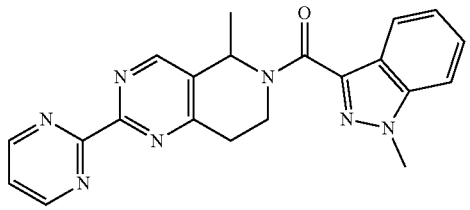 [SMILES: CC1c2cnc(-c3ncccn3)nc2CCN1C(=O)c1nn(C)c2ccccc12]

A mixture of 1-methyl-1H-indazole-3-carboxylic acid (264 mg, 1.5 mmol), 5-methyl-2-pyrimidin-2-yl-5,6,7,8-tetrahydropyrido[4,3-d]pyrimidine (227 mg, 1.0 mmol, the product of step 2 in Example 40), HATU (762 mg, 2.0 mmol) and DIPEA (258 mg, 2.0 mmol) in anhydrous DMF (10 mL) was stirred for 10 hrs at rt. The resulting mixture was poured into water (50 mL) and extracted with EA (50 mL) twice. The combined organic layer was washed with water and brine, dried over anhydrous $Na_2SO_4$ and concentrated in vacuo. The residue was purified by prep-HPLC to provide (1-methylindazol-3-yl)-(5-methyl-2-pyrimidin-2-yl-7,8-dihydro-5H-pyrido[4,3-d]pyrimidin-6-yl)methanone (65 mg) as a white solid. $^1$H NMR (400 MHz, Methanol-d4) δ: 9.05 (br d, 2H), 8.79-9.00 (m, 1H), 8.07 (d, 1H), 7.61-7.68 (m, 2H), 7.49 (br t, 1H), 7.29 (br s, 1H), 6.29-6.44 (br s, 0.4H), 5.96-6.10 (m, 0.6H), 5.22 (m, 0.6H), 5.02 (br s, 0.4H), 4.20 (s, 3H), 3.64-3.81 (m, 1H), 3.35-3.61 (m, 1H), 3.13-3.31 (m, 1H), 1.69-1.93 (m, 3H). MS obsd. (ESI$^+$) [(M+H)$^+$]: 386.

Example 63

1H-indazol-3-yl-(5-methyl-2-pyrimidin-2-yl-7,8-dihydro-5H-pyrido[4,3-d]pyrimidin-6-yl)methanone

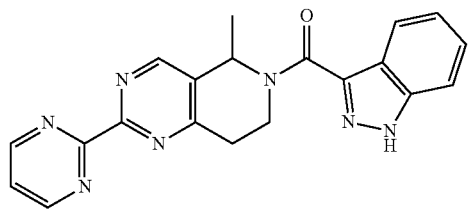 [SMILES: CC1c2cnc(-c3ncccn3)nc2CCN1C(=O)c1n[nH]c2ccccc12]

A mixture of 1H-indazole-3-carboxylic acid (243 mg, 1.5 mmol), 5-methyl-2-pyrimidin-2-yl-5,6,7,8-tetrahydropyrido[4,3-d]pyrimidine (227 mg, 1.0 mmol, the product of step 2 in Example 40), DIPEA (258 mg, 2.0 mmol) and HATU (762 mg, 2.0 mmol) in anhydrous DMF (10 mL) was stirred for 10 hrs. The resulting mixture was poured into water (50 mL) and extracted with EA (50 mL) twice. The combined organic layer was washed with water and brine, dried over anhydrous $Na_2SO_4$ and concentrated in vacuo. The residue was purified by prep-HPLC to provide 1H-indazol-3-yl-(5-methyl-2-pyrimidin-2-yl-7,8-dihydro-5H-pyrido[4,3-d]pyrimidin-6-yl)methanone (50 mg) as a white solid. $^1$H NMR (400 MHz, DMSO-d6) δ: 9.01 (br d, 3H), 8.05 (br d, 1H), 7.60-7.69 (m, 2H), 7.44 (br t, 1H), 7.24 (d, 1H), 6.22 (br s, 0.4H), 5.95 (br d, 0.6H), 5.14 (br d, 0.6H), 4.86 (br s, 0.4H), 3.70 (br t, 1H), 3.18-3.30 (m, 1H), 3.00-3.10 (m, 1H), 1.55-1.86 (m, 3H). MS obsd. (ESI$^+$) [(M+H)$^+$]: 371.

Example 64

(5-Fluoro-1H-indazol-3-yl)-(5-methyl-2-pyrimidin-2-yl-7,8-dihydro-5H-pyrido[4,3-d]pyrimidin-6-yl)methanone

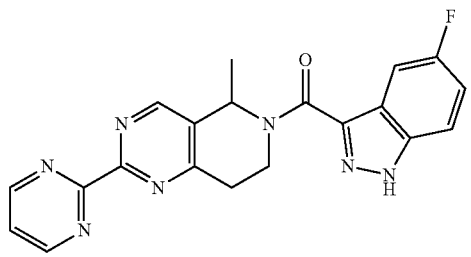 [SMILES: CC1c2cnc(-c3ncccn3)nc2CCN1C(=O)c1n[nH]c2ccc(F)cc12]

A mixture of 5-fluoro-1H-indazole-3-carboxylic acid (270 mg, 1.5 mmol), 5-methyl-2-pyrimidin-2-yl-5,6,7,8-tetrahydropyrido[4,3-d]pyrimidine (227 mg, 1.0 mmol, the product of step 2 in Example 40), DIPEA (258 mg, 2.0 mmol) and HATU (762 mg, 2.0 mmol) in anhydrous DMF (10 mL) was stirred for 10 hrs. The resulting mixture was poured into water (50 mL) and extracted with EA (50 mL) twice. The combined organic layer was washed with water and brine, dried over anhydrous $Na_2SO_4$ and concentrated in vacuo. The residue was purified by prep-HPLC to provide 5-fluoro-1H-indazol-3-yl)-(5-methyl-2-pyrimidin-2-yl-7,8-dihydro-5H-pyrido[4,3-d]pyrimidin-6-yl)methanone (6 mg) as a white solid. $^1$H NMR (400 MHz, DMSO-d6) δ: 9.00 (br d, 3H), 7.62-7.77 (m, 3H), 7.35 (br t, 1H), 6.29 (br s, 0.4H), 5.93 (br d, 0.6H), 5.23 (br d, 0.6H), 4.73-4.94 (br s, 0.4H), 3.70 (br t, 1H), 3.24 (br s, 1H), 3.00-3.10 (m, 1H), 1.65-1.86 (m, 3H). MS obsd. (ESI$^+$) [(M+H)$^+$]: 390.

Example 65

(1-Benzylindazol-3-yl)-(5-methyl-2-pyrimidin-2-yl-7,8-dihydro-5H-pyrido[4,3-d]pyrimidin-6-yl)methanone

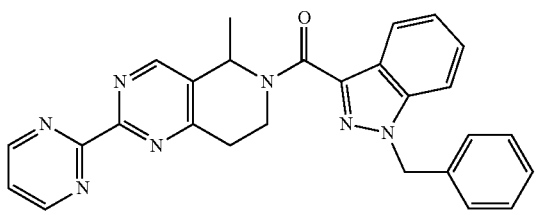 [SMILES: CC1c2cnc(-c3ncccn3)nc2CCN1C(=O)c1nn(Cc2ccccc2)c2ccccc12]

A mixture of 1-benzyl-1H-indazole-3-carboxylic acid (378 mg, 1.5 mmol), 5-methyl-2-pyrimidin-2-yl-5,6,7,8-tetrahydropyrido[4,3-d]pyrimidine (227 mg, 1.0 mmol, the product of step 2 in Example 40), DIPEA (258 mg, 2.0 mmol) and HATU (762 mg, 2.0 mmol) in anhydrous DMF (10 mL) was stirred for 10 hrs. The resulting mixture was poured into water (50 mL) and extracted with EA (50 mL) twice. The combined organic layer was washed with water and brine, dried over anhydrous $Na_2SO_4$ and concentrated in vacuo. The residue was purified by prep-HPLC to provide (1-benzylindazol-3-yl)-(5-methyl-2-pyrimidin-2-yl-7,8-dihydro-5H-pyrido[4,3-d]pyrimidin-6-yl)methanone (80 mg) as a white solid. $^1$H NMR (400 MHz, CDCl$_3$) δ: 9.02 (br d, 2H), 8.53-8.87 (m, 1H), 8.20 (br d, 1H), 7.34-7.46 (m, 3H), 7.21-7.34 (m, 6H), 6.21-6.35 (br s, 0.4H), 6.07 (br d, 0.6H), 5.54-5.70 (m, 2H), 5.28 (br d, 0.6H), 5.12 (br s, 0.4H), 3.41-3.67 (m, 1H), 3.27-3.39 (m, 1H), 3.17-3.27 (m, 1H), 1.72 (br d, 3H). MS obsd. (ESI$^+$) [(M+H)$^+$]: 462.

Example 66

(5-Methoxy-1H-indazol-3-yl)-(5-methyl-2-pyrimidin-2-yl-7,8-dihydro-5H-pyrido[4,3-d]pyrimidin-6-yl)methanone

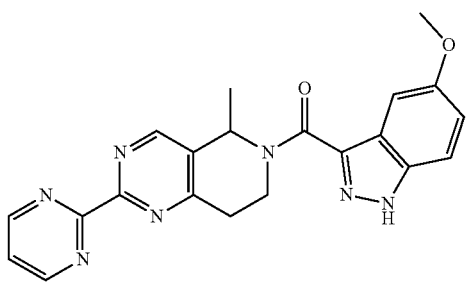 [SMILES: COc1ccc2[nH]nc(C(=O)N3CCc4nc(-c5ncccn5)ncc4C3C)c2c1]

A mixture of 5-methoxy-1H-indazole-3-carboxylic acid (288 mg, 1.5 mmol), 5-methyl-2-pyrimidin-2-yl-5,6,7,8-tetrahydropyrido[4,3-d]pyrimidine (227 mg, 1.0 mmol, the product of step 2 in Example 40), DIPEA (258 mg, 2.0 mmol) and HATU (762 mg, 2.0 mmol) in anhydrous DMF (10 mL) was stirred for 10 hrs. The resulting mixture was poured into water (50 mL) and extracted with EA (50 mL) twice. The combined organic layer was washed with water and brine, dried over anhydrous Na$_2$SO$_4$ and concentrated in vacuo. The residue was purified by prep-HPLC to provide (5-methoxy-1H-indazol-3-yl)-(5-methyl-2-pyrimidin-2-yl-7,8-dihydro-5H-pyrido[4,3-d]pyrimidin-6-yl)methanone (30 mg) as a white solid. $^1$H NMR (400 MHz, DMSO-d6) δ: 9.00 (br d, 3H), 7.64 (t, 1H), 7.55 (d, 1H), 7.43 (s, 1H), 7.08 (br d, 1H), 6.25-6.37 (br s, 0.4H), 5.93 (br d, 0.6H), 5.23 (br d, 0.6H), 4.84 (br s, 0.4H), 3.81 (s, 3H), 3.59-3.76 (m, 1H), 3.24 (m, 1H), 3.00-3.10 (m, 1H), 1.56-1.86 (m, 3H). MS obsd. (ESI$^+$) [(M+H)$^+$]: 402.

BIOLOGICAL EXAMPLES

Example 67 Materials and Methods

HBV Cell Line

HepG2.2.15 cells (Acs et al. *Proc Natl Acad Sci USA*, 84, (1987), 4641-4), a constitutively HBV-expressing cell line were cultured in DMEM+Glutamax-I medium (Invitrogen, Carlsbad, Calif., USA), supplemented with 10% fetal bovine serum (Invitrogen) and G418 (Invitrogen) at a final concentration of 200 mg/L and maintained in 5% CO$_2$ at 37° C.

HBsAg Assay

HepG2.2.15 cells were seeded in duplicate into white, 96-well plates at 1.5×10$^4$ cells/well. The cells were treated with a three-fold serial dilution series of the compounds in DMSO. The final DMSO concentration in all wells was 1% and DMSO was used as no drug control.

The HBsAg chemiluminescence immunoassay (CLIA) kit (Autobio Diagnostics Co., Zhengzhou, China, Catalog number: CL0310-2) was used to measure the levels of secreted HBV antigens semi-quantitatively. For the detection 50 µL/well culture supernatant was used and HBsAg was quantified using HBsAg chemiluminescence immunoassay (CLIA) kit (Autobio Diagnostics Co., Zhengzhou, China, Catalog number: CL0310-2), 50 µL of the supernatant was transferred to the CLIA assay plate and 50 µL of enzyme conjugate reagent was added into each well. The plates were sealed and gently agitated for 1 hour at room temperature. The supernatant-enzyme-mixture was discarded and wells were washed 6 times with 300 µL of PBS. The residual liquid was removed by plating the CLIA plate right side down on absorbent tissue paper. 25 µL of substrates A and B were added to each well. Luminance was measured using a luminometer (Mithras LB 940 Multimode Microplate Reader) after 10 minutes incubation. Dose-response curves were generated and the IC$_{50}$ value was extrapolated by using the E-WorkBook Suite (ID Business Solutions Ltd., Guildford, UK). The IC$_{50}$ was defined as the compound concentration at which HBsAg secretion was reduced by 50% compared to the no drug control.

The compounds according to formula I were tested for their capacity to inhibit HBsAg as described herein. The Examples were tested in the above assay and found to have IC$_{50}$ below 50 µM. Particular compounds of formula I were found to have IC$_{50}$ below 5.0 µM. More Particular compounds of formula I were found to have IC$_{50}$ below 0.50 µM. Results of HBsAg assay are given in Table 1.

TABLE 1

| Activity data in HBsAg assay | |
|---|---|
| Example No. | IC$_{50}$ (µM) |
| 1 | 15.667 |
| 2 | 16.971 |
| 3 | 27.27 |
| 4 | 24.312 |
| 5 | 11.41 |
| 6 | 18.74 |
| 7 | 4.86 |
| 8 | 16.35 |
| 9 | 11.49 |
| 10 | 26.23 |
| 11 | 21.04 |
| 12 | 21.41 |
| 13 | 6.56 |
| 14 | 20 |
| 15 | 4.89 |
| 16 | 8.23 |
| 17 | 7.66 |
| 18 | 10.02 |
| 19 | 8.99 |
| 20 | 7.85 |
| 21 | 5.07 |
| 22 | 27.96 |
| 23 | 21.24 |
| 24 | 3.18 |
| 25 | 34.3 |
| 26 | 3.18 |
| 27 | 24.18 |
| 28 | 9.34 |
| 29 | 34.22 |
| 30 | 25.25 |
| 31 | 31.94 |
| 32 | 1.67 |
| 33 | 8.11 |
| 34 | 1.81 |
| 35 | 2.72 |
| 36 | 3.97 |
| 37 | 25.8 |
| 38 | 21.73 |
| 39 | 10.62 |
| 40 | 1.93 |
| 41 | 0.38 |
| 42 | 0.258 |
| 43 | 0.326 |

TABLE 1-continued

Activity data in HBsAg assay

| Example No. | IC$_{50}$ (µM) |
|---|---|
| 44 | 2.455 |
| 45 | 1.431 |
| 46 | 2.076 |
| 47 | 2.466 |
| 48 | 0.472 |
| 49 | 1.11 |
| 50 | 27.738 |
| 51 | 0.627 |
| 52 | 0.637 |
| 53 | 0.51 |
| 54 | 11.518 |
| 55 | 0.223 |
| 56 | 1.082 |
| 57 | 3.228 |
| 58 | 0.279 |
| 59 | 0.55 |
| 60 | 2.614 |
| 61 | 0.082 |
| 62 | 0.42 |
| 63 | 0.45 |
| 64 | 0.21 |
| 65 | 0.39 |
| 66 | 1.36 |

HBV DNA Assay

The assay employs real-time qPCR (TaqMan) to directly measure extracellular HBV DNA copy number in the cell supernatant. HepG2.2.15 cells were plated in 96-well microtiter plates before treatment with complete medium (DMEM, Glutamax, 10% FBS, 1% Penicillin/Streptomycin, 250 µg/mL Genetycin, final DMSO concentration is 1%). Only the interior wells were utilized to reduce "edge effects" observed during cell culture, the exterior wells were filled with complete medium to help minimize sample evaporation. The HepG2.2.15 cells were treated 1 h later with various concentrations of a test compound in duplicate (top concentration used at 5 µM, 2 µM or 0.5 µM according to the HBsAg IC50 observed, with ⅓ successive dilutions (total of 10 dilutions). Six days following the initial administration of the test compound, the cell culture supernatant was collected; DNA extraction was performed by automated system (Magnapure) and then used in a real-time qPCR/TaqMan assay to determine HBV DNA copy numbers. Antiviral activity was calculated from the reduction in HBV DNA levels (IC$_{50}$). The compounds of the present invention were tested for their capacity to inhibit HBV DNA as described herein. The Examples were tested in the above assay and found to have IC$_{50}$ below 50 µM. Results of HBV DNA assay are given in Table 2.

TABLE 2

Anti HBV DNA production activity in HepG2.2.15 cells

| Example No. | IC$_{50}$ (µM) |
|---|---|
| 58 | 41.9 |
| 59 | 48.5 |

The invention claimed is:
1. A compound of formula I,

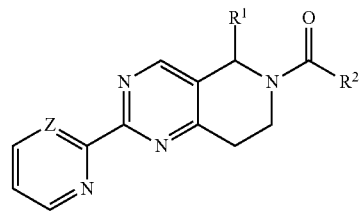

wherein:
R$^1$ is C$_{1-6}$alkoxy, C$_{1-6}$alkyl, C$_{3-7}$cycloalkyl, haloC$_{1-6}$alkoxy, haloC$_{1-6}$alkyl or hydrogen;
R$^2$ is benzothiophenyl, imidazolyl, indazolyl, indolyl, isoxazolyl, oxazolyl, phenyl, pyridinyl, pyrimidinyl, thiazolyl or thiophenyl, wherein said benzothiophenyl, imidazolyl, indazolyl, indolyl, isoxazolyl, oxazolyl, phenyl, pyridinyl, thiazolyl or thiophenyl is unsubstituted or substituted by one, two or three substituents independently selected from C$_{1-6}$alkoxy, C$_{1-6}$alkoxyC$_{1-6}$alkoxy, C$_{1-6}$alkyl, C$_{3-7}$cycloalkyl, cyano, haloC$_{1-6}$alkoxy, haloC$_{1-6}$alkyl, halogen, hydroxy, hydroxyC$_{1-6}$alkoxy, hydroxyC$_{1-6}$alkyl, nitro and phenyC$_{1-6}$alkyl; and
Z is CH or N;
or a pharmaceutically acceptable salt, or an enantiomer thereof.

2. A compound according to claim 1, wherein
R$^1$ is hydrogen or C$_{1-6}$alkyl;
R$^2$ is benzothiophenyl, imidazolyl, indazolyl, indolyl, isoxazolyl, oxazolyl, phenyl, pyridinyl, thiazolyl or thiophenyl, wherein said benzothiophenyl, imidazolyl, indazolyl, indolyl, isoxazolyl, oxazolyl, phenyl, pyridinyl, thiazolyl or thiophenyl is unsubstituted or substituted by one, two or three substituents independently selected from C$_{1-6}$alkoxy, C$_{1-6}$alkoxyC$_{1-6}$alkoxy, C$_{1-6}$alkyl, cyano, haloC$_{1-6}$alkyl, halogen, hydroxy, nitro and phenyC$_{1-6}$alkyl;
or apharmaceutically acceptable salt, or an enantiomer thereof.

3. A compound according to claim 1, wherein:
R$^1$ is hydrogen, methyl or ethyl; and
R$^2$ is benzothiophenyl, imidazolyl, indazolyl, indolyl, isoxazolyl, oxazolyl, phenyl, pyridinyl, thiazolyl or thiophenyl, wherein said benzothiophenyl, imidazolyl, indazolyl, indolyl, isoxazolyl, oxazolyl, phenyl, pyridinyl, thiazolyl or thiophenyl is unsubstituted or substituted by one, two or three substituents independently selected from ethoxy, methoxy, methoxyethoxy, methoxypropoxy, methyl, cyano, trifluoromethyl, bromo, chloro, fluoro, hydroxy, nitro and phenylmethyl;
or a pharmaceutically acceptable salt, or an enantiomer thereof.

4. A compound according to claim 1, or a pharmaceutically acceptable salt, or an enantiomer thereof, wherein R$^1$ is C$_{1-6}$alkyl.

5. A compound according to claim 1, or a pharmaceutically acceptable salts or an enantiomer thereof, wherein R$^1$ is methyl.

6. A compound according to any claim 1, or a pharmaceutically acceptable salt, or an enantiomer thereof, wherein R² is indazolyl, phenyl, thiazolyl or thiophenyl, said indazolyl, phenyl, thiazolyl or thiophenyl is unsubstituted, or substituted by one or two substituents independently selected from $C_{1-6}$alkoxy, $C_{1-6}$alkoxy$C_{1-6}$alkoxy, $C_{1-6}$alkyl, halogen and phenyl$C_{1-6}$alkyl.

7. A compound according to claim 1, or a pharmaceutically acceptable salt, or an enantiomer thereof, wherein R² is indazolyl, phenyl, thiazolyl or thiophenyl, said indazolyl, phenyl, thiazolyl or thiophenyl is unsubstituted, or substituted by one or two substituents independently selected from methoxy, methoxypropoxy, methyl, chloro, fluoro and phenylmethyl.

8. A compound according to claim 1, wherein
R¹ is $C_{1-6}$alkyl or hydrogen; and
R² is indazolyl, $C_{1-6}$alkoxyindazolyl, haloindazolyl, (phenyl$C_{1-6}$alkyl)indazolyl, ($C_{1-6}$alkoxy$C_{1-6}$alkoxy)halophenyl, $C_{1-6}$alkoxy($C_{1-6}$alkoxy$C_{1-6}$alkoxy)phenyl, thiazolyl, $C_{1-6}$alkylthiazolyl, di$C_{1-6}$alkylthiazolyl, $C_{1-6}$alkoxythiophenyl or $C_{1-6}$alkylthiophenyl;
or a pharmaceutically acceptable salt, or an enantiomer thereof.

9. A compound according to claim 1, wherein:
R¹ is methyl or hydrogen; and
R² is indazolyl, methoxyindazolyl, fluoroindazolyl, (phenylmethyl)indazolyl, (methoxypropoxy)chlorophenyl, methoxy(methoxypropoxy)phenyl, thiazolyl, methylthiazolyl, dimethylthiazolyl, methoxythiophenyl or methylthiophenyl;
or a pharmaceutically acceptable salt, or an enantiomer thereof.

10. A compound according to claim 1, selected from:
[2-(2-pyridyl)-7,8-dihydro-5H-pyrido[4,3-d]pyrimidin-6-yl]-[4-(trifluoromethyl)phenyl]methanone;
4-[2-(2-pyridyl)-7,8-dihydro-5H-pyrido[4,3-d]pyrimidine-6-carbonyl]benzonitrile;
(4-nitrophenyl)-[2-(2-pyridyl)-7,8-dihydro-5H-pyrido[4,3-d]pyrimidin-6-yl]methanone;
phenyl-[2-(2-pyridyl)-7,8-dihydro-5H-pyrido[4,3-d]pyrimidin-6-yl]methanone;
(4-chlorophenyl)-[2-(2-pyridyl)-7,8-dihydro-5H-pyrido[4,3-d]pyrimidin-6-yl]methanone;
[2-(2-pyridyl)-7,8-dihydro-5H-pyrido[4,3-d]pyrimidin-6-yl]-[3-(trifluoromethyl)phenyl]methanone;
(3-fluoro-4-methoxy-phenyl)-[2-(2-pyridyl)-7,8-dihydro-5H-pyrido[4,3-d]pyrimidin-6-yl]methanone;
(4-fluorophenyl)-[2-(2-pyridyl)-7,8-dihydro-5H-pyrido[4,3-d]pyrimidin-6-yl]methanone;
(4-fluoro-3-methoxy-phenyl)-[2-(2-pyridyl)-7,8-dihydro-5H-pyrido[4,3-d]pyrimidin-6-yl]methanone;
(3,4-difluorophenyl)-[2-(2-pyridyl)-7,8-dihydro-5H-pyrido[4,3-d]pyrimidin-6-yl]methanone;
(4-fluoro-3-hydroxy-phenyl)-[2-(2-pyridyl)-7,8-dihydro-5H-pyrido[4,3-d]pyrimidin-6-yl]methanone;
(3-fluoro-4-hydroxy-phenyl)-[2-(2-pyridyl)-7,8-dihydro-5H-pyrido[4,3-d]pyrimidin-6-yl]methanone;
(4-ethoxy-3-fluoro-phenyl)-[2-(2-pyridyl)-7,8-dihydro-5H-pyrido[4,3-d]pyrimidin-6-yl]methanone;
[3-fluoro-4-(2-methoxyethoxy)phenyl]-[2-(2-pyridyl)-7,8-dihydro-5H-pyrido[4,3-d]pyrimidin-6-yl]methanone;
[3-fluoro-4-(3-methoxypropoxy)phenyl]-[2-(2-pyridyl)-7,8-dihydro-5H-pyrido[4,3-d]pyrimidin-6-yl]methanone;
[2-(2-pyridyl)-7,8-dihydro-5H-pyrido[4,3-d]pyrimidin-6-yl]-(3,4,5-trimethoxyphenyl)methanone;
(3,5-diethoxyphenyl)-[2-(2-pyridyl)-7,8-dihydro-5H-pyrido[4,3-d]pyrimidin-6-yl]methanone;
(3-chloro-5-methoxy-phenyl)-[2-(2-pyridyl)-7,8-dihydro-5H-pyrido[4,3-d]pyrimidin-6-yl]methanone;
(3,5-dimethoxyphenyl)-[2-(2-pyridyl)-7,8-dihydro-5H-pyrido[4,3-d]pyrimidin-6-yl]methanone;
(4-fluoro-3-methyl-phenyl)-[2-(2-pyridyl)-7,8-dihydro-5H-pyrido[4,3-d]pyrimidin-6-yl]methanone;
(3-chloro-4-methoxy-phenyl)-[2-(2-pyridyl)-7,8-dihydro-5H-pyrido[4,3-d]pyrimidin-6-yl]methanone;
(3,4-dimethoxyphenyl)-[2-(2-pyridyl)-7,8-dihydro-5H-pyrido[4,3-d]pyrimidin-6-yl]methanone;
(3-chloro-4-hydroxy-phenyl)-[2-(2-pyridyl)-7,8-dihydro-5H-pyrido[4,3-d]pyrimidin-6-yl]methanone;
[3-chloro-4-(3-methoxypropoxy)phenyl]-[2-(2-pyridyl)-7,8-dihydro-5H-pyrido[4,3-d]pyrimidin-6-yl]methanone;
(4-hydroxy-3-methoxy-phenyl)-[2-(2-pyridyl)-7,8-dihydro-5H-pyrido[4,3-d]pyrimidin-6-yl]methanone;
[3-methoxy-4-(3-methoxypropoxy)phenyl]-[2-(2-pyridyl)-7,8-dihydro-5H-pyrido[4,3-d]pyrimidin-6-yl]methanone;
(5-methyl-2-pyridyl)-[2-(2-pyridyl)-7,8-dihydro-5H-pyrido[4,3-d]pyrimidin-6-yl]methanone;
(3-fluoro-4-methyl-phenyl)-[2-(2-pyridyl)-7,8-dihydro-5H-pyrido[4,3-d]pyrimidin-6-yl]methanone;
(5-methoxy-2-pyridyl)-[2-(2-pyridyl)-7,8-dihydro-5H-pyrido[4,3-d]pyrimidin-6-yl]methanone;
(3,5-difluoro-4-methoxy-phenyl)-[2-(2-pyridyl)-7,8-dihydro-5H-pyrido[4,3-d]pyrimidin-6-yl]methanone;
(6-methyl-3-pyridyl)-[2-(2-pyridyl)-7,8-dihydro-5H-pyrido[4,3-d]pyrimidin-6-yl]methanone;
(4-methyl-2-thienyl)-[2-(2-pyridyl)-7,8-dihydro-5H-pyrido[4,3-d]pyrimidin-6-yl]methanone;
(5-methylisoxazol-3-yl)-[2-(2-pyridyl)-7,8-dihydro-5H-pyrido[4,3-d]pyrimidin-6-yl]methanone;
(3,4-dimethoxyphenyl)-[(5S)-5-methyl-2-(2-pyridyl)-7,8-dihydro-5H-pyrido[4,3-d]pyrimidin-6-yl]methanone;
(3,4-dimethoxyphenyl)-[(5S)-5-ethyl-2-(2-pyridyl)-7,8-dihydro-5H-pyrido[4,3-d]pyrimidin-6-yl]methanone;
(6-methoxy-3-pyridyl)-[2-(2-pyridyl)-7,8-dihydro-5H-pyrido[4,3-d]pyrimidin-6-yl]methanone;
(3,5-difluorophenyl)-[2-(2-pyridyl)-7,8-dihydro-5H-pyrido[4,3-d]pyrimidin-6-yl]methanone;
(3-fluoro-5-methoxy-phenyl)-[2-(2-pyridyl)-7,8-dihydro-5H-pyrido[4,3-d]pyrimidin-6-yl]methanone;
(4-methoxyphenyl)-[2-(2-pyridyl)-7,8-dihydro-5H-pyrido[4,3-d]pyrimidin-6-yl]methanone;
[3-chloro-4-(3-methoxypropoxy)phenyl]-(5-methyl-2-pyrimidin-2-yl-7,8-dihydro-5H-pyrido[4,3-d]pyrimidin-6-yl)methanone;
[5-methyl-2-(2-pyridyl)-7,8-dihydro-5H-pyrido[4,3-d]pyrimidin-6-yl]-(4-methyl-2-thienyl)methanone;
(5-chloro-2-thienyl)-[5-methyl-2-(2-pyridyl)-7,8-dihydro-5H-pyrido[4,3-d]pyrimidin-6-yl]methanone;
[5-methyl-2-(2-pyridyl)-7,8-dihydro-5H-pyrido[4,3-d]pyrimidin-6-yl]-(5-methyl-2-thienyl)methanone;
[5-methyl-2-(2-pyridyl)-7,8-dihydro-5H-pyrido[4,3-d]pyrimidin-6-yl]-(3-thienyl)methanone;
(4-methyloxazol-5-yl)-[5-methyl-2-(2-pyridyl)-7,8-dihydro-5H-pyrido[4,3-d]pyrimidin-6-yl]methanone;
1H-indol-6-yl-[5-methyl-2-(2-pyridyl)-7,8-dihydro-5H-pyrido[4,3-d]pyrimidin-6-yl]methanone;
1H-indazol-5-yl-[5-methyl-2-(2-pyridyl)-7,8-dihydro-5H-pyrido[4,3-d]pyrimidin-6-yl]methanone;
benzothiophen-2-yl-[5-methyl-2-(2-pyridyl)-7,8-dihydro-5H-pyrido[4,3-d]pyrimidin-6-yl]methanone;

[5-methyl-2-(2-pyridyl)-7,8-dihydro-5H-pyrido[4,3-d]pyrimidin-6-yl]-(2-thienyl)methanone;
[5-methyl-2-(2-pyridyl)-7,8-dihydro-5H-pyrido[4,3-d]pyrimidin-6-yl]-(3-methyl-2-thienyl)methanone;
[5-methyl-2-(2-pyridyl)-7,8-dihydro-5H-pyrido[4,3-d]pyrimidin-6-yl]-thiazol-2-yl-methanone;
[5-methyl-2-(2-pyridyl)-7,8-dihydro-5H-pyrido[4,3-d]pyrimidin-6-yl]-(2-methylthiazol-5-yl)methanone;
(5-bromo-2-thienyl)-[5-methyl-2-(2-pyridyl)-7,8-dihydro-5H-pyrido[4,3-d]pyrimidin-6-yl]methanone;
[5-methyl-2-(2-pyridyl)-7,8-dihydro-5H-pyrido[4,3-d]pyrimidin-6-yl]-thiazol-5-yl-methanone;
[5-methyl-2-(2-pyridyl)-7,8-dihydro-5H-pyrido[4,3-d]pyrimidin-6-yl]-(5-methylthiazol-2-yl)methanone;
1H-imidazol-2-yl-[5-methyl-2-(2-pyridyl)-7,8-dihydro-5H-pyrido[4,3-d]pyrimidin-6-yl]methanone;
(1-methylimidazol-2-yl)-[5-methyl-2-(2-pyridyl)-7,8-dihydro-5H-pyrido[4,3-d]pyrimidin-6-yl]methanone;
(5-methoxy-2-thienyl)-[5-methyl-2-(2-pyridyl)-7,8-dihydro-5H-pyrido[4,3-d]pyrimidin-6-yl]methanone;
[5-methyl-2-(2-pyridyl)-7,8-dihydro-5H-pyrido[4,3-d]pyrimidin-6-yl]-[4-(trifluoromethyl)thiazol-2-yl]methanone;
[5-methyl-2-(2-pyridyl)-7,8-dihydro-5H-pyrido[4,3-d]pyrimidin-6-yl]-oxazol-2-yl-methanone;
(4,5-dimethylthiazol-2-yl)-[5-methyl-2-(2-pyridyl)-7,8-dihydro-5H-pyrido[4,3-d]pyrimidin-6-yl]methanone;
(1-methylindazol-3-yl)-(5-methyl-2-pyrimidin-2-yl-7,8-dihydro-5H-pyrido[4,3-d]pyrimidin-6-yl)methanone;
1H-indazol-3-yl-(5-methyl-2-pyrimidin-2-yl-7,8-dihydro-5H-pyrido[4,3-d]pyrimidin-6-yl)methanone;
(5-fluoro-1H-indazol-3-yl)-(5-methyl-2-pyrimidin-2-yl-7,8-dihydro-5H-pyrido[4,3-d]pyrimidin-6-yl)methanone;
(1-benzylindazol-3-yl)-(5-methyl-2-pyrimidin-2-yl-7,8-dihydro-5H-pyrido[4,3-d]pyrimidin-6-yl)methanone; and
(5-methoxy-1H-indazol-3-yl)-(5-methyl-2-pyrimidin-2-yl-7,8-dihydro-5H-pyrido[4,3-d]pyrimidin-6-yl)methanone;
or a pharmaceutically acceptable salt, or an enantiomer thereof.

11. A compound according to claim 1, selected from
[3-methoxy-4-(3-methoxypropoxy)phenyl]-[2-(2-pyridyl)-7,8-dihydro-5H-pyrido[4,3-d]pyrimidin-6-yl]methanone;
[3-chloro-4-(3-methoxypropoxy)phenyl]-(5-methyl-2-pyrimidin-2-yl-7,8-dihydro-5H-pyrido[4,3-d]pyrimidin-6-yl)methanone;
[5-methyl-2-(2-pyridyl)-7,8-dihydro-5H-pyrido[4,3-d]pyrimidin-6-yl]-(4-methyl-2-thienyl)methanone;
[5-methyl-2-(2-pyridyl)-7,8-dihydro-5H-pyrido[4,3-d]pyrimidin-6-yl]-(5-methyl-2-thienyl)methanone;
[5-methyl-2-(2-pyridyl)-7,8-dihydro-5H-pyrido[4,3-d]pyrimidin-6-yl]-thiazol-2-yl-methanone;
[5-methyl-2-(2-pyridyl)-7,8-dihydro-5H-pyrido[4,3-d]pyrimidin-6-yl]-(5-methylthiazol-2-yl)methanone;
(5-methoxy-2-thienyl)-[5-methyl-2-(2-pyridyl)-7,8-dihydro-5H-pyrido[4,3-d]pyrimidin-6-yl]methanone;
(4,5-dimethylthiazol-2-yl)-[5-methyl-2-(2-pyridyl)-7,8-dihydro-5H-pyrido[4,3-d]pyrimidin-6-yl]methanone;
1H-indazol-3-yl-(5-methyl-2-pyrimidin-2-yl-7,8-dihydro-5H-pyrido[4,3-d]pyrimidin-6-yl)methanone;
(5-fluoro-1H-indazol-3-yl)-(5-methyl-2-pyrimidin-2-yl-7,8-dihydro-5H-pyrido[4,3-d]pyrimidin-6-yl)methanone;
(1-benzylindazol-3-yl)-(5-methyl-2-pyrimidin-2-yl-7,8-dihydro-5H-pyrido[4,3-d]pyrimidin-6-yl)methanone; and
(5-methoxy-1H-indazol-3-yl)-(5-methyl-2-pyrimidin-2-yl-7,8-dihydro-5H-pyrido[4,3-d]pyrimidin-6-yl)methanone;
or a pharmaceutically acceptable salt, or an enantiomer thereof.

12. A process for the preparation of a compound according to claim 1, the process comprising:
coupling of a compound of formula (A)

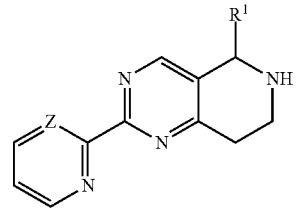

(A)

with a compound of formula (B)

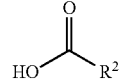

(B)

in the presence of a coupling reagent and a base;
wherein, $R^1$, $R^2$ and Z are defined as in claim 1.

13. A pharmaceutical composition comprising a compound in accordance with claim 1 and a therapeutically inert carrier.

14. A method for the treatment of HBV infection, which method comprises administering to a subject in need thereof an effective amount of a compound as defined in claim 1.

* * * * *